United States Patent
Lee et al.

(10) Patent No.: US 12,365,725 B2
(45) Date of Patent: **\*Jul. 22, 2025**

(54) METHODS FOR TREATING OSTEOGENESIS IMPERFECTA

(71) Applicants: GENZYME CORPORATION, Cambridge, MA (US); Baylor College of Medicine, Houston, TX (US)

(72) Inventors: Brendan Lee, Houston, TX (US); Kuber T. Sampath, Holliston, MA (US)

(73) Assignees: Genzyme Corporation, Cambridge, MA (US); Baylor College of Medicine, Houston, TX (US)

( * ) Notice: Subject to any disclaimer, the term of this patent is extended or adjusted under 35 U.S.C. 154(b) by 126 days.

This patent is subject to a terminal disclaimer.

(21) Appl. No.: 17/547,069

(22) Filed: Dec. 9, 2021

(65) Prior Publication Data

US 2022/0195025 A1 Jun. 23, 2022

Related U.S. Application Data

(63) Continuation of application No. 16/459,023, filed on Jul. 1, 2019, now Pat. No. 11,230,595, which is a continuation of application No. 15/427,920, filed on Feb. 8, 2017, now Pat. No. 10,377,819, which is a continuation of application No. 14/772,708, filed as application No. PCT/US2014/031279 on Mar. 20, 2014, now Pat. No. 9,598,486.

(60) Provisional application No. 61/883,151, filed on Sep. 26, 2013, provisional application No. 61/875,399, filed on Sep. 9, 2013, provisional application No. 61/803,647, filed on Mar. 20, 2013.

(51) Int. Cl.
```
A61K 39/395    (2006.01)
A61K 33/42     (2006.01)
A61K 39/00     (2006.01)
A61K 45/06     (2006.01)
C07K 16/22     (2006.01)
```

(52) U.S. Cl.
CPC .............. C07K 16/22 (2013.01); A61K 33/42 (2013.01); A61K 39/39533 (2013.01); A61K 39/3955 (2013.01); A61K 45/06 (2013.01); A61K 2039/505 (2013.01); C07K 2317/21 (2013.01); C07K 2317/51 (2013.01); C07K 2317/515 (2013.01); C07K 2317/52 (2013.01); C07K 2317/56 (2013.01); C07K 2317/565 (2013.01); C07K 2317/76 (2013.01)

(58) Field of Classification Search
None
See application file for complete search history.

(56) References Cited

U.S. PATENT DOCUMENTS

| | | |
|---|---|---|
| 3,600,132 A | 8/1971 | Goverde |
| 6,416,737 B1 | 7/2002 | Manolagas et al. |
| 6,489,445 B1 | 12/2002 | Brunkow et al. |
| 6,492,497 B1 | 12/2002 | Thompson et al. |
| 7,368,111 B2 | 5/2008 | Thompson et al. |
| 7,592,429 B2* | 9/2009 | Paszty ................. A61P 3/10 530/387.3 |
| 7,985,834 B2 | 7/2011 | Winkler et al. |
| 8,246,953 B2 | 8/2012 | Kniessel et al. |
| 9,598,486 B2* | 3/2017 | Lee ................... C07K 16/22 |
| 10,377,819 B2* | 8/2019 | Lee ................... A61P 13/12 |
| 11,230,595 B2* | 1/2022 | Lee ................... A61P 19/08 |
| 2005/0026870 A1 | 2/2005 | Roldan et al. |
| 2010/0204053 A1* | 8/2010 | Glimcher ............. A61P 19/00 506/9 |
| 2011/0150866 A1 | 6/2011 | Brunkow et al. |
| 2012/0294868 A1 | 11/2012 | Edwards et al. |

FOREIGN PATENT DOCUMENTS

| | | |
|---|---|---|
| WO | WO 2005/003158 | 1/2005 |
| WO | WO 2006/086469 A2 | 8/2006 |
| WO | WO 2007/076391 | 7/2007 |
| WO | WO 2008/022182 A1 | 2/2008 |
| WO | WO 2008/100384 A2 | 8/2008 |
| WO | WO 2009/091905 A1 | 7/2009 |

OTHER PUBLICATIONS

Rauch et al. (2004, Lancet 363:1377-1385).*
Grafe et al. (2014, Nature Medicine 20(6):670-676).*
U.S. Appl. No. 14/772,708, filed Sep. 3, 2015, U.S. Pat. No. 9,598,486, Mar. 21, 2017.
U.S. Appl. No. 15/427,920, filed Feb. 8, 2017, U.S. Pat. No. 10,377,819, Aug. 13, 2019.
U.S. Appl. No. 16/459,023, filed Jul. 1, 2019, U.S. Pat. No. 11,230,595, Jan. 25, 2022.
Hearing Loss—Osteogenesis Imperfecta Foundation_OIF.org [online], [retrieved on Jun. 12, 2016]. Retrieved form the internet: URL<http://www.oif.org/site/PageServer?pagename=HearLoss>.
Adult OI Health Concerns—Osteogenesis Imperfecta Foundation_OIF.org [online], [retrieved on Jun. 12, 2016]. Retrieved from the internet: URL<http://www.oif.org/site/PageServer?pagename=adultHealth>.
National Osteoporosis Society, "Osteogenesis imperfecta and osteoporosis," (Dec. 2008). Accessible on the Internet at URL: http://www.riversideschool.org.uk/aUachments/download.asp?file=234&type=doc. [Last Accessed Jul. 13, 2017].
Adami et al., "Intravenous Neridronate in Adults With Osteogenesis Imperfecta," J Bone Miner Res. (2003) 18(1):126-30.

(Continued)

Primary Examiner — Elizabeth C. Kemmerer
(74) Attorney, Agent, or Firm — Steptoe LLP; Z. Ying Li; Mauricio Alvarez

(57) ABSTRACT

The present invention provides methods for treating and improving the symptoms of osteogenesis imperfecta (OI) in a subject by administering to the subject a therapeutically effective amount of a binding agent that binds to transforming growth factor beta (TGFβ).

8 Claims, 27 Drawing Sheets

Specification includes a Sequence Listing.

(56) References Cited

OTHER PUBLICATIONS

Alexander et al., "Altered TGF-beta signaling contributes to skeletal and extraskeletal manifestations in the Crtap-/-model of recessive Osteogenesis Imperfecta," American Society for Bone and Mineral Research, (2013) ASBMR Annual Meeting, 2 pgs.
Avnet et al., "Osteoblasts from a mandibuloacral dysplasia patient induce human blood precursors to differentiate into active osteoclasts," Biochim Biophys Acta (2011) 1812(7):711-8.
Bedinger et al., "Development and characterization of human monoclonal antibodies that neutralize multiple TGFβ isoforms," MAbs. (2016) 8(2):389-404.
Binkert et al., "Regulation of osteogenesis by fetuin," J Biol Chem (1999) 274(40):28514-20.
Biswas et al., "Anti-Transforming Growth Factor ß Antibody Treatment Rescues Bone Loss and Prevents Breast Cancer Metastasis to Bone," PLoS one (2011) 6(11):1-12.
Bonewald & Mundy, "Role of Transforming Growth Factor-Beta in Bone Remodeling," Clin Orthop Relat Res. (1990) 250:261-76.
Chevrel et al., "Effects of Oral Alendronate on BMD in Adult Patients With Osteogenesis Imperfecta: A 3-Year Randomized Placebo-Controlled Trial," J Bone Miner Res. (2006) 21(2):300-06.
Dubose et al., "Thrombospondin-1 inhibits osteogenic differentiation of human mesenchymal stem cells through latent TGF-β activation," Biochem Biophys Res Commun. (2012) 422:488-493.
Edwards et al. "Inhibition of TGF-β signaling 1D11 antibody treatment increases bone mass and quality in vivo," Journal of Bone and Mineral Research. (2010) 25(11):2419-2426.
Erlebacher et al. "Osteoblastic Responses to TGF-β during Bone Remodeling," (1998) Molecular Biology of the Cell 9(7):1903-1918.
Forlino et al., "New perspectives on osteogenesis imperfecta," Nature Reviews, Endocrinology (2011) 7(9):540-57.
Gebken et al. "Increased cell surface expression of receptors for transforming growth factor-beta on osteoblasts from patients with osteogenesis imperfecta," Pathobiology. (2000) 68(3):106-112.
Glorieux "Experience with bisphosphonates in osteogenesis imperfecta," Pediatrics. (2007) 119:S163-S165.
Glorieux et al., "BPS804 Anti-Sclerostin Antibody in Adults With Moderate Osteogenesis Imperfecta: Results of a Randomized Phase 2a Trial," J Bone Miner Res. (2017) 32(7):1496-1504.
Grafe et al., "Excessive transmforming growth-factor[beta] signaling is a common mechanizm in osteogenesis imperfecta," Nature Medicince (2014).
Grafe et al., "Sclerostin Antibody Treatment Improves the Bone Phenotype of Crtap-/- Mice, a Model of Recessive Osteogenesis Imperfecta," J Bone Miner Res. (2016) 31(5):1030-40.
Köhler et al., "Continuous cultures of fused cells secreting antibody of predefined specificity," Nature. (1975) 256(5517):495-7.
MacLean et al., "Systematic Review: Comparative Effectiveness of Treatments to Prevent Fractures in Men and Women with Low Bone Density or Osteoporosis," Ann Intern Med. (2008) 148(3)197-213.
Marini et al., "Null mutations in LEPRE1 and CRTAP cause severe recessive osteogenesis imperfecta," Cell and Tissue Research (2009) 339(1):59-70.
Marini & Smith, "Osteogenesis Imperfecta," In: Feingold KR, Anawalt B, Boyce A, et al., editors. Endotext (2015).
Martin et al., "Osteogenesis Imperfecta: Epidemiology and Pathophysiology" Curr Osteoporos Rep. Sep. 2007;5(3):91-7.
Morello et al., "CRTAP Is Required for Prolyl 3-Hydroxylation and Mutations Cause Recessive Osteogenesis Imperfecta," Cell (2006) 127:291-304.
Morike et al. "Effects of transforming growth factor beta on cells derived from bone and callus of patients with osteogenesis imperfecta," Journal of Orthopaedic Research. (1993) 11(4):564-573.
Opsahl et al. "Is the lingual forming part of the incisor a structural entity?: Evidences from the fragilitas ossium (fro/fro) mouse mutation and the TGFβ1 overexpressing transgenic strain," Archives of Oral Biology. (2005) 50(2):279-286.
Orwoll et al., "Evaluation of teriparatide treatment in adults with osteogenesis imperfecta," J Clin Invest. (2014) 124(2):491-98.
Pedersen et al., "Lack of effects of human calcitonin in osteogenesis imperfecta," Acta Orthop Scand. (1985) 56(3)260-64.
Powell et al., "Compendium of excipients for parenteral formulations," PDA J Pharm Sci Technol. (1998) 52(5):238-311.
Salazar et al., "Embryonic ablation of osteoblast Smad4 interrupts matrix synthesis in response to canonical Wnt signaling and causes an osteogenesis-imperfecta-like phenotype," J Cell Sci. (2013) 126:4974-84.
Seitzer et al. "Transforming growth factor β1 influences lysyl hydroxylation of collagen I and reduces steady-state levels of lysyl hydroxylase mRNA in human osteoblast-like cells," European Journal of Clinical Investigation. (1995) 25(12):959-966.
Semler et al., "First use of the RAN KL antibody denosumab in osteogenesis imperfecta type VI," J Musculoskelet Neuronal Interact. (2012)12(3):183-8.
Sinder et al., "Sclerostin antibody improves skeletal parameters in Brtl/+ mouse model of osteogenesis imperfecta," J Bone Miner Res. (2013) 28(1):73-80.
Sousa et al., "Letter to the Editor: Therapies for Osteogenesis Imperfecta," Acta Med Port. (2017) 30(2):156-57.
Tam et al., "A multicenter study to evaluate pulmonary function in osteogenesis imperfecta," Clin Genet. (2018) 94(6):502-11.
Tang et al, Regulation of postnatal bone homeostasis by TGF13 BoneKEy Reports 2, (2013) Article No. 255 1-5.
Tauer et al., "Effect of anti-TGF-b treatment in a mouse model of severe osteogenesis imperfecta," J Bone Miner Res. (2019) 34(2):207-214.
Taylor et al., "A transgenic mouse that expresses a diversity of human sequence heavy and light chain immunoglobulins," Nucleic Acids Research (1992) 20:23:6287-6295.
Trachtman et al., "A phase 1, single-dose study of fresolimumab, an anti-TGF-[beta] antibody, in treatment-resistant primary focal segmental glomerulosclerosis," Kidney International (2011) 79(11):1236-43.
Wu et al., "Receptor-mediated in vitro gene transformation by a soluble DNA carrier system," J Biol Chem. (1987) 262(10):4429-32.
Yamauchi, "Effects of intermittent compressive force on transforming growth factor beta and osteopontin synthesis in cultured bone cells," Kanagawa Shigaku. (1990) 24(4):716-29.
Proposed INN, WHO Drug Information (2009) 23:2, 2 pgs.
International Search Report with Written Opinion corresponding to International Patent Application No. PCT/US2014/031279, issued Jul. 29, 2014.
International Preliminary Report Patentability corresponding to International Patent Application No. PCT/US2014/031279, issued Sep. 22, 2015.
European Patent Office, Notice of Opposition dated Jun. 4, 2019 in EP Patent No. 2976359, 14 pgs.
European Patent Office, Notice of Opposition to a European Patent dated May 29, 2019 in EP Patent No. 2976359, 13 pgs.
European Patent Office, Response to Notice of Opposition dated Oct. 22, 2019 in EP Patent No. 2976359, 27 pgs.
European Patent Office, Summons to Attend Oral Proceedings dated Feb. 19, 2020 in EP Patent No. 2976359, 14 pgs.
European Patent Office, Submission in Response to the Preliminary Opinion from the Opposition Division dated Apr. 8, 2021 in EP Patent No. 2976359, 16 pgs.
European Patent Office, Information about the Result of Oral Proceedings dated Jun. 8, 2021 in EP Patent No. 2976359, 1 pg.

* cited by examiner

Crtap Luciferase

Fig. 7A
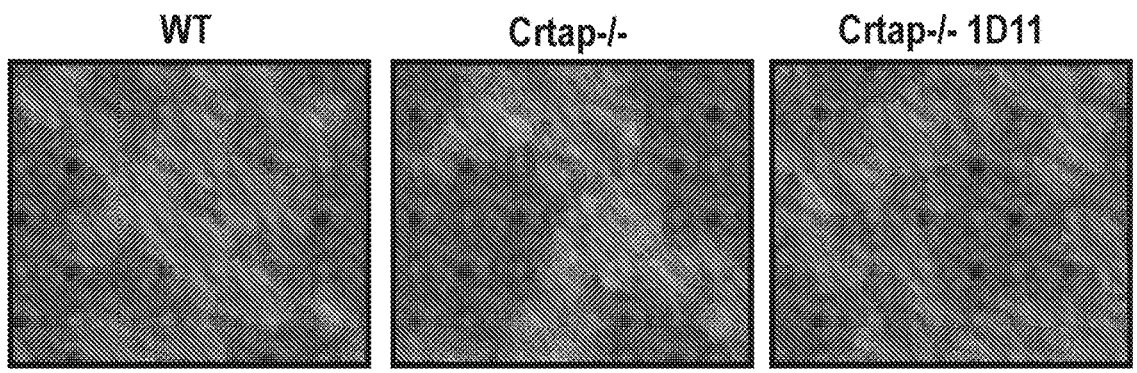
Fig. 7B
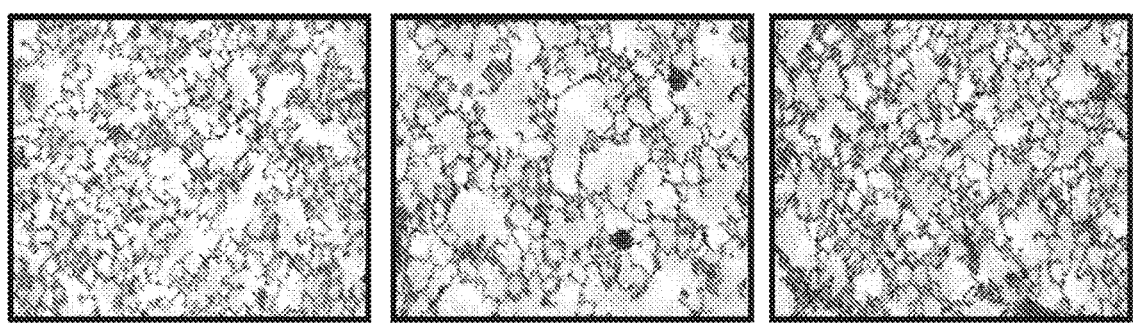
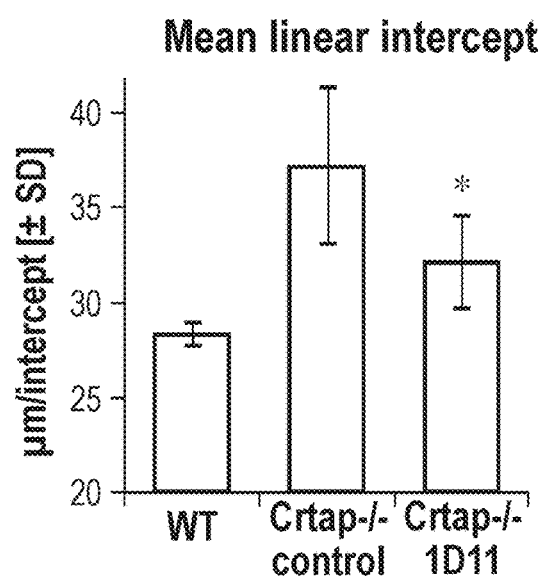
Fig. 7C

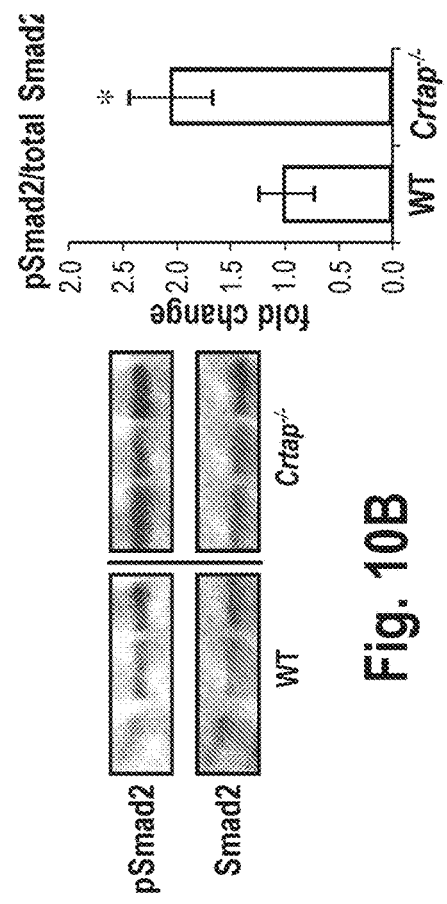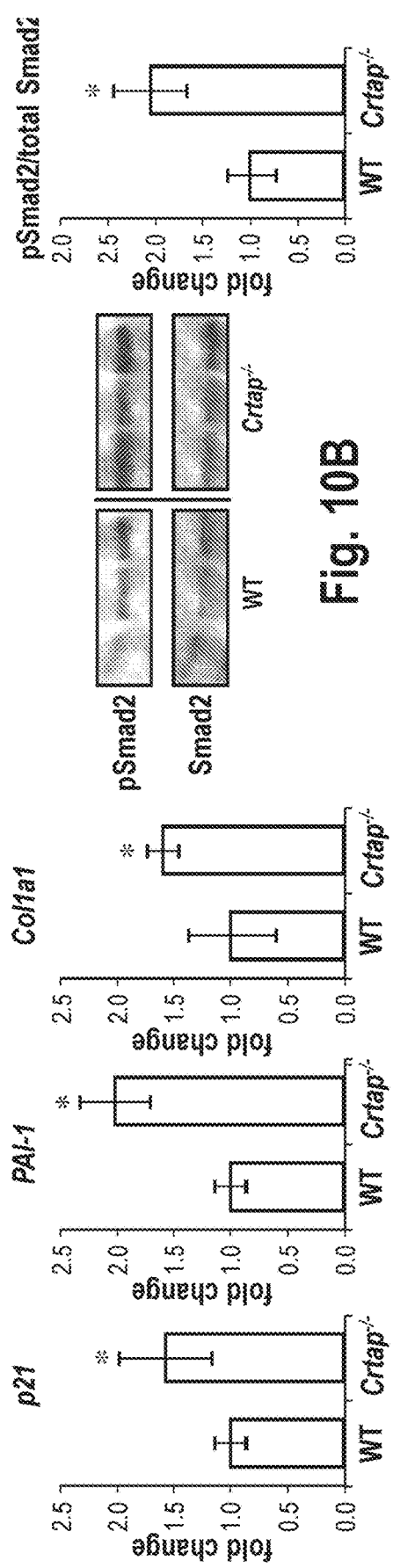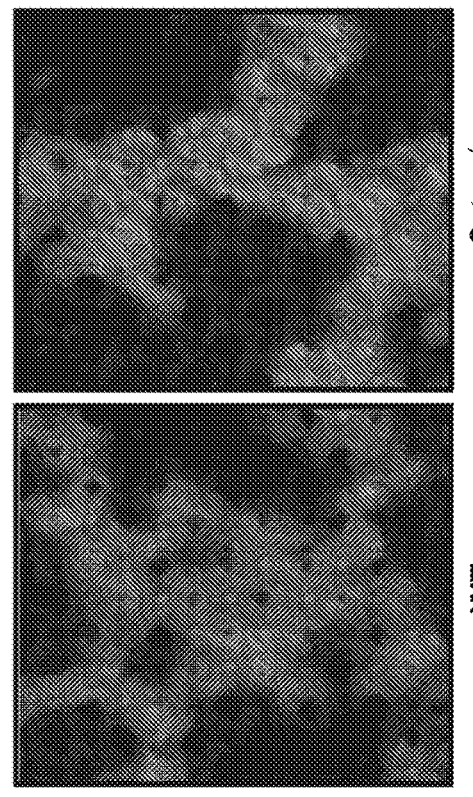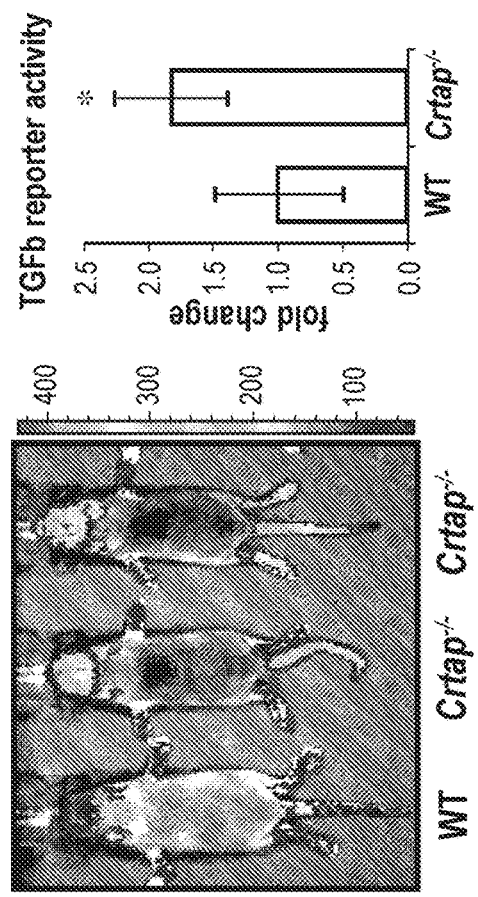
Fig. 10A  Fig. 10B  Fig. 10C  Fig. 10D  Fig. 10E  Fig. 10F

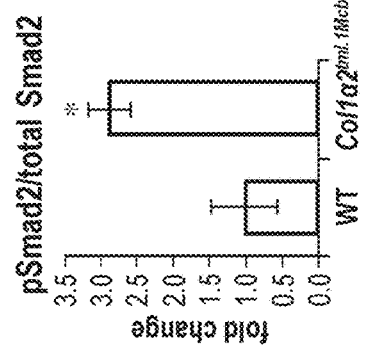
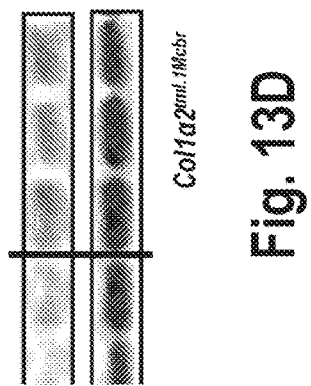
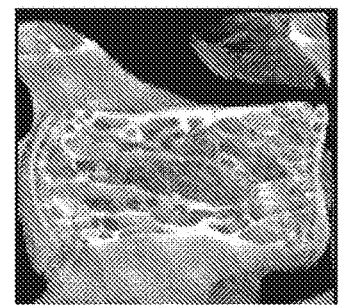
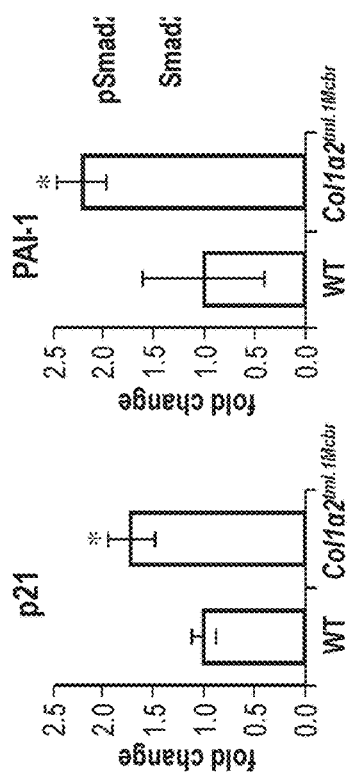
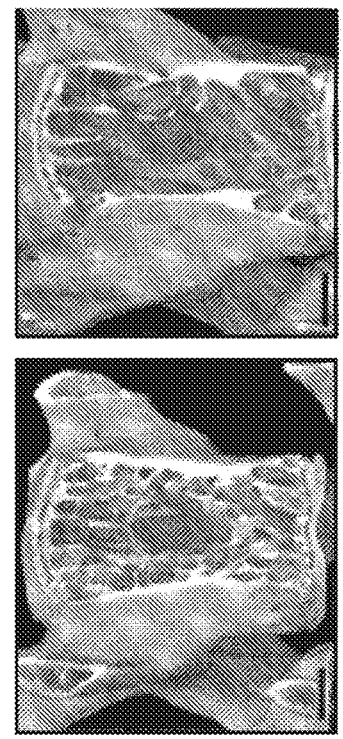
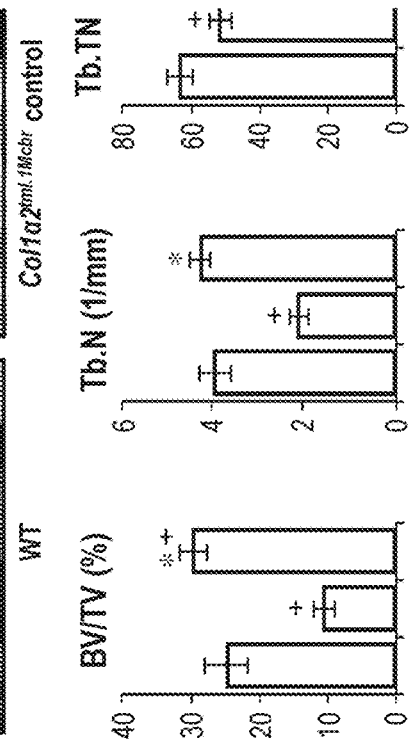
Fig. 13A  Fig. 13B  Fig. 13C  Fig. 13D  Fig. 13E

| | BV/TV (%) | Tb.N (1/mm) | Tb.Th (μm) | Tb.Sp (mm) | BMD BV (mg HA/ccm) |
|---|---|---|---|---|---|
| Wild type | 0.312 | 4.845 | 63.988 | 0.145 | 703.189 |
| SD | 0.065 | 0.583 | 9.482 | 0.034 | 19.014 |
| Crtap-/- control | 0.084 | 2.130 | 38.888 | 0.450 | 677.416 |
| SD | 0.020 | 0.409 | 2.931 | 0.118 | 16.138 |
| Crtap-/- 1D11 | 0.280 | 4.290 | 64.650 | 0.171 | 746.862 |
| SD | 0.056 | 0.435 | 7.407 | 0.030 | 26.564 |
| ANOVA P value | <0.001 | <0.001 | <0.001+ | <0.001+ | <0.001 |
| Pairwise P values | | | | | |
| Wild type vs. Crtap-/- control | <0.001 | <0.001 | <0.05 | <0.05 | 0.023 |
| Wild type vs. Crtap-/- 1D11 | n.s. | 0.031 | n.s. | n.s. | <0.001 |
| Crtap-/- control vs. Crtap-/- 1D11 | <0.001 | <0.001 | <0.05 | <0.05 | <0.001 |

*Fig. 17*

|  | BV/TV (%) | Tb.N (1/mm) | Tb.Th (μm) | Tb.Sp (mm) | BMD BV (mg HA/ccm) |
|---|---|---|---|---|---|
| Wild type | 0.107 | 2.808 | 37.413 | 0.341 | 733.864 |
| SD | 0.036 | 0.684 | 5.071 | 0.108 | 25.997 |
| Crtap-/- control | 0.029 | 0.861 | 32.863 | 1.209 | 727.151 |
| SD | 0.011 | 0.237 | 3.428 | 0.345 | 28.765 |
| Crtap-/- 1D11 | 0.123 | 2.953 | 40.663 | 0.323 | 756.539 |
| SD | 0.045 | 0.767 | 5.842 | 0.121 | 36.913 |
| ANOVA P value | <0.001+ | <0.001+ | 0.015 | <0.001 | 0.162 |
| Pairwise P values |  |  |  |  |  |
| Wild type vs. Crtap-/- control | <0.05 | <0.05 | n.s. | <0.001 |  |
| Wild type vs. Crtap-/- 1D11 | n.s. | n.s. | n.s. | n.s. |  |
| Crtap-/- control vs. Crtap-/- 1D11 | <0.05 | <0.05 | 0.004 | <0.001 |  |

*Fig. 18*

|  | Cortical thickness (mm) | BMD BV (mg HA/ccm) | Diameter a.p. (mm) | CSA (mm²) | CSMI m.l. (mm⁴) | CSMI a.p. (mm⁴) |
|---|---|---|---|---|---|---|
| Wild type | 0.242 | 1084.726 | 1.239 | 0.905 | 0.134 | 0.221 |
| SD | 0.014 | 28.375 | 0.063 | 0.079 | 0.023 | 0.042 |
| Crtap⁻/⁻ control | 0.203 | 1084.885 | 1.142 | 0.731 | 0.101 | 0.162 |
| SD | 0.020 | 34.256 | 0.065 | 0.082 | 0.021 | 0.034 |
| Crtap⁻/⁻ 1D11 | 0.221 | 1096.127 | 1.186 | 0.808 | 0.111 | 0.186 |
| SD | 0.026 | 39.754 | 0.080 | 0.118 | 0.028 | 0.038 |
| ANOVA P value | 0.003 | 0.753 | 0.039 | 0.005 | 0.032 | 0.021 |
| Pairwise P values |  |  |  |  |  |  |
| Wild type vs. Crtap⁻/⁻ control | <0.001 |  | 0.012 | 0.001 | 0.011 | 0.006 |
| Wild type vs. Crtap⁻/⁻ 1D11 | n.s. |  | n.s. | n.s. | n.s. | n.s. |
| Crtap⁻/⁻ control vs. Crtap⁻/⁻ 1D11 | n.s. |  | n.s. | n.s. | n.s. | n.s. |

Fig. 19

| | Maximum load (N) | Stiffness (N/mm) | Energy to failure (N*mm) | Ultimate strength (MPa) | Toughness to failure (MPa) | Elastic modulus (GPa) | Total displacement (mm) | Elastic displacement (mm) | Post-yield displacement (mm) |
|---|---|---|---|---|---|---|---|---|---|
| Wild type | 22.831 | 230.578 | 7.846 | 154.704 | 11.912 | 6.960 | 0.444 | 0.068 | 0.376 |
| SD | 2.860 | 37.053 | 3.985 | 7.478 | 5.695 | 0.731 | 0.207 | 0.014 | 0.203 |
| Crtap-/- control | 12.943 | 151.689 | 1.228 | 114.496 | 2.208 | 6.663 | 0.127 | 0.079 | 0.048 |
| SD | 2.402 | 27.384 | 0.913 | 18.240 | 1.677 | 1.154 | 0.057 | 0.006 | 0.058 |
| Crtap-/- 1D11 | 18.818 | 200.804 | 1.991 | 145.633 | 3.408 | 7.248 | 0.156 | 0.073 | 0.083 |
| SD | 2.337 | 15.644 | 0.834 | 19.074 | 1.851 | 0.271 | 0.055 | 0.013 | 0.055 |
| ANOVA P value | <0.001 | 0.009 | 0.009 | 0.004 | 0.009 | 0.658 | 0.015 | 0.360 | 0.012 |
| Pairwise P values | | | | | | | | | |
| Wild type vs. Crtap-/- control | <0.001 | 0.003 | 0.005 | 0.001 | 0.005 | | 0.009 | | 0.007 |
| Wild type vs. Crtap-/- 1D11 | n.s. | n.s. | 0.017 | n.s. | 0.017 | | 0.023 | | 0.019 |
| Crtap-/- control vs. Crtap-/- 1D11 | 0.015 | n.s. | n.s. | 0.016 | n.s. | | n.s. | | n.s. |

Fig. 20

| | BV/TV (%) | Tb.N (1/mm) | Tb.Th (μm) | Tb.Sp (μm) | N.Oc/BS (1/mm) | Oc.S/BS (%) | N.Ob/BS (1/mm) | Ob.S/BS (%) | N.Ot/B.Ar (1/mm²) |
|---|---|---|---|---|---|---|---|---|---|
| Wild type | 11.956 | 4.003 | 29.554 | 226.736 | 3.226 | 15.051 | 18.142 | 20.827 | 549.002 |
| SD | 3.067 | 0.656 | 3.536 | 50.077 | 0.812 | 3.089 | 2.368 | 2.754 | 83.665 |
| Crtap-/- control | 3.817 | 1.909 | 19.502 | 587.008 | 4.768 | 19.885 | 24.487 | 26.888 | 735.561 |
| SD | 1.656 | 0.692 | 2.560 | 289.835 | 0.914 | 3.407 | 5.421 | 6.983 | 72.617 |
| Crtap-/- 1D11 | 10.203 | 3.411 | 30.182 | 277.886 | 1.772 | 6.829 | 8.638 | 9.748 | 565.044 |
| SD | 3.097 | 0.878 | 6.982 | 69.118 | 0.673 | 2.235 | 2.855 | 4.718 | 51.014 |
| ANOVA P value | <0.001 | <0.001 | 0.002 | 0.003+ | <0.001 | <0.001 | <0.001 | <0.001 | <0.001 |
| Pairwise P values | | | | | | | | | |
| Wild type vs. Crtap-/- control | <0.001 | <0.001 | 0.002 | <0.05 | 0.005 | 0.012 | 0.011 | n.s. | <0.001 |
| Wild type vs. Crtap-/- 1D11 | n.s. | n.s. | n.s. | n.s. | 0.007 | <0.001 | <0.001 | 0.002 | n.s. |
| Crtap-/- control vs. Crtap-/- 1D11 | <0.001 | 0.003 | 0.001 | <0.05 | <0.001 | <0.001 | <0.001 | <0.001 | <0.001 |

*Fig. 21*

|  | BV/TV (%) | Tb.N (1/mm) | Tb.Th (μm) | Tb.Sp (mm) | BMD BV (mg HA/ccm) |
|---|---|---|---|---|---|
| Wild type | 0.247 | 3.939 | 62.533 | 0.193 | 716.669 |
| SD | 0.033 | 0.330 | 3.497 | 0.025 | 7.626 |
| Col1α2tm1.1Mcbr control | 0.106 | 2.071 | 51.067 | 0.435 | 731.436 |
| SD | 0.015 | 0.195 | 2.999 | 0.047 | 11.792 |
| Col1α2tm1.1Mcbr 1D11 | 0.297 | 4.244 | 69.983 | 0.166 | 754.115 |
| SD | 0.020 | 0.199 | 2.329 | 0.013 | 7.844 |
| ANOVA P value | <0.001 | <0.001 | <0.001 | <0.001 | <0.001 |
| Pairwise P values |  |  |  |  |  |
| Wild type vs. Col1α2tm1.1Mcbr control | <0.001 | <0.001 | <0.001 | <0.001 | 0.015 |
| Wild type vs. Col1α2tm1.1Mcbr 1D11 | 0.002 | n.s. | <0.001 | n.s. | <0.001 |
| Col1α2tm1.1Mcbr control vs. Col1α2tm1.1Mcbr 1D11 | <0.001 | <0.001 | <0.001 | <0.001 | <0.001 |

Fig. 22

SEQUENCE LISTING

<160> NUMBER OF SEQ ID NOS: 25

<210> SEQ ID NO 1
<211> LENGTH: 390
<212> TYPE: PRT
<213> ORGANISM: Homo sapiens

<400> SEQUENCE: 1

```
Met Pro Pro Ser Gly Leu Arg Leu Leu Leu Leu Leu Pro Leu Leu
1               5                   10                  15

Trp Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
```

-continued

```
                245                 250                 255
Phe Leu Leu Leu Met Ala Thr Pro Leu Glu Arg Ala Gln His Leu Gln
                260                 265                 270

Ser Ser Arg His Arg Arg Ala Leu Asp Thr Asn Tyr Cys Phe Ser Ser
            275                 280                 285

Thr Glu Lys Asn Cys Cys Val Arg Gln Leu Tyr Ile Asp Phe Arg Lys
        290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
                340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
        370                 375                 380

Arg Ser Cys Lys Cys Ser
385                 390

<210> SEQ ID NO 2
<211> LENGTH: 414
<212> TYPE: PRT
<213> ORGANISM: Homo sapiens

<400> SEQUENCE: 2

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
                20                  25                  30

Met Arg Lys Arg Ile Glu Ala Ile Arg Gly Gln Ile Leu Ser Lys Leu
            35                  40                  45

Lys Leu Thr Ser Pro Pro Glu Asp Tyr Pro Glu Pro Glu Glu Val Pro
        50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
                100                 105                 110

Pro Ser Glu Asn Ala Ile Pro Pro Thr Phe Tyr Arg Pro Tyr Phe Arg
            115                 120                 125

Ile Val Arg Phe Asp Val Ser Ala Met Glu Lys Asn Ala Ser Asn Leu
        130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
        195                 200                 205

Glu Trp Leu His His Lys Asp Arg Asn Leu Gly Phe Lys Ile Ser Leu
    210                 215                 220
```

```
His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
            245                 250                 255

Ser Thr Tyr Thr Ser Gly Asp Gln Lys Thr Ile Lys Ser Thr Arg Lys
        260                 265                 270

Lys Asn Ser Gly Lys Thr Pro His Leu Leu Met Leu Leu Pro Ser
    275                 280                 285

Tyr Arg Leu Glu Ser Gln Gln Thr Asn Arg Arg Lys Lys Arg Ala Leu
        290                 295                 300

Asp Ala Ala Tyr Cys Phe Arg Asn Val Gln Asp Asn Cys Cys Leu Arg
305                 310                 315                 320

Pro Leu Tyr Ile Asp Phe Lys Arg Asp Leu Gly Trp Lys Trp Ile His
                325                 330                 335

Glu Pro Lys Gly Tyr Asn Ala Asn Phe Cys Ala Gly Ala Cys Pro Tyr
            340                 345                 350

Leu Trp Ser Ser Asp Thr Gln His Ser Arg Val Leu Ser Leu Tyr Asn
        355                 360                 365

Thr Ile Asn Pro Glu Ala Ser Ala Ser Pro Cys Cys Val Ser Gln Asp
370                 375                 380

Leu Glu Pro Leu Thr Ile Leu Tyr Tyr Ile Gly Lys Thr Pro Lys Ile
385                 390                 395                 400

Glu Gln Leu Ser Asn Met Ile Val Lys Ser Cys Lys Cys Ser
                405                 410

<210> SEQ ID NO 3
<211> LENGTH: 412
<212> TYPE: PRT
<213> ORGANISM: Homo sapiens

<400> SEQUENCE: 3

Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
                20                  25                  30

Gly His Ile Lys Lys Lys Arg Val Glu Ala Ile Arg Gly Gln Ile Leu
            35                  40                  45

Ser Lys Leu Arg Leu Thr Ser Pro Pro Glu Pro Thr Val Met Thr His
    50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Gly Cys Thr Gln Glu Asn Thr
                85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
        115                 120                 125

Ser Lys Val Phe Arg Phe Asn Val Ser Ser Val Glu Lys Asn Arg Thr
    130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190
```

```
Thr Arg Gly Thr Ala Glu Trp Leu Ser Phe Asp Val Thr Asp Thr Val
            195                 200                 205

Arg Glu Trp Leu Leu Arg Arg Glu Ser Asn Leu Gly Leu Glu Ile Ser
    210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
        275                 280                 285

Asp Asn Pro Gly Gln Gly Gly Gln Arg Lys Lys Arg Ala Leu Asp Thr
    290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Tyr Leu Arg
            340                 345                 350

Ser Ala Asp Thr Thr His Ser Thr Val Leu Gly Leu Tyr Asn Thr Leu
        355                 360                 365

Asn Pro Glu Ala Ser Ala Ser Pro Cys Cys Val Pro Gln Asp Leu Glu
    370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Asn Val Ile Ser
1               5

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Val Ile Pro Ile Val Asp Ile Ala Asn Tyr Ala Gln Arg Phe Lys
1               5                   10                  15

Gly

<210> SEQ ID NO 6
<211> LENGTH: 11
<212> TYPE: PRT
```

-continued

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Thr Leu Gly Leu Val Leu Asp Ala Met Asp Tyr
1               5                   10

<210> SEQ ID NO 7
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Arg Ala Ser Gln Ser Leu Gly Ser Ser Tyr Leu Ala
1               5                   10

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Ala Ser Ser Arg Ala Pro
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gln Gln Tyr Ala Asp Ser Pro Ile Thr
1               5

<210> SEQ ID NO 10
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60
```

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser
            115                 120

<210> SEQ ID NO 11
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys
            100                 105

<210> SEQ ID NO 12
<211> LENGTH: 327
<212> TYPE: PRT
<213> ORGANISM: Homo sapiens

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val

```
                    130                 135                 140
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 13
<211> LENGTH: 107
<212> TYPE: PRT
<213> ORGANISM: Homo sapiens

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 14
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14
```

-continued

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
    195                 200                 205

Pro Ser Asn Thr Lys Val Asp Lys Arg Val Glu Ser Lys Tyr Gly Pro
210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
```

His Asn His Tyr Thr Gln Lys Ser Leu Ser Leu Ser Leu Gly Lys
                435                 440                 445

<210> SEQ ID NO 15
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 16
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Met Gly Trp Ser Cys Ile Ile Leu Phe Leu Val Ala Thr Ala Thr Gly
1               5                   10                  15

Val His Ser

<210> SEQ ID NO 17
<211> LENGTH: 466

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Ser Ser Asn Val Ile Ser Trp Val Arg Gln Ala Pro Gly Gln Gly Leu
    50                  55                  60

Glu Trp Met Gly Gly Val Ile Pro Ile Val Asp Ile Ala Asn Tyr Ala
65                  70                  75                  80

Gln Arg Phe Lys Gly Arg Val Thr Ile Thr Ala Asp Glu Ser Thr Ser
                85                  90                  95

Thr Thr Tyr Met Glu Leu Ser Ser Leu Arg Ser Glu Asp Thr Ala Val
            100                 105                 110

Tyr Tyr Cys Ala Ser Thr Leu Gly Leu Val Leu Asp Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Ser Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
```

```
                 370                 375                 380
Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
                420                 425                 430

Lys Ser Arg Trp Gln Glu Gly Asn Val Phe Ser Cys Ser Val Met His
                435                 440                 445

Glu Ala Leu His Asn His Tyr Thr Gln Lys Ser Leu Ser Leu Ser Leu
                450                 455                 460

Gly Lys
465

<210> SEQ ID NO 18
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Gly Trp Ser Cys Ile Ile Leu Phe Leu Val Ala Thr Ala Thr Gly
1               5                   10                  15

Val His Ser Glu Thr Val Leu Thr Gln Ser Pro Gly Thr Leu Ser Leu
                20                  25                  30

Ser Pro Gly Glu Arg Ala Thr Leu Ser Cys Arg Ala Ser Gln Ser Leu
            35                  40                  45

Gly Ser Ser Tyr Leu Ala Trp Tyr Gln Gln Lys Pro Gly Gln Ala Pro
    50                  55                  60

Arg Leu Leu Ile Tyr Gly Ala Ser Ser Arg Ala Pro Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Tyr Ala
            100                 105                 110

Asp Ser Pro Ile Thr Phe Gly Gln Gly Thr Arg Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 19
```

```
<211> LENGTH: 16
<212> TYPE: PRT
<213> ORGANISM: Mus sp.
<220> FEATURE:
<221> NAME/KEY: MOD_RES
<222> LOCATION: (7)..(7)
<223> OTHER INFORMATION: hydroxylated Pro
<220> FEATURE:
<221> NAME/KEY: MOD_RES
<222> LOCATION: (12)..(12)
<223> OTHER INFORMATION: 3-hydroxylated Pro
<220> FEATURE:
<221> NAME/KEY: MOD_RES
<222> LOCATION: (13)..(13)
<223> OTHER INFORMATION: hydroxylated Pro

<400> SEQUENCE: 19

Asp Gly Leu Asn Gly Leu Pro Gly Pro Ile Gly Pro Pro Gly Pro Arg
1               5                   10                  15

<210> SEQ ID NO 20
<211> LENGTH: 16
<212> TYPE: PRT
<213> ORGANISM: Mus sp.
<220> FEATURE:
<221> NAME/KEY: MOD_RES
<222> LOCATION: (7)..(7)
<223> OTHER INFORMATION: hydroxylated Pro
<220> FEATURE:
<221> NAME/KEY: MOD_RES
<222> LOCATION: (13)..(13)
<223> OTHER INFORMATION: hydroxylated Pro

<400> SEQUENCE: 20

Asp Gly Leu Asn Gly Leu Pro Gly Pro Ile Gly Pro Pro Gly Pro Arg
1               5                   10                  15

<210> SEQ ID NO 21
<211> LENGTH: 16
<212> TYPE: PRT
<213> ORGANISM: Mus sp.
<220> FEATURE:
<221> NAME/KEY: MOD_RES
<222> LOCATION: (7)..(7)
<223> OTHER INFORMATION: hydroxylated Pro
<220> FEATURE:
<221> NAME/KEY: MOD_RES
<222> LOCATION: (13)..(13)
<223> OTHER INFORMATION: hydroxylated Pro

<400> SEQUENCE: 21

Asp Gly Leu Asn Gly Leu Pro Gly Pro Ile Gly Pro Pro Gly Pro Arg
1               5                   10                  15

<210> SEQ ID NO 22
<211> LENGTH: 123
<212> TYPE: PRT
<213> ORGANISM: Homo sapiens

<400> SEQUENCE: 22

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser
            115                 120
```

<210> SEQ ID NO 23
<211> LENGTH: 107
<212> TYPE: PRT
<213> ORGANISM: Homo sapiens

<400> SEQUENCE: 23

```
Glu Ile Val Leu Thr Gln Ser Pro Ser Ser Leu Ser Ala Ser Val Gly
 1               5                  10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Ile Leu Leu Ile
        35                  40                  45

Tyr Gly Thr Ser Thr Leu Gln Ser Gly Val Pro Ser Arg Phe Ser Gly
50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys Leu Gln Asp Ser Asn Tyr Pro Leu
                 85                  90                  95

Thr Phe Gly Gly Gly Thr Arg Leu Glu Ile Lys
            100                 105
```

<210> SEQ ID NO 24
<211> LENGTH: 115
<212> TYPE: PRT
<213> ORGANISM: Homo sapiens

<400> SEQUENCE: 24

```
Glu Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Tyr Cys
                 85                  90                  95

Gly Arg Thr Leu Glu Ser Ser Leu Trp Gly Gln Gly Thr Leu Val Thr
            100                 105                 110

Val Ser Ser
        115
```

<210> SEQ ID NO 25
<211> LENGTH: 110
<212> TYPE: PRT
<213> ORGANISM: Homo sapiens

<400> SEQUENCE: 25

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Ser Thr His
                85                  90                  95

Arg Gly Val Phe Gly Gly Gly Thr Lys Leu Thr Val Leu Gly
                100                 105                 110
```

METHODS FOR TREATING OSTEOGENESIS IMPERFECTA

CROSS-REFERENCE TO RELATED APPLICATIONS

This application is a continuation of U.S. patent application Ser. No. 16/459,023, filed Jul. 1, 2019, now U.S. Pat. No. 11,230,595, which is a continuation of U.S. patent application Ser. No. 15/427,920, filed Feb. 8, 2017, now U.S. Pat. No. 10,377,819, issued Aug. 13, 2019, which is a continuation of U.S. patent application Ser. No. 14/772,708, filed Sep. 3, 2015, now U.S. Pat. No. 9,598,486, issued Mar. 21, 2017, which is a 35 U.S.C. § 371 National Stage filing of International Patent Application PCT/US2014/031279, filed Mar. 20, 2014, which claims priority to U.S. Provisional Patent Application 61/803,647, filed Mar. 20, 2013, U.S. Provisional Patent Application 61/875,399, filed Sep. 9, 2013, and U.S. Provisional Patent Application 61/883,151, filed Sep. 26, 2013. The contents of each of the aforementioned priority applications are incorporated herein by reference in their entirety.

GOVERNMENT FUNDING

This invention was made with government support under P01 HD070394, P01 HD022657 & R01 DE017713 awarded by the National Institutes of Health. The government has certain rights in the invention.

SEQUENCE LISTING

The instant application contains a Sequence Listing that has been submitted electronically in ASCII format and is hereby incorporated by reference in its entirety. The ASCII copy, created on Dec. 8, 2021, is named 022548_C3018_SL.txt and is 36,652 bytes in size.

FIELD OF THE INVENTION

The present invention relates to methods for treating osteogenesis imperfecta (OI). More specifically, the invention relates to methods for treating OI using a binding protein, e.g., an antibody or antigen-binding fragment thereof, which specifically binds to human transforming growth factor beta (TGFβ) or isoforms thereof.

BACKGROUND OF THE INVENTION

Osteogenesis imperfecta (OI), also known as "brittle bone disease" or Lobstein syndrome, is a debilitating and rare congenital bone disease that affects about one in every 15,000 people. Though phenotypes vary among OI types, common symptoms include incomplete ossification of bones and teeth, reduced bone mass, brittle bones, and pathologic fractures. These common symptoms of OI are thought to be caused by gene mutations which result in deficiencies in Type-I collagen or other proteins involved in bone matrix deposition or homeostasis. As a result of these symptoms and the propensity for fatal bone fractures and complications, life expectancy of OI patients is reduced as compared to the general population. Accordingly, there clearly exists an urgent need in the art to develop effective treatments for OI.

BRIEF DESCRIPTION OF THE FIGURES

FIGS. 7A and 7B (micrograph images) and 7C (graph) demonstrate the lung phenotype of Crtap$^{-/-}$ mice treated with the mouse pan-specific anti-TGFβ antibody 1D11.

FIGS. 10A-F are a group of graphs, photos, and images that show increased TGFβ signaling in Crtap$^{-/-}$ mice. FIG. 10A is a series of three graphs that show the results of quantitative RT-PCR of TGFβ target genes p21, PAI-1, and Col1a1. The graphs indicate increased TGFβ signaling in calvarial bone of P3 WT and Crtap$^{-/-}$ mice. Results are shown as fold change of the mean of WT group±SD; n=5 per group, *p<0.05. FIG. 10B is a photograph of a Western blot analysis of P3 calvarial protein extracts, which shows increased amounts of activated Smad2 (pSmad2) relative to total Smad2 protein in Crtap$^{-/-}$ versus WT mice, suggesting increased TGFβ-signaling; n=3 per group. FIG. 10C is a graph showing the quantification of the Western blot shown in FIG. 10B. Results are shown as fold change of the mean of WT group±SD, *p<0.05. FIG. 10D is an image showing increased bioluminescence in regions that overlap with skeletal structures in Crtap$^{-/-}$ compared with WT mice that were intercrossed to TGFβ-reporter mice (SBE-Luc mice). Representative image of 3 litters at P10 is shown. In 3 litters Crtap$^{-/-}$ mice show a mean 2.86 fold (SD±0.34) bioluminescence signal at the head/calvaria compared with WT mice (scale bar=1 cm). FIG. 10E is a graph that shows, using a TGFβ reporter cell line, TGFβ activity was assessed in conditioned medium from WT and Crtap$^{-/-}$ bone marrow stromal cells cultured under osteogenic conditions for 3 days, demonstrating greater TGFβ activity compared with the medium from WT cells. Results are shown as fold change of the mean of WT group±SD, n=5 per group, *p<0.05. FIG. 10F is two pictures showing immunostaining of lungs (P10) for pSmad2, which shows increased intracellular staining in WT and Crtap$^{-/-}$ mice (40× magnification). Representative images of n=3 mice per group are shown (scale bar=20 μm).

FIG. 11A is a series of three MicroCT images of L4 vertebral bodies of 16-week-old wildtype (WT), control antibody-treated Crtap$^{-/-}$, and 1D11-treated Crtap$^{-/-}$ mice after treatment for 8 weeks. FIG. 11B is a group of three graphs showing the results of MicroCT of L4 vertebral bodies, which demonstrates increased bone volume/total volume (BV/TV), trabecular number (Tb.N), and thickness (Tb.Th) in WT, control Crtap$^{-/-}$ and 1D11 treated Crtap$^{-/-}$ mice. Results are shown as means±SDs, n=8 per group, *p<0.05 for Crtap$^{-/-}$ 1 D11 vs. Crtap$^{-/-}$ control, +p<0.05 for Crtap$^{-/-}$ vs. WT. FIG. 11C is a group of three graphs showing the results of histomorphometric analysis of L4 vertebrae, which shows increased osteoclast (N.Oc/BS) and osteoblast (N.Ob/BS) numbers per bone surface in Crtap$^{-/-}$ mice compared with WT. Reduced osteoblast and osteoclast numbers after treatment with 1D11 indicates effective suppression of accelerated bone remodeling in Crtap$^{-/-}$ mice. Increased numbers of osteocytes per bone area (N.Ot/B.Ar) in Crtap$^{-/-}$ mice are reduced to WT level after 1D11 treatment. Results are shown as means±SDs, n=6 per group, *p<0.05 for Crtap$^{-/-}$ 1 D11 vs. Crtap$^{-/-}$ control, +p<0.05 for Crtap$^{-/-}$ vs. WT. FIG. 11D is a series of three pictures showing hematoxylin/eosin staining of inflated lungs of 16-week-old wildtype (WT), control Crtap$^{-/-}$, and 1D11-treated Crtap$^{-/-}$ mice after treatment for 8 weeks. Crtap$^{-/-}$ control mice show an increase in distal airway space compared with WT mice. After treatment with 1D11, there is a reduction of the distal airway diameter compared with control Crtap$^{-/-}$ mice. Representative images of n=8 mice per group are shown (scale bar=100 μm).

FIG. 12A is a group of three graphs that show the results of quantitative RT-PCR of calvarial bone of P3 mice, which shows no difference in RNA expression of the small leucine-rich proteoglycans decorin (Dcn), biglycan (Bgn), and asporin (Aspn) in calvarial bone of Crtap$^{-/-}$ mice compared with WT. Results are given as fold change of the mean of WT group±SD, n=5 per group. FIG. 12B is a graph that shows the results of surface plasmon resonance analysis, which indicates that binding of recombinant decorin core protein to type I collagen of Crtap$^{-/-}$ mice is approximately 45% less compared with WT type I collagen. Three independent experiments using 3, 5, and 12 μM of decorin were performed. Response units (RU) of total amount decorin bound normalized to type I collagen immobilized on the chip are shown. Mean reduction of decorin binding to Crtap$^{-/-}$ type I collagen is 44.6±7.9%.

FIGS. 13A-E are a series of graphs and photos showing inhibition of increased TGFβ signaling improves the bone phenotype in a mouse model of dominant OI resulting from a G610C mutation in the Col1a2 gene (Col1a2$^{tm1.1Mcbr}$). FIG. 13A is two graphs showing the results of quantitative RT-PCR of TGFβ target genes p21 and PAI-1, which indicates increased TGFβ signaling in calvarial bone of P3 WT and Col1a2$^{tm1.1Mcbr}$ mice. Results are shown as fold change of the mean of WT group±SD; n=3 per group, *p<0.05. FIG. 13B is a photo of the results of Western blot analysis, which shows increased levels of activated Smad2 (pSmad2) relative to total levels of Smad2 protein in P3 calvaria of WT and Col1a2$^{tm1.1Mcbr}$ mice compared with WT, suggesting increased TGFβ-signaling; n=3 per group. FIG. 13C is a graph showing the quantification of the Western blot seen in FIG. 13B. Results are shown as fold change of the mean of WT group±SD; *p<0.05. FIG. 13D are a series of photos of MicroCT images of L4 vertebral bodies of 16-week-old wildtype (WT), control antibody-treated Col1a2$^{tm1.1Mcbr}$ and 1D11-treated Col1a2$^{tm1.1Mcbr}$ mice after treatment for 8 weeks. FIG. 13E is a series of graphs of data from MicroCT of L4 vertebral bodies, which shows increased bone volume/total volume (BV/TV), trabecular number (Tb.N) and thickness (Tb.Th) in Col1a2$^{tm1.1Mcbr}$ mice after treatment with 1D11. Results are shown as means±SDs, n=6 per group, *p<0.05 for Col1a2$^{tm1.1Mcbr}$ 1D11 vs. Col1a2$^{tm1.1Mcbr}$ control, +p<0.05 for Col1a2$^{tm1.1Mcbr}$ vs. WT.

FIG. 15A is a series of three graphs showing tandem mass spectra of extracted type I collagen from tibia of WT, control Crtap$^{-/-}$, and 1D11-treated Crtap$^{-/-}$ mice (16 week old mice, after treatment for 8 weeks). The sequence in the top graph is SEQ ID NO: 19, the sequence in the middle graph is SEQ ID NO: 20, and the sequence in the bottom graph is SEQ ID NO: 21. FIG. 15B is a table showing a summary of tandem mass spectra analyses. 1D11 treatment did not significantly affect 3-hydroxylation status of collagen residue Pro986 alpha 1(I) in bone samples. Mean of percentage of 3-hydroxylated residues (±SD) is shown, n=5 per group. FIG. 15C is a group of three graphs showing that bone type I collagen of control Crtap$^{-/-}$ and 1D11-treated Crtap$^{-/-}$ mice exhibit changes in hydroxylysyl pyridinoline (HP) and lysyl pyridinoline crosslinks (LP) levels and an increased HP/LP ratio compared with WT mice. 1D11 treatment of Crtap$^{-/-}$ mice did not significantly affect these parameters compared to control Crtap$^{-/-}$ mice. Results are given as means±SDs, n=4 mice per group, +p<0.05 for Crtap$^{-/-}$ vs. WT.

FIG. 16A is two graphs showing increased OCN and CTX serum levels in 8 week old Crtap$^{-/-}$ compared with WT mice at the start of the study indicate increased bone turnover in Crtap$^{-/-}$ mice. Results are given as means±SDs, n=8 for WT, n=14 for Crtap$^{-/-}$ mice, +p<0.05 for Crtap$^{-/-}$ vs. WT. FIG. 16B is two graphs that show that at 16 weeks of age 1D11-treated Crtap$^{-/-}$ mice show a trend to reduced serum OCN and significantly reduced CTX serum levels compared with control Crtap$^{-/-}$ mice, indicating a suppression of increased bone turnover by inhibition of TGFβ. Results are given as means±SDs, n=8 for WT, n=7 per Crtap$^{-/-}$ group; *p<0.05 for Crtap$^{-/-}$ 1 D11 vs. Crtap$^{-/-}$ control, +p<0.05 for Crtap$^{-/-}$ vs. WT.

FIG. 17 is a table showing the results of MicroCT analyses of vertebral body L4 of WT, control Crtap$^{-/-}$, and 1D11 treated Crtap$^{-/-}$ mice (16 week old mice, after treatment for 8 weeks). Means±SDs are shown for bone volume/tissue volume (BV/TV), trabecular number (Tb.N), trabecular thickness (Tb.Th), trabecular separation (Tb.Sp), and bone mineral density of bone volume (BMD BV); n=8 per group, + indicates Kruskal-Wallis one-way ANOVA on ranks where the equal variance test failed. n.s.=not statistically significant.

FIG. 18 is a table showing the results of MicroCT analyses of trabecular bone in proximal femurs for WT, control Crtap$^{-/-}$, and 1D11-treated Crtap$^{-/-}$ mice (16 week old mice, after treatment for 8 weeks). Means±SDs are shown for bone volume/tissue volume (BV/TV), trabecular number (Tb.N), trabecular thickness (Tb.Th), trabecular separation (Tb.Sp), and bone mineral density of bone volume (BMD BV); n=8 per group. + indicates Kruskal-Wallis one-way ANOVA on ranks where the equal variance test failed. n.s.=not statistically significant.

FIG. 19 is a table showing the results of MicroCT analysis of cortical bone at the femur midshaft for WT, control Crtap$^{-/-}$, and 1D11-treated Crtap$^{-/-}$ mice (16 week old mice, after treatment for 8 weeks). Means±SDs are shown for cortical thickness, bone mineral density of bone volume (BMD BV), anterior-posterior (a.p.) diameter, cross-sectional area (CSA), and cross-sectional moments of inertia (CSMI) for medio-lateral (m.1.) and anterior-posterior (a.p.) axis; n=8 per group. n.s.=not statistically significant.

FIG. 20 is a table showing the results of biomechanical testing of femurs by 3-point bending (16 week old mice, after treatment for 8 weeks). Compared with WT mice, control Crtap$^{-/-}$ mice exhibit significantly reduced biomechanical parameters except elastic modulus and elastic displacement. Anti TGFβ-treatment with 1D11 resulted in significant improvements of maximum load and ultimate strength in Crtap$^{-/-}$ femurs, indicating increased whole bone and tissue strength. However, no significant changes in post-yield displacement were observed, indicating that 1D11 did not affect the increased brittleness of the OI bone. N=6 for WT, n=4 for control Crtap$^{-/-}$ and n=3 for 1D11 treated Crtap$^{-/-}$ mice. n.s.=not statistically significant.

FIG. 21 is a table showing the results of histomorphometry analyses of L4 vertebral bodies of WT, control Crtap$^{-/-}$, and 1D11-treated Crtap$^{-/-}$ mice (16 week old mice, after treatment for 8 weeks). Means±SDs are shown for bone volume/tissue volume (BV/TV), trabecular number (Tb.N), trabecular thickness (Tb.Th), trabecular separation (Tb.Sp), number of osteoclasts/bone surface (N.Oc/BS), osteoclast surface/bone surface (Oc.S/BS), number of osteoblasts/bone surface (N.Ob/BS), osteoblast surface/bone surface (Oc.S/BS), and number of osteocytes/bone area (N.Ot/B.Ar); n=6 per group. + indicates Kruskal-Wallis one way ANOVA on ranks where equal variance test failed. n.s.=not statistically significant.

FIG. 22 is a table showing the results of MicroCT analyses of vertebral body L4 of WT, control Col1a2$^{tm1.1Mcbr}$ and 1D11 treated Col1a2$^{tm1.1Mcbr}$ mice (16 week old mice, after treatment for 8 weeks). Means±SDs are shown for bone volume/tissue volume (BV/TV), trabecular number (Tb.N), trabecular thickness (Tb.Th), trabecular separation (Tb.Sp), and bone mineral density of bone volume (BMD BV); n=6 per group, n.s.=not statistically significant.

SUMMARY OF THE INVENTION

Figure 1A:
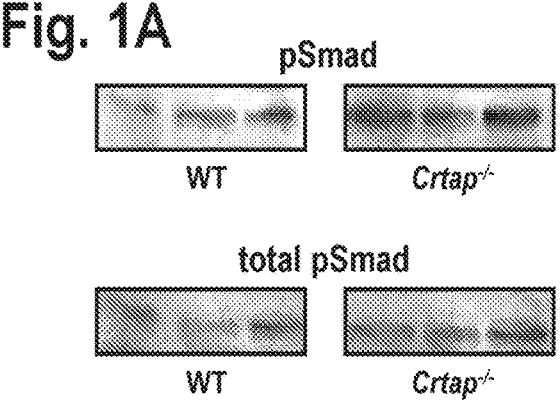
FIGS. 1A (Western blot) and 1B-1F (graphs) demonstrate that TGFβ signaling is elevated in bones from Crtap$^{-/-}$ mice, as compared to wild type controls.

The present invention relates to methods for effectively treating osteogenesis imperfecta (OI). More specifically, the invention relates to methods for treating OI using a binding protein such as antibody or an antigen-binding fragment thereof that specifically binds to transforming growth factor beta (TGFβ) or an isoform thereof. Preferably, the binding protein is "pan-specific" and binds to all three human isoforms of TGFβ, i.e., TGFβ1, TGFβ2, and TGFβ3. More preferably, the binding protein specifically binds to and neutralizes human TGFβ1, TGFβ2, and TGFβ3. In one aspect, the invention provides a method for treating OI in a subject in need thereof comprising administering to the subject a therapeutically effective amount of an antibody or an antigen-binding fragment thereof that specifically binds to TGFβ.

In one embodiment, the antibody or antigen-binding fragment thereof comprises a heavy chain variable region comprising three complementarity determining regions (CDRs) having amino acid sequences selected from the group consisting of SEQ ID NOs: 4, 5, and 6; and a light chain variable region comprising three CDRs having amino acid sequences selected from the group consisting of SEQ ID NOs: 7, 8, and 9.

In another embodiment, the antibody or antigen-binding fragment thereof comprises a heavy chain variable region comprising the amino acid sequence of SEQ ID NO: 10, and a light chain variable region comprising the amino acid sequence of SEQ ID NO: 11.

In one embodiment, the antibody or antigen-binding fragment thereof further comprises a human IgG4 constant region. In one embodiment, the human IgG4 constant region comprises the amino acid sequence of SEQ ID NO: 12. In another embodiment, the antibody or antigen-binding fragment thereof further comprises a human κ light chain constant region. In another embodiment, the human κ light chain constant region comprises the amino acid sequence of SEQ ID NO: 13. In another embodiment, the antibody or antigen-binding fragment thereof further comprises a human IgG4 constant region, and a human κ light chain constant region.

In another embodiment, the human IgG4 constant region comprises the amino acid sequence of SEQ ID NO: 12, and the human κ light chain constant region comprises the amino acid sequence of SEQ ID NO: 13. In another embodiment, the antibody comprises a heavy chain comprising the amino acid sequence of SEQ ID NO: 14. In another embodiment, the antibody comprises a light chain comprising the amino acid sequence of SEQ ID NO: 15. In another embodiment, the antibody comprises a heavy chain comprising the amino acid sequence of SEQ ID NO: 14, and a light chain comprising the amino acid sequence of SEQ ID NO: 15.

In another embodiment, the antibody or antigen-binding fragment thereof binds to human TGFβ1, TGFβ2, and TGFβ3. In another embodiment, the antibody or antigen-binding fragment thereof neutralizes human TGFβ1, TGFβ2, and TGFβ3.

In another embodiment, the antibody or antigen-binding fragment thereof improves a bone parameter selected from the group consisting of bone volume density (BV/TV), total bone surface (BS), bone surface density (BS/BV), trabecular number (Tb.N), trabecular thickness (Tb.Th), trabecular spacing (Tb. Sp), and total volume (Dens TV).

In another embodiment, the antibody or antigen-binding fragment thereof inhibits bone resorption.

In another embodiment, the antibody or antigen-binding fragment thereof reduces a serum biomarker of bone resorption selected from the group consisting of urinary hydroxyproline, urinary total pyridinoline (PYD), urinary free deoxypyridinoline (DPD), urinary collagen type-I cross-linked N-telopeptide (NTX), urinary or serum collagen type-I cross-linked C-telopeptide (CTX), bone sialoprotein (BSP), osteopontin (OPN), and tartrate-resistant acid phosphatase 5b (TRAP).

In another embodiment, the antibody or antigen-binding fragment thereof increases a serum biomarker of bone deposition selected from the group consisting of as total alkaline phosphatase, bone-specific alkaline phosphatase, osteocalcin, and type-I procollagen (C-terminal/N-terminal).

In another embodiment, the antibody or antigen-binding fragment thereof inhibits bone resorption. In another embodiment, the antibody or antigen-binding fragment thereof promotes bone deposition. In another embodiment, the antibody or antigen-binding fragment thereof improves the function of a non-skeletal organ affected by OI selected from the group consisting of hearing function, lung function, and kidney function.

In another aspect, the invention provides a method for treating OI in a subject in need thereof comprising administering to the subject a therapeutically effective amount of an antibody or an antigen-binding fragment thereof that binds to TGFβ, wherein the antibody comprises a heavy chain comprising the amino acid sequence of SEQ ID NO: 14, and a light chain comprising the amino acid sequence of SEQ ID NO: 15.

In another aspect, the invention provides a method for treating OI in a subject in need thereof comprising administering to the subject a therapeutically effective amount of an antibody or an antigen-binding fragment thereof that binds to TGFβ in combination with at least one therapeutic agent. In another embodiment, the agent is a bisphosphonate.

DETAILED DESCRIPTION OF THE INVENTION

A. Definitions

Unless defined otherwise, all technical and scientific terms used herein have the same meaning as is commonly understood by one of ordinary skill in the art.

It is noted here that as used in this specification and the appended claims, the singular forms "a", "an", and "the" also include plural reference, unless the context clearly dictates otherwise.

The term "about" or "approximately" means within 10%, and more preferably within 5% (or 1% or less), of a given value or range.

The terms "administer" or "administration" refer to the act of injecting or otherwise physically delivering a substance as it exists outside the body (e.g., an antibody) into a patient, such as by mucosal, intradermal, intravenous, subcutaneous, intramuscular delivery, and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

An "antagonist" or "inhibitor" of TGFβ refers to a molecule that is capable of inhibiting or otherwise decreasing one or more of the biological activities of TGFβ, such as in a cell expressing TGFβ or in a cell expressing a TGFβ ligand, or expressing a TGFβ receptor. In certain exemplary embodiments, antibodies of the invention are antagonist antibodies that inhibit or otherwise decrease the activity of TGFβ in a cell having a cell surface-expressed TGFβ receptor (e.g., TGFβ receptor 1, 2, or 3) when said antibody is contacted with said cell. In some embodiments, an antagonist of TGFβ (e.g., an antibody of the invention) may, for example, act by inhibiting or otherwise decreasing the activation and/or cell signaling pathways of the cell expressing a TGFβ receptor, thereby inhibiting a TGFβ-mediated biological activity of the cell relative to the TGFβ-mediated biological activity in the absence of antagonist. In certain embodiments of the invention, the anti-TGFβ antibodies are antagonistic anti-TGFβ antibodies, preferably fully human, monoclonal, antagonistic anti-TGFβ antibodies.

The terms "antibody", "immunoglobulin", or "Ig" may be used interchangeably herein. The term antibody includes, but is not limited to, synthetic antibodies, monoclonal antibodies, recombinantly produced antibodies, multispecific antibodies (including bispecific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies include immunoglobulin molecules and immunologically active portions of immunoglobulin molecules, i.e., antigen-binding domains or molecules that contain an antigen-binding site that specifically binds to a TGFβ antigen (e.g., one or more complementarity determining regions (CDRs) of an anti-TGFβ antibody). The anti-TGFβ antibodies can be of any type (e.g., IgG, IgE, IgM, IgD, IgA, and IgY), any class (e.g., IgG1, IgG2, IgG3, IgG4, IgA1, and IgA2), or any subclass (e.g., IgG2a and IgG2b) of an immunoglobulin molecule. In certain embodiments, the anti-TGFβ antibodies are humanized, such as humanized monoclonal anti-TGFβ antibodies. In other embodiments, the anti-TGFβ antibodies are fully human, such as fully human monoclonal anti-TGFβ antibodies. In preferred embodiments, the anti-TGFβ antibodies are IgG antibodies, such as IgG4 antibodies.

The terms "composition" and "formulation" are intended to encompass a product containing specified ingredients (e.g., an anti-TGFβ antibody) in, optionally, specified amounts, as well as any product which results, directly or indirectly, from the combination of specified ingredients in, optionally, specified amounts.

The terms "constant region" or "constant domain" refer to a carboxy terminal portion of the light and heavy chain that is not directly involved in binding of the antibody to antigen, but exhibits various effector functions, such as interaction with the Fc receptor. The terms refer to the portion of an immunoglobulin molecule having a more conserved amino acid sequence relative to the other portion of the immunoglobulin, the variable domain, which contains the antigen-binding site. The constant domain contains the CH1, CH2, and CH3 domains of the heavy chain, and the CHL domain of the light chain.

The term "epitope" refers to a localized region on the surface of an antigen, such as a TGFβ polypeptide or TGFβ polypeptide fragment, that is capable of being bound to one or more antigen-binding regions of an antibody, and that has antigenic or immunogenic activity in an animal, preferably a mammal, and most preferably in a human, that is capable of eliciting an immune response. An epitope having immunogenic activity is a portion of a polypeptide that elicits an antibody response in an animal. An epitope having antigenic activity is a portion of a polypeptide to which an antibody specifically binds, as determined by any method well known in the art, for example, such as an immunoassay. Antigenic epitopes need not necessarily be immunogenic. Epitopes usually consist of chemically active surface groupings of molecules, such as amino acids or sugar side chains, and have specific three-dimensional structural characteristics, as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a TGFβ epitope is a three-dimensional surface feature of a TGFβ polypeptide (e.g., in a trimeric form of a TGFβ polypeptide). In other embodiments, a TGFβ epitope is a linear feature of a TGFβ polypeptide (e.g., in a dimeric form or monomeric form of the TGFβ polypeptide). Anti-TGFβ antibodies may specifically bind to an epitope of the monomeric form of TGFβ, an epitope of the dimeric form of TGFβ, or both the monomeric form and the dimeric form of TGFβ.

The term "excipients" refers to inert substances that are commonly used as a diluent, vehicle, preservative, binder, stabilizing agent, etc. for drugs and includes, but is not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, Remington's Pharmaceutical Sciences (1990) Mack Publishing Co., Easton, Pa., which is hereby incorporated by reference in its entirety.

In the context of a peptide or polypeptide, the term "fragment" refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, TGFβ fragments include polypeptides comprising an amino acid sequence of at least 50, at 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a TGFβ polypeptide. In a specific embodiment, a fragment of a TGFβ polypeptide or an antibody that specifically binds to a TGFβ antigen retains at least 1, at least 2, or at least 3 functions of the full-length polypeptide or antibody.

The terms "fully human antibody" or "human antibody" are used interchangeably herein and refer to an antibody that comprises a human variable region and, most preferably a human constant region. In specific embodiments, the terms refer to an antibody that comprises a variable region and constant region of human origin. "Fully human" anti-TGFβ antibodies, in certain embodiments, can also encompass antibodies that bind TGFβ polypeptides and are encoded by nucleic acid sequences that are naturally occurring somatic variants of a human germline immunoglobulin nucleic acid sequence. In a specific embodiment, the anti-TGFβ antibodies are fully human antibodies. The term "fully human antibody" includes antibodies having variable and constant regions corresponding to human germline immunoglobulin sequences as described by Kabat et al. (See Kabat et al. (1991) Sequences of Proteins of Immunological Interest, Fifth Edition, U.S. Department of Health and Human Services, NIH Publication No. 91-3242). Methods of producing fully human antibodies are known in the art.

The phrase "recombinant human antibody" includes human antibodies that are prepared, expressed, created, or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see, e.g., Taylor, L. D. et al. (1992) Nucl Acids Res. 20:6287-6295) or antibodies prepared, expressed, created, or isolated by any other means that involves splicing of human immunoglobulin gene sequences to other DNA sequences. Such recombinant human antibodies can have variable and constant regions derived from human germline immunoglobulin sequences (See Kabat, E. A. et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "heavy chain" when used in reference to an antibody refers to five distinct types, called alpha (α), delta (Δ), epsilon (ε), gamma (γ) and mu (μ), based on the amino acid sequence of the heavy chain constant domain. These distinct types of heavy chains are well known in the art and give rise to five classes of antibodies, IgA, IgD, IgE, IgG, and IgM, respectively, including four subclasses of IgG, namely IgG1, IgG1, IgG3, and IgG4. Preferably the heavy chain is a human heavy chain.

An "isolated" or "purified" antibody is substantially free of cellular material or other contaminating proteins from the cell or tissue source from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). When the antibody is recombinantly produced, it is also preferably substantially free of culture medium, i.e., culture medium represents less than about 20%, 10%, or 5% of the volume of the protein preparation. When the antibody is produced by chemical synthesis, it is preferably substantially free of chemical precursors or other chemicals, i.e., it is separated from chemical precursors or other chemicals that are involved in the synthesis of the protein. Accordingly, such preparations of the antibody have less than about 30%, 20%, 10%, 5% (by dry weight) of chemical precursors or compounds other than the antibody of interest. In a preferred embodiment, anti-TGFβ antibodies are isolated or purified.

The terms "Kabat numbering," and like terms are recognized in the art and refer to a system of numbering amino acid residues that are more variable (i.e. hypervariable) than other amino acid residues in the heavy and light chain variable regions of an antibody, or an antigen-binding portion thereof (Kabat et al. (1971) Ann. NY Acad. Sci. 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3. For the light chain variable region, the hypervariable region typically ranges from amino acid positions 24 to 34 for CDR1, amino acid positions 50 to 56 for CDR2, and amino acid positions 89 to 97 for CDR3.

The term "light chain" when used in reference to an antibody refers to two distinct types, called kappa (κ) of lambda (λ), based on the amino acid sequence of the constant domains. Light chain amino acid sequences are well known in the art. In preferred embodiments, the light chain is a human light chain.

The terms "manage", "managing", and "management" refer to the beneficial effects that a subject derives from a therapy (e.g., a prophylactic or therapeutic agent), which does not result in a cure of the disease or disorder. In certain embodiments, a subject is administered one or more therapies (e.g., prophylactic or therapeutic agents) to "manage" a TGFβ-mediated disease (e.g., OI), or one or more symptoms thereof, so as to prevent the progression or worsening of the disease.

The term "monoclonal antibody" refers to an antibody obtained from a population of homogenous or substantially homogeneous antibodies, and each monoclonal antibody will typically recognize a single epitope on the antigen. In preferred embodiments, a "monoclonal antibody" is an antibody produced by a single hybridoma or other cell. The term "monoclonal" is not limited to any particular method for making the antibody. For example, monoclonal antibodies may be made by the hybridoma method as described in Kohler et al.; Nature, 256:495 (1975) or may be isolated from phage libraries. Other methods for the preparation of clonal cell lines and of monoclonal antibodies expressed thereby are well known in the art (see, for example, Chapter 11 in: Short Protocols in Molecular Biology, (2002) 5th Ed.; Ausubel et al., eds., John Wiley and Sons, New York).

The term "pharmaceutically acceptable" means being approved by a regulatory agency of the Federal or a State government or listed in the U.S. Pharmacopeia, European Pharmacopeia, or other generally recognized Pharmacopeia for use in animals, and more particularly in humans.

The term "pharmaceutically acceptable excipient" means any inert substance that is combined with an active molecule, such as a monoclonal antibody, for preparing an agreeable or convenient dosage form. The "pharmaceutically acceptable excipient" is an excipient that is non-toxic to recipients at the dosages and concentrations employed, and is compatible with other ingredients of the formulation comprising the monoclonal antibody.

The terms "prevent", "preventing", and "prevention" refer to the total or partial inhibition of the development, recurrence, onset, or spread of a TGFβ-mediated disease and/or symptom related thereto, resulting from the administration of a therapy or combination of therapies provided herein (e.g., a combination of prophylactic or therapeutic agents).

The term "TGFβ antigen" refers to that portion of a TGFβ polypeptide to which an antibody specifically binds. A TGFβ antigen also refers to an analog or derivative of a TGFβ polypeptide or fragment thereof to which an antibody specifically binds. In some embodiments, a TGFβ antigen is a monomeric TGFβ antigen or a dimeric TGFβ antigen. A region of a TGFβ polypeptide contributing to an epitope may be contiguous amino acids of the polypeptide, or the epitope may come together from two or more non-contiguous regions of the polypeptide. The epitope may or may not be a three-dimensional surface feature of the antigen. A localized region on the surface of a TGFβ antigen that is capable of eliciting an immune response is a TGFβ epitope. The epitope may or may not be a three-dimensional surface feature of the antigen. As used herein, an "analog" of the TGFβ antigen refers to a polypeptide that possesses a similar or identical function as a TGFβ polypeptide, a fragment of a TGFβ polypeptide, or a TGFβ epitope described herein. For example, the analog may comprise a sequence that is at least 80%, at least 85%, at least 90%, at least 95%, or at least 99% identical to the amino acid sequence of a TGFβ polypeptide (e.g., SEQ ID NO: 1, 2, or 3), a fragment of a TGFβ polypeptide, a TGFβ epitope, or an anti-TGFβ antibody described herein. Additionally or alternatively, the polypeptide is encoded by a nucleotide sequence that hybridizes under stringent conditions to a nucleotide sequence encoding a TGFβ polypeptide, a fragment of a TGFβ polypeptide, or a TGFβ epitope described herein The term "human TGFβ," "hTGFβ," or "hTGFβ polypeptide" and similar terms refer to the polypeptides ("polypeptides," "peptides," and "proteins" are used interchangeably herein) comprising the amino acid sequence of SEQ ID NO: 1, 2, or 3, and related polypeptides, including SNP variants thereof. Related polypeptides include allelic variants (e.g., SNP variants); splice variants; fragments; derivatives; substitution, deletion, and insertion variants; fusion polypeptides; and interspecies homologs, preferably, which retain TGFβ activity and/or are sufficient to generate an anti-TGFβ immune response. Also encompassed are soluble forms of TGFβ that are sufficient to generate an anti-TGFβ immunological response. As those skilled in the art will appreciate, an anti-TGFβ antibody can bind to a TGFβ polypeptide, polypeptide fragment, antigen, and/or epitope, as an epitope is part of the larger antigen, which is part of the larger polypeptide fragment, which, in turn, is part of the larger polypeptide. hTGFβ can exist in a dimeric or monomeric form.

The terms "TGFβ-mediated disease" and "TGFβ-mediated disorder" are used interchangeably and refer to any disease or disorder that is completely or partially caused by or is the result of TGFβ, e.g., hTGFβ. In certain embodiments, TGFβ is aberrantly expressed. In some embodiments, TGFβ may be aberrantly upregulated in a particular cell type. In other embodiments, normal, aberrant, or excessive cell signaling is caused by binding of TGFβ to a TGFβ receptor. In certain embodiments, the TGFβ receptor (e.g., TGFβ receptor 1, 2, or 3), is expressed on the surface of a cell, such as an osteoblast, osteoclast, or a bone marrow stromal cell. In certain embodiments, the TGFβ-mediated disease is a degenerative bone disease, such as osteogenesis imperfecta.

The terms "specifically binds" or "specifically binding" mean specifically binding to an antigen or a fragment thereof (e.g., TGFβ) and not specifically binding to other antigens. An antibody that specifically binds to an antigen may bind to other peptides or polypeptides with lower affinity, as determined by, e.g., radioimmunoassays (RIA), enzyme-linked immunosorbent assays (ELISA), BIACORE, or other assays known in the art. In certain embodiments, an anti-TGFβ antibody of the invention may specifically bind to TGFβ (e.g., hTGFβ) with more than two-fold greater affinity that a different, non-TGFβ antigen. Antibodies or variants or fragments thereof that specifically bind to an antigen may be cross-reactive with related antigens. For example, in certain embodiments an anti-TGFβ antibody may cross-react with hTGFβ and another TGFβ antigen (e.g., a rodent or non-human primate TGFβ antibody). Preferably, antibodies or variants or fragments thereof that specifically bind to an antigen do not cross-react with other non-TGFβ antigens. An antibody or a variant or a fragment thereof that specifically binds to a TGFβ antigen can be identified, for example, by immunoassays, BIAcore, or other techniques known to those of skill in the art. Typically a specific or selective reaction will be at least twice background signal or noise, and more typically more than 10 times background. In some embodiments, the binding protein or antibody will bind to its antigen, e.g. TGFβ, with a dissociation constant of between $1 \times 10^{-6}$ M and $1 \times 10^{-7}$. In other embodiments, the dissociation constant is between $1 \times 10^{-6}$ M and $1 \times 10^{-8}$. See, e.g., Paul, ed., 1989, Fundamental Immunology Second Edition, Raven Press, New York at pages 332-336 for a discussion regarding antibody specificity.

The terms "subject" and "patient" are used interchangeably. As used herein, a subject is preferably a mammal, such as a non-primate (e.g., cows, pigs, horses, cats, dogs, rats, etc.) or a primate (e.g., monkey and human), most preferably a human. In one embodiment, the subject is a mammal, preferably a human, having a TGFβ-mediated disease. In another embodiment, the subject is a mammal, preferably a human, at risk of developing a TGFβ-mediated disease.

The term "therapeutic agent" refers to any agent that can be used in the treatment, management, or amelioration of a TGFβ-mediated disease and/or a symptom related thereto. In certain embodiments, the term "therapeutic agent" refers to a TGFβ antibody. In certain other embodiments, the term "therapeutic agent" refers to an agent other than a TGFβ antibody. Preferably, a therapeutic agent is an agent that is known to be useful for, or has been, or is currently being used for the treatment, management, or amelioration of a TGFβ-mediated disease, or one or more symptoms related thereto.

The term "therapy" refers to any protocol, method, and/or agent that can be used in the prevention, management, treatment, and/or amelioration of a TGFβ-mediated disease (e.g., OI). In certain embodiments, the terms "therapies" and "therapy" refer to a biological therapy, supportive therapy, and/or other therapies useful in the prevention, management, treatment, and/or amelioration of a TGFβ-mediated disease known to one of skill in the art, such as medical personnel.

The terms "treat", "treatment", and "treating" refer to the reduction or amelioration of the progression, severity, and/or duration of a TGFβ-mediated disease (e.g., OI) resulting from the administration of one or more therapies (including, but not limited to, the administration of one or more prophylactic or therapeutic agents). In specific embodiments, such terms refer to the reduction or inhibition of the binding of TGFβ to a TGFβ receptor, the reduction or inhibition of the production or secretion of TGFβ from a cell expressing a TGFβ receptor of a subject, the reduction or inhibition of the production or secretion of TGFβ from a cell not expressing a TGFβ receptor of a subject, and/or the inhibition or reduction of one or more symptoms associated with a TGFβ-mediated disease, such as OI.

The terms "variable region" or "variable domain" refer to a portion of the light and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complementarity determining regions (CDRs), while the more highly conserved regions in the variable domain are called framework regions (FR). The CDRs of the light and heavy chains are primarily responsible for the interaction of the antibody with antigen. Numbering of amino acid positions is according to the EU Index, as in Kabat et al. (1991) Sequences of proteins of immunological interest. (U.S. Department of Health and Human Services, Washington D.C.) $5^{th}$ ed. ("Kabat et al."). In preferred embodiments, the variable region is a human variable region.

B. Osteogenesis Imperfecta (OI)

OI encompasses a group of congenital bone disorders characterized by deficiencies in one or more proteins involved in bone matrix deposition or homeostasis. There are eight types of OI that are defined by their specific gene mutation, and the resulting protein deficiency and phenotype of the affected individual. Though phenotypes vary among OI types, common symptoms include incomplete ossification of bones and teeth, reduced bone mass, brittle bones, and pathologic fractures.

Type-I collagen is one of the most abundant connective tissue proteins in both calcified and non-calcified tissues. Accurate synthesis, post-translational modification, and secretion of type-I collagen are necessary for proper tissue development, maintenance, and repair. Most mutations identified in individuals with OI result in reduced synthesis of type-I collagen, or incorrect synthesis and/or processing of type-I collagen.

In addition to mutations to the type-I collagen gene, other mutations in genes that participate in the intracellular trafficking and processing of collagens have been identified in OI affected individuals. These genes include molecular chaperones, such as FK506 binding protein 10 (FKBP10) and heat shock protein 47 (HSP47) (Alanay et al., 2010; Christiansen et al., 2010; Kelley et al., 2011). Additional mutations have been identified in intermolecular collagen cross-linking genes, such as procollagen-lysine, 2-oxoglutarate 5-dioxygenase 2 (PLOD2), and in members of the collagen prolyl hydroxylase family of genes, including leucine proline-enriched proteoglycan (leprecan) (LEPRE1), peptidylprolyl isomerase B (cyclophilin B) (CYPB), and cartilage associated protein (CRTAP) (Morello et al., 2006; Cabral et al., 2007; Baldridge et al., 2008; van Dijk et al., 2009; Choi et al., 2009; Barnes et al., 2010; Pyott et al., 2011). Mutations aside, proteins such as bone morphogenetic protein (BMP) and transforming growth factor β

(TGFβ) and their respective receptors are thought to participate in the various OI phenotypes, though the exact mechanisms of their actions are unknown (Gebken et al., 2000).

In an embodiment, TGFβ expression is regulated by molecules that bind type-I and type-II collagen. In certain s embodiment, a small leucine rich proteoglycan (SLRP) regulates TGFβ expression. In a specific embodiment, decorin regulates TGFβ synthesis. In a certain embodiment, decorin does not bind type-I or type-II collagen in which the 3-hydroxyproline site is absent at position 986 of the type-I and/or type-II collagen molecules.

C. Bone Biology

The vertebrate skeleton is comprised of bone, which is a living, calcified tissue that provides structure, support, protection, and a source of minerals for regulating ion transport. Bone is a specialized connective tissue that is comprised of both cellular and acellular components. The acellular extracellular matrix (ECM) contains both collagenous and non-collagenous proteins, both of which participate in the calcification process. A correctly secreted and aligned ECM is critical for proper bone formation. Pathology results when any of the ECM proteins are absent, malformed or misaligned, as is evidenced in osteogenesis imperfecta.

The term "cortical bone" or "compact bone" refers to the outer layer of bone, which is dense, rigid, and tough. The term "trabecular bone" or "cancellous bone" is the spongy inner layer of bone, which is lighter and less dense than cortical bone. The term "trabecula" refers to the microscopic structural unit of spongy bone, which is of a rod-like shape and collagenous composition.

Bone is a dynamic tissue that undergoes constant remodeling. The term "osteoblast" refers to a terminally-differentiated bone forming cell that deposits osteoid. The term "osteoid" refers to immature, unmineralized bone that is comprised primarily of type-I collagen. The term "pre-osteoblast" refers to a proliferating immature osteoblast that is not fully differentiated. The term "osteoprogenitor" refers to a pluripotent cell that gives rise to several stromal cell types, including osteoblasts. Osteoprogenitor cells, which are commonly referred to as "mesenchymal stem cells," arise in the bone marrow and can be isolated in small numbers from circulating blood. The term "osteoclast" refers to a terminally-differentiated bone resorbing cell that is descended from a bone marrow monocyte. Osteoclasts can be identified by their expression of tartrate resistant acid phosphatase (TRAP).

Under normal homeostatic conditions, osteoblasts and osteoclasts work in unison to maintain bone integrity. Pathology results when bone deposition and bone resorption become uncoupled. For example, osteopetrosis is a bone disease characterized by overly dense, hard bone that is a result of unresorptive osteoclasts, while osteoporosis is a bone disorder characterized by brittle, porous bones which can result from increased osteoclast activity. Evidence suggests that osteoclast activity may be increased in osteogenesis imperfecta, implicating these cell types as a potential target for therapeutic intervention. The present disclosure includes methods of inhibiting osteoclasts with a TGFβ antibody.

Several methods can be used to measure and characterize the structure, density, and quality of bone, including histology and histomorphometry, atomic force microscopy, confocal Raman microscopy, nanoindentation, three-point bending test, X-ray imaging, and micro computed tomography (μ-CT). In an exemplified embodiment, bones are measured and characterized by at least one of these methods.

The term "bone volume density" refers to the fraction of a given volume of bone (total volume or TV) that is comprised of calcified matter (bone volume or BV). Therefore, bone volume density is calculated as BV/TV and reported as a percentage. The term "specific bone surface" refers to the total bone surface (BS) per given volume of bone. Therefore, specific bone surface is calculated as BS/TV. Other common bone measurements include: bone area (B.Ar), trabecular number (Tb.N); trabecular spacing (Tb.Sp); N.Oc (osteoclast number); Oc.S (osteoclast surface area); Oc.S/BS; osteoblast number (N.Ob), osteoblast surface area (Ob.S), osteoblast perimeter (Ob.Pm), and derivatives of any of said measurements. A larger Oc.S/BS is an indicator of increased bone resorption by osteoclasts.

D. Transforming growth factor beta (TGFβ)

TGFβs are multifunctional cytokines that are involved in cell proliferation and differentiation, embryonic development, extracellular matrix formation, bone development, wound healing, hematopoiesis, and immune and inflammatory responses (Roberts et al., 1981; Border et al., 1995a). Secreted TGFβ protein is cleaved into a latency-associated peptide (LAP) and a mature TGFβ peptide, and is found in latent and active forms. The mature TGFβ peptide forms both homodimers and heterodimers with other TGFβ family members. TGFβ may be purified from any natural source, or may be produced synthetically (e.g., by use of recombinant DNA technology). Preferably, the TGFβ molecule is from a human, known herein as "hTGF."

There are three human TGFβ isoforms: TGFβ1, TGFβ2, and TGFβ3 (Swiss Prot accession numbers P01137, P08112, and P10600, respectively) which, in their biologically active state, are 25 kDa homodimers comprising two 112 amino acid monomers joined by an inter-chain disulfide bridge. TGFβ1 differs from TGFβ2 by 27, and from TGFβ3 by 22, mainly conservative amino acid changes. These differences have been mapped on the 3D structure of TGFβ determined by X-ray crystallography (Schlunegger et al., 1992; Peer et al., 1996) and the receptor binding regions have been defined (Griffith et al., 1996; Qian et al., 1996).

```
hTGFβ1 (SEQ ID NO: 1)
                                                                    (SEQ ID NO: 1)
         MPPSGLRLLL LLLPLLWLLV LTPGRPAAGL STCKTIDMEL VKRKRIEAIR GQILSKLRLA    60

SPPSQGEVPP GPLPEAVLAL YNSTRDRVAG ESAEPEPEPE ADYYAKEVTR VLMVETHNEI   120

YDKFKQSTHS IYMFFNTSEL REAVPEPVLL SRAELRLLRL KLKVEQHVEL YQKYSNNSWR   180

YLSNRLLAPS DSPEWLSFDV TGVVRQWLSR GGEIEGFRLS AHCSCDSRDN TLQVDINGFT   240

TGRRGDLATI HGMNRPFLLL MATPLERAQH LQSSRHRRAL DTNYCFSSTE KNCCVRQLYI   300
```

```
                                                 -continued
DFRKDLGWKW  IHEPKGYHAN  FCLGPCPYIW  SLDTQYSKVL  ALYNQHNPGA  SAAPCCVPQA   360

LEPLPIVYYV  GRKPKVEQLS  NMIVRSCKCS                                      390 hTGFβ2 (SEQ ID NO: 2)
                                                            (SEQ ID NO: 2)
MHYCVLSAFL  ILHLVTVALS  LSTCSTLDMD  QFMRKRIEAI  RGQILSKLKL  TSPPEDYPEP   60

EEVPPEVISI  YNSTRDLLQE  KASRRAAACE  RERSDEEYYA  KEVYKIDMPP  FFPSENAIPP   120

TFYRPYFRIV  RFDVSAMEKN  ASNLVKAEFR  VFRLQNPKAR  VPEQRIELYQ  ILKSKDLTSP   180

TQRYIDSKVV  KTRAEGEWLS  FDVTDAVHEW  LHHKDRNLGF  KISLHCPCCT  FVPSNNYIIP   240

NKSEELEARF  AGIDGTSTYT  SGDQKTIKST  RKKNSGKTPH  LLLMLLPSYR  LESQQTNRRK   300

KRALDAAYCF  RNVQDNCCLR  PLYIDFKRDL  GWKWIHEPKG  YNANFCAGAC  PYLWSSDTQH   360

SRVLSLYNTI  NPEASASPCC  VSQDLEPLTI  LYYIGKTPKI  EQLSNMIVKS  CKCS         414 hTGFβ3 (SEQ ID NO: 3)
                                                            (SEQ ID NO: 3)
MKMHLQRALV  VLALLNFATV  SLSLSTCTTL  DFGHIKKKRV  EAIRGQILSK  LRLTSPPEPT   60

VMTHVPYQVL  ALYNSTRELL  EEMHGEREEG  CTQENTESEY  YAKEIHKFDM  IQGLAEHNEL   120

AVCPKGITSK  VFRFNVSSVE  KNRTNLFRAE  FRVLRVPNPS  SKRNEQRIEL  FQILRPDEHI   180

AKQRYIGGKN  LPTRGTAEWL  SFDVTDTVRE  WLLRRESNLG  LEISIHCPCH  TFQPNGDILE   240

NIHEVMEIKF  KGVDNEDDHG  RGDLGRLKKQ  KDHHNPHLIL  MMIPPHRLDN  PGQGGQRKKR   300

ALDTNYCFRN  LEENCCVRPL  YIDFRQDLGW  KWVHEPKGYY  ANFCSGPCPY  LRSADTTHST   360

VLGLYNTLNP  EASASPCCVP  QDLEPLTILY  YVGRTPKVEQ  LSNMVVKSCK  CS           412
```

There are three TGFβ receptors in humans, TGFβ receptor 1, 2, and 3, which can be distinguished by their structural and functional properties, including affinity for TGFβ protein family members. Binding of a TGFβ protein to a homodimeric or heterodimeric TGFβ transmembrane receptor complex activates the canonical TGFβ signaling pathway mediated by intracellular SMAD proteins.

The deregulation of TGFβs leads to pathological processes that, in humans, have been implicated in numerous conditions, such as, birth defects, cancer, chronic inflammatory, autoimmune diseases, and fibrotic diseases (Border et al., 1994; Border et al., 1995b).

Human TGFβs are very similar to mouse TGFβs: human TGFβ1 has only one amino acid difference from mouse TGFβ1; human TGFβ2 has only three amino acid differences from mouse TGFβ2; and human TGFβ3 is identical to mouse TGFβ3.

E. Molecules that Bind to Transforming Growth Factor Beta (TGFβ)

The present invention includes methods that comprise administering to a subject a molecule that binds to TGFβ. The TGFβ binder may be any binding molecule, such as an antibody, a fusion protein (e.g., an immunoadhesin), an siRNA, a nucleic acid, an aptamer, a protein, or a small molecule organic compound.

In certain embodiments, the invention includes an antibody that binds to TGFβ (an anti-TGFβ antibody), or a variant thereof, or an antigen-binding fragment thereof. Anti-TGFβ antibodies specifically bind to a TGFβ protein, polypeptide fragment, or epitope. The molecule that binds to TGFβ may be from any species.

In certain exemplary embodiments, the antibody that binds to TGFβ is a humanized antibody, a fully human antibody, or a variant thereof, or an antigen-binding fragment thereof. Preferred anti-TGFβ antibodies prevent binding of TGFβ with its receptors and inhibit TGFβ biological activity (e.g., the TGFβ receptor-mediated intracellular SMAD signaling and resulting cellular activity).

In certain embodiments, the antibody, or antigen-binding fragment thereof, is Lerdelimumab (CAT-152), Metelimumab (CAT-192), Fresolimumab (GC-1008), LY2382770, STX-100, or IMC-TR1.

In certain specific embodiments, the antibody that binds to TGFβ comprises a heavy chain variable region (VH) comprising the amino acid sequence of any one or more of the following complementarity determining regions (CDRs):

HCDR1
(SEQ ID NO: 4)
SNVIS;

HCDR2
(SEQ ID NO: 5)
GVIPIVDIANYAQRFKG;
or

HCDR3
(SEQ ID NO: 6)
TLGLVLDAMDY.

In other specific embodiments, the antibody that binds to TGFβ comprises a light chain variable region (VL) comprising the amino acid sequence of any one or more of the following complementarity determining regions (CDRs):

LCDR1

RASQSLGSSYLA;
(SEQ ID NO: 7)

LCDR2

GASSRAP;
(SEQ ID NO: 8)

or

LCDR3

QQYADSPIT.
(SEQ ID NO: 9)

In a specific embodiment, the antibody that binds to TGFβ comprises a heavy chain variable region (VH) comprising the amino acid sequences of SEQ ID NOs: 4, 5, and 6.

In another specific embodiment, the antibody that binds to TGFβ comprises a light chain variable region (VL) comprising the amino acid sequences of SEQ ID NOs: 7, 8, and 9.

In more specific embodiments, the antibody that binds to TGFβ comprises a heavy chain variable region comprising the amino acid sequences of SEQ ID NOs: 4, 5, and 6; and a light chain variable region comprising the amino acid sequences of SEQ ID NOs: 7, 8, and 9.

In a specific embodiment, the antibody that binds to TGFβ comprises a heavy chain variable region comprising the amino acid sequence of SEQ ID NO: 10:

(SEQ ID NO: 10)
QVQLVQSGAE VKKPGSSVKV SCKASGYTFS SNVISWVRQA

PGQGLEWMGG VIPIVDIANY AQRFKGRVTI TADESTSTTY

MELSSLRSED TAVYYCASTL GLVLDAMDYW GQGTLVTVSS.

In another specific embodiment, the antibody that binds to TGFβ comprises a light chain variable region comprising the amino acid sequence of SEQ ID NO: 11:

(SEQ ID NO: 11)
ETVLTQSPGT LSLSPGERAT LSCRASQSLG SSYLAWYQQK

PGQAPRLLIY GASSRAPGIP DRFSGSGSGT DFTLTISRLE

PEDFAVYYCQ QYADSPITFG QGTRLEIK.

In more specific embodiments, the antibody that binds to TGFβ comprises a heavy chain variable region comprising the amino acid sequence of SEQ ID NO: 10; and a light chain variable region comprising the amino acid sequence of SEQ ID NO: 11.

In some embodiments, the antibody that binds to TGFβ further comprises a constant region, e.g., a human IgG constant region. In some embodiments, the constant region is a human IgG4 constant region. In additional embodiments, the constant region is a modified human IgG4 constant region. Preferably, the IgG4 constant region comprises the amino acid sequence of SEQ ID NO: 12:

(SEQ ID NO: 12)
ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRVES KYGPPCPSCP APEFLGGPSV

FLFPPKPKDT LMISRTPEVT CVVVDVSQED PEVQFNWYVD

GVEVHNAKTK PREEQFNSTY RVVSVLTVLH QDWLNGKEYK

CKVSNKGLPS SIEKTISKAK GQPREPQVYT LPPSQEEMTK

NQVSLTCLVK GFYPSDIAVE WESNGQPENN YKTTPPVLDS

DGSFFLYSRL TVDKSRWQEG NVFSCSVMHE ALHNHYTQKS

LSLSLGK.

In other embodiments, the constant region is a human C$_\kappa$ constant region. Preferably, the C$_\kappa$ constant region comprises the amino acid sequence of SEQ ID NO: 13:

RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC (SEQ ID NO: 13).

In specific embodiments, the antibody that binds to TGFβ comprises a heavy chain comprising the amino acid sequence of SEQ ID NO: 14:

(SEQ ID NO: 14)
QVQLVQSGAE VKKPGSSVKV SCKASGYTFS SNVISWVRQA

PGQGLEWMGG VIPIVDIANY AQRFKGRVTI TADESTSTTY

MELSSLRSED TAVYYCASTL GLVLDAMDYW GQGTLVTVSS

ASTKGPSVFP LAPCSRSTSE STAALGCLVK DYFPEPVTVS

WNSGALTSGV HTFPAVLQSS GLYSLSSVVT VPSSSLGTKT

YTCNVDHKPS NTKVDKRVES KYGPPCPSCP APEFLGGPSV

FLFPPKPKDT LMISRTPEVT CVVVDVSQED PEVQFNWYVD

GVEVHNAKTK PREEQFNSTY RVVSVLTVLH QDWLNGKEYK

CKVSNKGLPS SIEKTISKAK GQPREPQVYT LPPSQEEMTK

NQVSLTCLVK GFYPSDIAVE WESNGQPENN YKTTPPVLDS

DGSFFLYSRL TVDKSRWQEG NVFSCSVMHE ALHNHYTQKS

LSLSLGK.

Positions 1-120: variable region of the heavy chain (VH). The CDRs (complementarity determining regions, according to Kabat definition) are underlined.

Positions 121-447: constant region of human IgG4 (SwissProt IGHG4_HUMAN).

In other specific embodiments, the antibody that binds to TGFβ comprises a light chain comprising the amino acid sequence of SEQ ID NO: 15:

(SEQ ID NO: 15)
ETVLTQSPGT LSLSPGERAT LSCRASQSLG SSYLAWYQQK

PGQAPRLLIY GASSRAPGIP DRFSGSGSGT DFTLTISRLE

PEDFAVYYCQ QYADSPITFG QGTRLEIKRT VAAPSVFIFP

PSDEQLKSGT ASVVCLLNNF YPREAKVQWK VDNALQSGNS

QESVTEQDSK DSTYSLSSTL TLSKADYEKH KVYACEVTHQ

GLSSPVTKSF NRGEC.

Positions 1-108: variable region of the light chain (VL). The CDRs (complementarity determining regions, according to Kabat definition) are underlined.

Positions 109-215: constant region of human C_κ.

In further embodiments, the antibody that binds to TGFβ comprises a heavy chain comprising the amino acid sequence of SEQ ID NO: 14, and a light chain comprising the amino acid sequence of SEQ ID NO: 15.

In some embodiments, the antibody that binds to TGFβ is expressed by a host cells as comprising leader sequences. The leader sequence preferably comprises an amino acid sequence from 1-30 amino acids in length, more preferably 25-25 amino acids, and most preferably 19 amino acids. The heavy chain, light chain, or both the heavy and light chain may comprise a leader sequence.

For example, the light or heavy chain leader sequence may comprise the amino acid sequence of SEQ ID NO: 16: MGWSCIILFL VATATGVHS (SEQ ID NO: 16).

Accordingly, a host cell may expressing a unprocessed heavy chain may comprise the amino acid sequence of SEQ ID NO: 17:

```
                                                    (SEQ ID NO: 17)
MGWSCIILFL VATATGVHSQ VQLVQSGAEV KKPGSSVKVS CKASGYTFSS   50

NVISWVRQAP GQGLEWMGGV IPIVDIANYA QRFKGRVTIT ADESTSTTYM  100

ELSSLRSEDT AVYYCASTLG LVLDAMDYWG QGTLVTVSSA STKGPSVFPL  150

APCSRSTSES TAALGCLVKD YFPEPVTVSW NSGALTSGVH TFPAVLQSSG  200

LYSLSSVVTV PSSSLGTKTY TCNVDHKPSN TKVDKRVESK YGPPCPSCPA  250

PEFLGGPSVF LFPPKPKDTL MISRTPEVTC VVVDVSQEDP EVQFNWYVDG  300

VEVHNAKTKP REEQFNSTYR VVSVLTVLHQ DWLNGKEYKC KVSNKGLPSS  350

IEKTISKAKG QPREPQVYTL PPSQEEMTKN QVSLTCLVKG FYPSDIAVEW  400

ESNGQPENNY KTTPPVLDSD GSFFLYSRLT VDKSRWQEGN VFSCSVMHEA  450

LHNHYTQKSL SLSLGK,                                     466
``` wherein
positions 1-19: leader sequence
Positions 20-139: variable region of the heavy chain (VH). The CDRs (complementarity determining regions, according to Kabat definition) are underlined.
Positions 140-466: constant region of human IgG4 (SwissProt IGHG4_HUMAN).

In other exemplary embodiments, a host cell expressing a unprocessed light chain may comprise the amino acid of SEQ ID NO: 18:

```
                                                    (SEQ ID NO: 18)
MGWSCIILFL VATATGVHSE TVLTQSPGTL SLSPGERATL SCRASQSLGS   50

SYLAWYQQKP GQAPRLLIYG ASSRAPGIPD RFSGSGSGTD FTLTISRLEP  100

EDFAVYYCQQ YADSPITFGQ GTRLEIKRTV AAPSVFIFPP SDEQLKSGTA  150

SVVCLLNNFY PREAKVQWKV DNALQSGNSQ ESVTEQDSKD STYSLSSTLT  200

LSKADYEKHK VYACEVTHQG LSSPVTKSFN RGEC,                  234
``` wherein
Positions 1-19: leader sequence
Positions 20-127: variable region of the light chain (VL). The CDRs (complementarity determining regions, according to Kabat definition) are underlined.
Positions 128-234: constant region of human C_κ.

In specific embodiments, the antibody that binds to TGFβ is CAT-192 or an antigen-binding fragment thereof, and comprises a VH comprising the amino acid sequence of SEQ ID NO: 22 and a VL comprising the amino acid sequence of SEQ ID NO: 23:

```
                                       (SEQ ID NO: 22)
EVQLVESGGG VVQPGRSLRL SCAASGFTFS SYGMHWVRQA

PGKELEWVAV ISYDGSIKYY ADSVKGRFTI SRDNSKNTLY

LQMNSLRAED TAVYYCARTG EYSGYDTDPQ YSWGQGTTVT

VSS
```

-continued
```
                                       (SEQ ID NO: 23)
EIVLTQSPSS LSASVGDRVT ITCRASQGIG DDLGWYQQKP

GKAPILLIYG TSTLQSGVPS RFSGSGSGTD FTLTINSLQP

EDFATYYCLQ DSNYPLTFGG GTRLEIK.
```

In specific embodiments, the antibody that binds to TGFβ is CAT-152 or an antigen-binding fragment thereof, and comprises a VH comprising the amino acid sequence of SEQ ID NO: 24 and a VL comprising the amino acid sequence of SEQ ID NO: 25:

```
                                            (SEQ ID NO: 24)
EVQLVESGGG VVQPGRSLRL SCAASGFTFS SYGMHWVRQA

PGKGLEWVAV IWYDGSNKYY ADSVKGRFTI SRDNSKNTLY

LQMDSLRAED TAVYYCGRTL ESSLWGQGTL VTVSS (SEQ ID NO: 25)
SSELTQDPAV SVALGQTVRI TCQGDSLRSY YASWYQQKPG

QAPVLVIYGK NNRPSGIPDR FSGSSSGNTA SLTITGAQAE

DEADYYCNSR DSSSTHRGVF GGGTKLTVLG.
```

In an exemplary embodiment of the invention, the antibody that binds to TGFβ is a humanized or fully human antibody. Examples of humanized and fully human antibody isotypes include IgA, IgD, IgE, IgG, and IgM. Preferably, the anti-TGFβ antibody is an IgG antibody. There are four forms of IgG. Preferably, the anti-TGFβ antibody is an IgG4 antibody. In one embodiment of the invention, the anti-TGFβ antibody is a humanized IgG4 antibody. In another embodiment of the invention, the anti-TGFβ antibody is a fully human IgG4 antibody.

In a most preferred embodiment of the invention, the anti-TGFβ antibody is an IgG4 anti-TGFβ antibody comprising a heavy chain comprising the amino acid sequence of SEQ ID NO: 14 and a light chain comprising the amino acid sequence of SEQ ID NO: 15. In an alternative most preferred embodiment of the invention, the anti-TGFβ antibody is an IgG4 anti-TGFβ antibody comprising a heavy chain variable region and a light chain variable region, the heavy chain variable region comprising 3 complementarity determining regions (CDRs) comprising the amino acid sequences of SEQ ID NOs: 4, 5, and 6, and the light chain variable region comprising 3 CDRs comprising the amino acid sequences of SEQ ID NOs: 7, 8, and 9. Identification, isolation, preparation, and characterization of anti-TGFβ antibodies, including the anti-TGFβ antibody comprising a heavy chain amino acid sequence comprising SEQ ID NO: 14 and a light chain amino acid sequence comprising SEQ ID NO: 15, and the CDR sequences corresponding with SEQ ID NOs: 4-9 have been described in detail in U.S. Pat. Nos. 7,723,486, and 8,383,780, each of which is incorporated herein by reference in its entirety.

Preferably, the antibody or antigen-binding fragment thereof is "pan-specific" and binds to human TGFβ1, TGFβ2, and TGFβ3. More preferably, the antibody or antigen-binding fragment thereof binds to human TGFβ1, TGFβ2, and TGFβ3, and acts as an antagonist. Most preferably, the antibody or antigen-binding fragment thereof binds to human TGFβ1, TGFβ2, and TGFβ3, and neutralizes human TGFβ1, TGFβ2, and TGFβ3. Exemplary pan-specific anti-TGFβ monoclonal antibodies (mAbs) suitable for use in the methods of the invention are described in U.S. Pat. Nos. 7,723,476 and 8,383,780, each of which is incorporated by reference herein in its entirety.

1D11.16 is an exemplary murine pan-specific anti-TGFβ antibody that neutralizes human and mouse TGFβ1, TGFβ2, and TGFβ3 in a wide range of in vitro assays (Dasch et al., 1989; Dasch et al., 1996; R&D System product sheet for MAB1835, each of which is incorporated herein by reference in their entirety) and is efficacious in proof-of principle studies in animal models of fibrosis (Ling et al., 2003; Miyajima et al., 2000; Schneider et al., 1999; Khanna et al., 1999; Shenkar et al., 1994). However, since 1D11.16 is a murine monoclonal antibody (Dasch et al., 1989; Dasch et al., 1996), it is not a preferred for therapeutic use in humans. Accordingly, in certain embodiments, variants or derivatives of the 1D11.16 antibody are employed in the methods of the invention.

As indicated above, certain embodiments of the invention also include variants or derivatives of anti-TGFβ antibodies. Specifically, the invention may include variants of the anti-TGFβ antibody that is an IgG4 anti-TGFβ antibody comprising a heavy chain comprising the amino acid sequence of SEQ ID NO: 14, and a light chain comprising the amino acid sequence of SEQ ID NO: 15. In other embodiment, the invention includes variants or derivatives of the 1D11.16 antibody. Variants of anti-TGFβ antibodies may have similar physicochemical properties based on their high similarity, and therefore are also included within the scope of the invention. Variants are defined as antibodies with an amino acid sequence that is at least 80%, at least 90%, at least 95%, or at least 97%, e.g., least 98% or 99% homologous to an anti-TGFβ antibody described herein, and capable of competing for binding to a TGFβ polypeptide, a TGFβ polypeptide fragment, or a TGFβ epitope. Preferably, the variants will ameliorate, neutralize, or otherwise inhibit binding of TGFβ with its receptors and TGFβ biological activity (e.g., TGFβ receptor-mediated intracellular SMAD signaling and resulting cellular activity). Determining competition for binding to the target can be done by routine methods known to the skilled person in the art. Preferably the variants are human antibodies, and preferably are IgG4 molecules. In preferred embodiments, a variant is at least 90%, 95%, 96%, 97%, 98%, or 99% identical in amino acid sequence with the IgG4 anti-TGFβ antibody comprising a heavy chain comprising the amino acid sequence of SEQ ID NO: 14, and a light chain comprising the amino acid sequence of SEQ ID NO: 15. The term "variant" refers to an antibody that comprises an amino acid sequence that is altered by one or more amino acids compared to the amino acid sequences of the anti-TGFβ antibody. The variant may have conservative sequence modifications, including amino acid substitutions, modifications, additions, and deletions.

Examples of modifications include, but are not limited to, glycosylation, acetylation, pegylation, phosphorylation, amidation, derivatization by known protecting/blocking groups, proteolytic cleavage, and linkage to a cellular ligand or other protein. Amino acid modifications can be introduced by standard techniques known in the art, such as site-directed mutagenesis, molecular cloning, oligonucleotide-directed mutagenesis, and random PCR-mediated mutagenesis in the nucleic acid encoding the antibodies. Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), nonpolar side chains (e.g., glycine, alanine, valine, leucine, isoleucine, proline, phenylalanine, methionine), beta-branched side chains (e.g., threonine, valine, isoleucine), and aromatic side chains (e.g., tyrosine, phenylalanine, tryptophan). It will be clear to the skilled artisan that classifications of amino acid residue families other than the one used above can also be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, modified, inserted, or deleted without abolishing immunological activity may be found using computer programs well known in the art. Computer algorithms, such as, inter alia, Gap or Bestfit, which are known to a person skilled in the art, can be used to optimally align amino acid sequences to be compared and to define similar or identical amino acid residues. Variants may have the same or different, either higher or lower, binding affinities compared to an anti-TGFβ antibody, but are still capable of specifically binding to TGFβ, and may have the same, higher or lower, biological activity as the anti-TGFβ antibody.

Embodiments of the invention also include antigen-binding fragments of the anti-TGFβ antibodies. The term "antigen-binding domain," "antigen-binding region," "antigen-binding fragment," and similar terms refer to that portion of an antibody that comprises the amino acid residues that interact with an antigen and confer on the binding agent its specificity and affinity for the antigen (e.g., the complementarity determining regions (CDR)). The antigen-binding region can be derived from any animal species, such as rodents (e.g., rabbit, rat or hamster) and humans. Preferably, the antigen-binding region will be of human origin. Non-limiting examples of antigen-binding fragments include: Fab fragments, F(ab')2 fragments, Fd fragments, Fv fragments, single chain Fv (scFv) molecules, dAb fragments, and minimal recognition units consisting of the amino acid residues that mimic the hypervariable region of the antibody.

F. Therapeutic Administration

The methods described herein comprise administering a therapeutically effective amount of an antibody that binds to TGFβ to a subject. As used herein, the phrase "therapeutically effective amount" means a dose of antibody that binds to TGFβ that results in a detectable improvement in one or more symptoms associated with OI or which causes a biological effect (e.g., a decrease in the level of a particular biomarker) that is correlated with the underlying pathologic mechanism(s) giving rise to the condition or symptom(s) of osteogenesis imperfecta. For example, a dose of antibody that binds to TGFβ that increases bone mineral density, increases bone mass and/or bone strength, reduces bone and/or tooth fractures, and/or improves any diagnostic measurement of OI is deemed a therapeutically effective amount.

In an embodiment, bone mineral density, bone mass, and/or bone strength are increased by about 5% to about 200% following treatment with an antibody that binds to TGFβ. In certain embodiments, bone mineral density, bone mass, and/or bone strength are increased by about 5% to about 10%, 10% to about 15%, 15% to about 20%, 20% to about 25%, 25% to about 30%, 30% to about 35%, 35% to about 40%, 40% to about 45%, 45% to about 50%, 50% to about 55%, 55% to about 60%, 60% to about 65%, 65% to about 70%, 70% to about 75%, 75% to about 80%, 80% to about 85%, 85% to about 90%, 90% to about 95%, 95% to about 100%, 100% to about 105%, 105% to about 110%, 110% to about 115%, 115% to about 120%, 120% to about 125%, 125% to about 130%, 130% to about 135%, 135% to about 140%, 140% to about 145%, 145% to about 150%, 150% to about 155%, 155% to about 160%, 160% to about 165%, 165% to about 170%, 170% to about 175%, 175% to about 180%, 180% to about 185%, 185% to about 190%, 190% to about 195%, or 195% to about 200%, following treatment with an antibody that binds to TGFβ.

In certain embodiments, a dose of an antibody which reduces serum biomarkers of bone resorption, such as urinary hydroxyproline, urinary total pyridinoline (PYD), urinary free deoxypyridinoline (DPD), urinary collagen type-I cross-linked N-telopeptide (NTX), urinary or serum collagen type-I cross-linked C-telopeptide (CTX), bone sialoprotein (BSP), osteopontin (OPN), and tartrate-resistant acid phosphatase 5b (TRAP), is deemed a therapeutically effective amount. In an embodiment, serum biomarkers of bone resorption are reduced by about 5% to about 200% following treatment with an antibody that binds to TGFβ

In an embodiment, serum biomarkers of bone resorption, such as urinary hydroxyproline, urinary total pyridinoline (PYD), urinary free deoxypyridinoline (DPD), urinary collagen type-I cross-linked N-telopeptide (NTX), urinary or serum collagen type-I cross-linked C-telopeptide (CTX), bone sialoprotein (BSP), osteopontin (OPN), and tartrate-resistant acid phosphatase 5b (TRAP), are decreased by about 5% to about 10%, 10% to about 15%, 15% to about 20%, 20% to about 25%, 25% to about 30%, 30% to about 35%, 35% to about 40%, 40% to about 45%, 45% to about 50%, 50% to about 55%, 55% to about 60%, 60% to about 65%, 65% to about 70%, 70% to about 75%, 75% to about 80%, 80% to about 85%, 85% to about 90%, 90% to about 95%, 95% to about 100%, 100% to about 105%, 105% to about 110%, 110% to about 115%, 115% to about 120%, 120% to about 125%, 125% to about 130%, 130% to about 135%, 135% to about 140%, 140% to about 145%, 145% to about 150%, 150% to about 155%, 155% to about 160%, 160% to about 165%, 165% to about 170%, 170% to about 175%, 175% to about 180%, 180% to about 185%, 185% to about 190%, 190% to about 195%, or 195% to about 200%, following treatment with an antibody that binds to TGFβ.

In certain embodiments, a dose of an antibody which increase serum biomarkers of bone deposition, such as total alkaline phosphatase, bone-specific alkaline phosphatase, osteocalcin, and type-I procollagen (C-terminal/N-terminal), is deemed a therapeutically effective amount. In an embodiment, serum biomarkers of bone deposition are increased by about 5% to about 200% following treatment with an antibody that binds to TGFβ.

In an embodiment, serum biomarkers of bone deposition, such as total alkaline phosphatase, bone-specific alkaline phosphatase, osteocalcin, and type-I procollagen (C-terminal/N-terminal), are increased by about 5% to about 10%, 10% to about 15%, 15% to about 20%, 20% to about 25%, 25% to about 30%, 30% to about 35%, 35% to about 40%, 40% to about 45%, 45% to about 50%, 50% to about 55%, 55% to about 60%, 60% to about 65%, 65% to about 70%, 70% to about 75%, 75% to about 80%, 80% to about 85%, 85% to about 90%, 90% to about 95%, 95% to about 100%, 100% to about 105%, 105% to about 110%, 110% to about 115%, 115% to about 120%, 120% to about 125%, 125% to about 130%, 130% to about 135%, 135% to about 140%, 140% to about 145%, 145% to about 150%, 150% to about 155%, 155% to about 160%, 160% to about 165%, 165% to about 170%, 170% to about 175%, 175% to about 180%, 180% to about 185%, 185% to about 190%, 190% to about 195%, or 195% to about 200%, following treatment with an antibody that binds to TGFβ.

Other embodiments include administering a therapeutically effective dose of an antibody which improves the function of non-skeletal organs affected by OI. For example, a dose of antibody that binds to TGFβ that improves hearing, lung, and/or kidney function is deemed a therapeutically effective amount.

In accordance with the methods of the present invention, a therapeutically effective amount of an antibody that binds to TGFβ that is administered to a subject will vary depending upon the age and the size (e.g., body weight or body surface area) of the subject, as well as the route of administration, and other factors well known to those of ordinary skill in the art.

In certain exemplary embodiments, the anti-TGFβ antibody is administered to the subject as a subcutaneous dose. Other exemplary modes of administration include, but are not limited to, intradermal, intramuscular, intraperitoneal, intravenous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The TGFβ antibody can be administered parenterally or subcutaneously.

Various delivery systems are known and can be used to administer the pharmaceutical composition, e.g., encapsulation in liposomes, microparticles, microcapsules, receptor mediated endocytosis (see, e.g., Wu et al. (1987) J. Biol. Chem. 262:4429-4432). The therapeutic compositions will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Pharmaceutical compositions may be prepared into dosage forms in a unit dose suited to fit a dose of the active ingredients. Such dosage forms in a unit dose include, for example, tablets, pills, capsules, injections (ampoules), suppositories, etc.

Pharmaceutical compositions can also be administered to the subject using any acceptable device or mechanism. For example, the administration can be accomplished using a syringe and needle or with a reusable pen and/or autoinjector delivery device. The methods of the present invention include the use of numerous reusable pen and/or autoinjector delivery devices to administer a TGFβ binder (or pharmaceutical formulation comprising the binder). Examples of such devices include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™ OPTIPEN STARLET™, and OPTICLIK™ (sanofi-aventis, Frankfurt, Germany), to name only a few. Examples of disposable pen and/or autoinjector delivery devices having applications in subcutaneous delivery of a pharmaceutical composition include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park, IL), to name only a few.

The use of a microinfusor to deliver a TGFβ binder (or pharmaceutical formulation comprising the binder) to a subject is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., J. Controlled Release 46:107-116 (1996). Microinfusors are particularly useful for the delivery of large doses of therapeutic proteins contained within high concentration (e.g., about 100, 125, 150, 175, 200 or more mg/mL) and/or viscous solutions.

G. Combination Therapies

In certain aspects, the invention includes methods for treating OI that comprise administering to a subject in need of such treatment an antibody that binds to TGFβ in combination with at least one additional therapeutic agent. Examples of additional therapeutic agents that can be administered in combination with an anti-TGFβ antibody in the practice of the methods of the present invention include, but are not limited to, bisphosphonates, calcitonin, teriparatide, and any other compound known to treat, prevent, or ameliorate osteogenesis imperfecta in a subject. In the present methods, the additional therapeutic agent(s) can be administered concurrently or sequentially with the antibody that binds to TGFβ. For example, for concurrent administration, a pharmaceutical formulation can be made that contains both an antibody that binds to TGFβ and at least one additional therapeutic agent. In an embodiment, the antibody that binds to TGFβ is administered in combination with pharmaceutical bisphosphonates (e.g., Etidronate, Clodronate, Tiludronate, Pamidronate, Neridronate, Olpadronate, Alendronate, Ibandronate, Zoledronate, and Risedronate). In another embodiment, the antibody that binds to TGFβ is administered in combination with a drug that stimulates bone formation, such as parathyroid hormone analogs and calcitonin. In yet another embodiment, the antibody that binds to TGFβ is administered in combination with a selective estrogen receptor modulator (SERM). The amount of the additional therapeutic agent that is administered in combination with the antibody that binds to TGFβ in the practice of the methods of the present invention can be easily determined using routine methods known and readily available in the art.

EXAMPLES

OI is a generalized connective tissue disease in which affected individuals display an abnormality in forming type-I collagen fibrils due to mutations in the primary sequence of the alpha 1 or alpha 2 chain of type-I collagen, as well abnormalities in the post-translational modification of type-I collagen and proteins that bind type-I collagen fibrils. CRTAP encodes a protein called the cartilage associated protein, a member of the prolyl-3-hydroxylation complex whose function is to assist with the proper folding, post-translational modification and secretion of type-I collagen. Mutations to CRTAP are responsible for type VII osteogenesis imperfecta. Mice lacking the Crtap gene (Crtap$^{-/-}$) display a phenotype that mimics osteogenesis imperfecta, and are used as a model of this disease (Morello et al., 2006). Crtap$^{-/-}$ mice and age-matched wild type (WT) littermate controls were used in the following examples.

Material and Methods

Animals, Anti-TGFβ Treatment and Tissue Collection

Crtap$^{-/-}$ mice were generated and maintained on a mixed C57Black/6J/129Sv genetic background. Mice harboring a G610C mutation in the Col1a2 gene (Col1a2$^{tm1.1Mcbr}$) were obtained and bred to wildtype C57Bl/6J mice. Mice that were heterozygous for the Col1a2$^{tm1.1Mcbr}$ allele were used for experiments. TGFβ-reporter mice that express luciferase in response to the Smad2/3 dependent TGFβ signaling pathway (SBE-Luc mice) were obtained and bred to Crtap$^{+/-}$ mice for 2 generations to generate Crtap$^{-/-}$ mice and wild-type littermates expressing the reporter transgene. All mice were housed in a vivarium and animal experiments were performed following the approved protocol of the Animal Care and Use Committee (IACUC).

For protein and RNA analyses, calvaria of P3 mice were isolated, cleaned of extraskeletal tissue, and snap frozen in liquid nitrogen. For immunostaining of Crtap$^{-/-}$ P10 mice lungs, the lungs of each mouse were equally inflated immediately after sacrifice by gravity with 4% paraformaldehyde at a constant pressure of 25 cm H$_2$O and then suture closed at the trachea. Lungs were then gently dissected from the thorax and fixed in 4% paraformaldehyde overnight.

Eight week old female Crtap$^{-/-}$ and Col1a2$^{tm1.1Mckbr}$ mice were treated with the pan-TGFβ neutralizing antibody 1D11 for 8 weeks (10 mg/kg body weight, I.P. injections 3 times each week). Control Crtap$^{-/-}$, Col1a2$^{tm1.1Mcbr}$, and WT mice received a control antibody (13C4) of the same IgG1 isotype. After treatment, mice were sacrificed, and lumbar spines and femurs were collected and fixed in 10% formalin for microCT and bone histomorphometry. Contralateral femurs of Crtap$^{-/-}$ mice were stored in −20° C. wrapped in saline soaked gauze until biomechanical testing was performed. Lungs of these Crtap$^{-/-}$ mice were equally inflated, collected and fixed as described for P10 mice. No blinding was possible during treatment, because 1D11 or control antibody were injected according to group allocation. In all subsequent analyses the investigators were blinded to genotype and treatment group.

Immunoblotting

Protein was extracted from snap frozen P3 calvaria samples, transferred to 300 μl lysis buffer (0.0625 M Tris-HCl pH 7.5, 2% SDS, 5 mM NaF, 2 mM Na$_3$VO$_4$ and RocheComplete proteinase inhibitor) and homogenized for 1 minute, followed by incubation at 95° C. for 40 minutes. The supernatant was transferred to Centrifugal Filter Units/Amicon Ultra 3K (Millipore) and centrifuged to concentrate the protein. The total protein concentration of the lysate was measured using the Micro BCA reagent (Pierce) following the manufacturer's directions. 40 μg of calvaria protein extracts were suspended in laemmeli buffer containing 5% β-mercaptoethanol and separated on Mini Protean TGX SDS-PAGE gels (gradient 4-20%; Bio-Rad) and transferred onto PVDF membranes for western blot analyses. PVDF membranes were incubated with pSmad2 monoclonal antibody (Cell Signaling #3108, 1:750 in TBST containing 5% BSA overnight), followed by secondary HRP-linked anti-rabbit antibody (GE, 1:5000 in TBST containing 5% BSA for 2 hours), treated with ECL Plus Western Blotting Detection System (GE) and exposed to X-ray film. Subsequently, antibodies were stripped from membranes using ReBlot Plus reagent (Millipore), and incubated with Smad2 monoclonal antibody (Cell Signaling #5339, 1:2000 in TBST containing 5% BSA overnight), followed by similar secondary antibody incubation and ECL mediated visualization. X-ray films were scanned and the density of each band was quantified using ImageJ software (National Institutes of Health).

Quantitative Real-Time PCR

Total RNA was extracted from snap frozen P3 mouse calvaria using Trizol reagent (Invitrogen). The Superscript III RT system (Invitrogen) was used to synthesize cDNA from total RNA according to the manufacturer's protocol. Quantitative RT-PCR was performed on a LightCycler.v 1.5 (Roche) using gene-specific primers and SYBR Green I reagent (Roche). β2-Microglobulin was used as the reference gene for normalizing cDNA concentrations.

In Vivo Bioluminescence Imaging

P10 Crtap$^{-/-}$ mice and wildtype littermates that expressed the TGFβ-reporter transgene (SBE-Luc mice) were injected with D-luciferin (Goldbio, 150 mg/kg, IP), anaesthetized with isoflurane, and imaged 10 minutes after injection using a bioluminescence imaging system (Xenogen).

Primary Osteoblast Culture, TGFβ-Reporter Cells

Bone marrow cells were isolated from tibias and femurs of approximately 2 month old Crtap$^{-/-}$ and wildtype mice and cultured in α-MEM supplied with 10% FBS, 100 U/mL penicillin and 100 ug/mL streptomycin. Media was changed every second day and unattached cells were discarded. After 7 days, the attached cells, defined as bone marrow stromal cells (BMSCs), were reseeded to 24-well plates at 2.5×10$^4$ cells per cm$^2$ and cultured in osteogenic medium (α-MEM, 10% FBS, 500 μM ascorbic acid, and 10 mM β-glycerophosphate) for 3 days. Conditioned medium was collected and incubated with PAI-luciferase reporter mink lung epithelial cells. After 24 hours, the cell lysates were collected for luciferase activity assays, which were measured using the Dual-Luciferase Reporter System (Promega). The results were normalized to the total protein amount quantified using the Micro BCA reagent (Pierce).

MicroCT, Bone Histomorphometry

Lumbar vertebrae and femurs were scanned using a Scanco μCT-40 microCT for quantification of trabecular and cortical bone parameters. Vertebral and femoral trabecular bone parameters were analyzed using the Scanco analysis software by manually contouring the trabecular bone of vertebral body L4 as well as the distal metaphyseal section of the femur. The cortical bone parameters at the center of the femoral midshaft were quantified using the automated thresholding algorithm included in the software.

Scanned undecalcified Crtap$^{-/-}$ mouse spine samples were then embedded in plastic for sectioning. Toluidine blue staining and TRAP staining was performed using standard protocols for visualization and quantification of Ob's and Oc's, respectively, using the Bioquant Osteo Image Analysis System.

Immunostaining and Histology

For immunohistochemistry, hind limbs of P5 mice were collected, fixed overnight in 4% paraformaldehyde and embedded in paraffin. After deparaffinization and rehydration, heat-induced antigen retrieval was performed (Dako, S1700) followed by treatment with hyaluronidase for 30 min (2 mg/ml; Sigma). Endogenous peroxidase was blocked using 3% hydrogen peroxide for 10 min. After incubation with blocking solution (3% normal goat serum, 0.1% BSA, 0.1% Triton X-100 in PBS), sections were incubated in antibodies for TGFβ1 (G1221, Promega) and decorin (LF- 113, kindly provided from Larry Fisher, National Institute of Dental and Craniofacial Research, Bethesda, MD, USA) for 60 min (1:25 dilution each in PBS, control samples were incubated in PBS only) at 37C, and subsequently incubated with secondary antibody (SuperPicTure Ploymer Detection kit, Invitrogen). Substrate DAB was added according to the manufacturer's recommendations and samples were dehydrated and mounted using Cytoseal XYL xylene based mounting medium (Thermo Scientific). Sections of WT and mutant littermates were processed at the same time. Images of the trabecular bone were taken with a light microscope (Axioplan 2, Zeiss) using identical exposure times for WT and mutant littermates.

Lungs of P10 and 16 week old Crtap$^{-/-}$ mice were equally inflated during tissue collection, fixed in 4% paraformaldehyde, and were paraffin embedded. Lungs of P10 Crtap$^{-/-}$ and wildtype mice were used for immunostaining for pSmad2. Briefly, paraffin sections were treated with xylene, rehydrated, and heated for 20 minutes for antigen retrieval (pH 6; Dako). Sections were then incubated in blocking solution (3% normal Donkey serum, 0.1% BSA, 0.1% Triton X-100 in PBS), and subsequently incubated with rabbit anti-pSmad2 antibody (1:500) (Cell signaling, #3108), donkey anti-rabbit secondary antibody conjugated to Alexa flour 594 (1:600) (Invitrogen), and mounted with Prolong Gold anti-fade reagent with DAPI (Invitrogen). Fluorescent images from these sections were taken using a Zeiss microscope (Axiovision Software) using identical exposure times.

For lung histology and morphometry of 16 week old mice, parasagittal sections were stained using a standard protocol for Hematoxylin and Eosin staining. The mean linear intercept (MLI) method was used to quantify the distance between alveolar structures. Briefly, 10 histological fields were captured per mouse at 20× magnification from all lobes of both lungs using a light microscope (Axioplan 2, Zeiss). The MLI was measured using modified ImageJ software (National Institutes of Health, modified by Paul Thompson). After manual removal of blood vessels, large airways and other nonalveolar structures, the software automatically thresholds the alveolar tissue in each image and overlays a line grid comprised of 1,353 lines with each line measuring 21 pixels over the image. The number of lines that intercepted alveolar structures was used to calculate the MLI.

Biomechanical Testing by 3-Point Bending

Crtap$^{-/-}$ and WT femurs were tested by three point bending using a span of 6 mm with an Instron 5848 device (Instron Inc., Norwood MA). All the femurs were tested wet at room temperature. They were preloaded to 1 N at a rate of 0.05 N/s for 5 seconds. Following the pre-loading, the femurs were loaded to failure at a rate of 0.1 mm/sec. Load and displacement data was captured at rate of 40 Hz by using BLUEHILL Software (Instron 5848).

To determine the Yield Point, a region was identified after the preload and before the maximum load on the load-displacement curve. This region was separated into 5 segments from which the fitted line of the segment with greatest slope was taken. Next, a 0.012 mm offset was implemented on the line. The point of intersection between the offset line and the load-displacement curve was the 0.012 Offset Yield Point. This yield point corresponded more closely to a 0.2% offset strain, which is commonly chosen in the literature. The elastic region was identified as the region from the completion of the preload to the Yield Point. The Post-Yield region was identified as the region from the Yield Point until the point at which the change in load exceeded −1N, indicating failure. The Elastic Displacement was the displacement during which specimen remained in the elastic region. The Post-Yield Displacement was the displacement during which the specimen remained in the Post-Yield region. The Total Displacement was calculated as the sum of the Elastic Displacement and the Post-Yield Displacement. Using the trapezoidal numerical integration method, Energy to failure was calculated as the area under the Load-Displacement curve. The Maximum Load was determined by finding the highest load value recorded by BLUEHILL, before the specimen failed. To calculate Stiffness, the Least Square fit method was applied to the steepest segment of the elastic region of the load-displacement curve. Stiffness was the slope of least square fit line. Geometric data (diameter and moment of inertia) obtained from microCT analysis of the femoral midshaft were utilized to calculate the intrinsic material properties: ultimate strength, toughness to failure and elastic modulus.

Serum Bone Turnover Markers

Serum osteocalcin (OCN) was quantified using the Mouse Osteocalcin EIA Kit from Biomedical Technologies Inc. C-terminal cross-linked telopeptide of bone collagen (CTX) was quantified using the RatLaps™ EIA Kit from Immunodiagnostic Systems Ltd. Both analyses were performed according to the manufacturer's protocols.

Collagen SDS-PAGE, Mass Spectrometry and Crosslinks Analyses

For mass spectrometry, type I collagen was prepared from Crtap$^{-/-}$ and wildtype tibiae. Bone was defatted with chloroform/methanol (3:1 v/v) and demineralized in 0.5 M EDTA, 0.05 M Tris-HCl, pH 7.5, all steps at 4° C. Bone were finely minced and collagen solubilized by heat denaturation (90° C.) in SDS-PAGE sample buffer. Collagen α-chains were cut from SDS-PAGE gels and subjected to in-gel trypsin digestion. Electrospray MS was performed on the tryptic peptides using an LCQ Deca XP ion-trap mass spectrometer equipped with in-line liquid chromatography (LC) (ThermoFinnigan) using a C8 capillary column (300 μm×150 mm; Grace Vydac 208 MS5.315) eluted at 4.5 μl min. Sequest search software (ThermoFinnigan) was used for peptide identification using the NCBI protein database.

Pyridinoline cross-links (HP and LP) were quantified by HPLC after hydrolyzing demineralized bone in 6N HCl.

Surface Plasmon Resonance Analysis

Surface plasmon resonance experiments were carried out using a BIACore X instrument (GE Healthcare Bio-Science Corp.). Purified native mouse tendon type I collagen from wild type and Crtap$^{-/-}$ mice were immobilized on a CM5 sensor chip by amide coupling at a concentration of about 0.05 ng/mm$^2$ (500 RU) and 0.08 ng/mm$^2$ (800 RU), respectively. The experiments were conducted at a flow rate of 10 μl/min and 20° C. in HBS-P buffer (10 mM Hepes buffer, pH 7.4, containing 150 mM NaCl and 0.005% Surfactant P20). Recombinant human decorin core protein (R&D systems) was injected onto both type I CM5 chips. The concentration of the stock solution of human decorin was determined by amino acid analysis. The binding response of decorin to wild type and Crtap$^{-/-}$ mouse type I collagen was normalized by the amounts of immobilized type I collagen on the CM5 sensor chips. Three concentrations of decorin were used (3, 5 and 12 μM), for each concentration the analysis was repeated three times. This experiment was performed twice with collagen isolated from different mice each time Statistical Methods Comparisons between two groups were performed using unpaired, two-tailed Student's t-tests. For comparisons between 3 groups, One Way Analysis of Variance (ANOVA) was performed if equal variance of groups was confirmed, followed by all pairwise multiple comparison using the Holm-Sidak method. If the equal variance test failed, Kruskal-Wallis One Way ANOVA on Ranks was performed, followed by all pairwise multiple comparison using the Tukey Test. A P value less than 0.05 was considered statistically significant for Student's t-test, ANOVA and Kruskal-Wallis One Way ANOVA on Ranks. For posthoc pairwise multiple comparisons, each P value was compared to a critical level depending on the rank of the P value and the total number of comparisons made to determine if differences between groups are significant. Sigma Plot V11.0 (Systat Software Inc.) was used for statistical analyses.

The effects of 1D11 on bone and lungs of OI mice were unknown at study start. To determine the initial sample size per group of mice we calculated that to detect a minimal difference of 20% in bone mass (BV/TV) by MicroCT between 1D11 and control treated OI mice with a 90% power, a group size of 8 mice is required.

Example 1: Altered TGFβ Signaling in Crtap$^{-/-}$ Calvaria

Figure 1B:
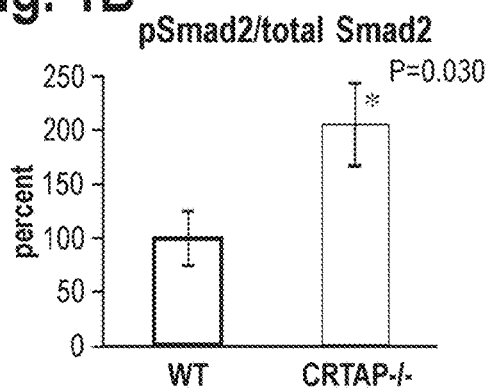
Figure 1C:
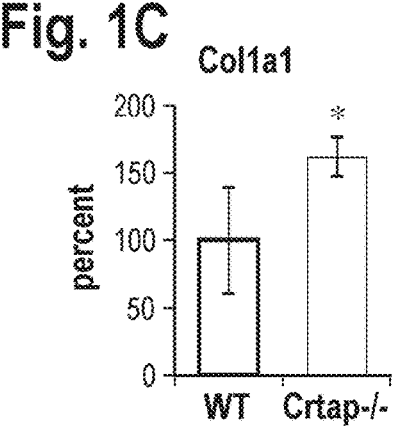
Figure 1D:
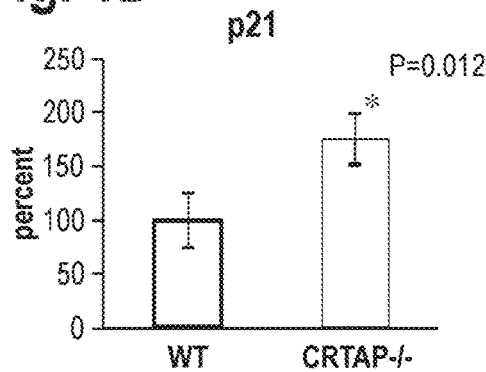
Figure 1E:
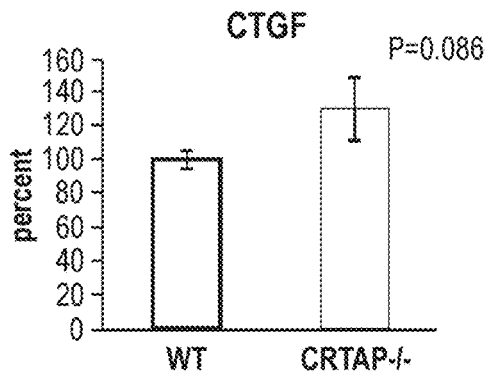
Figure 1F:
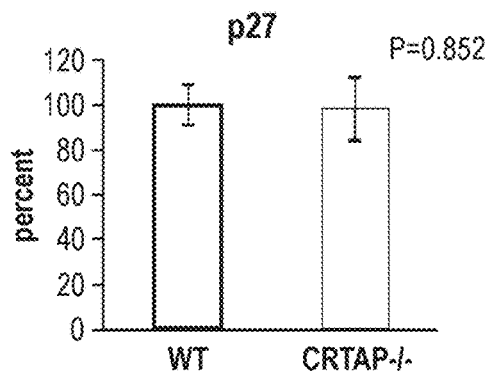

Crtap$^{-/-}$ mice and age-matched wild type (WT) littermate controls were analyzed for expression of activated pSmad 2, a member of the TGFβ signaling pathway, as well as other downstream targets of TGFβ. Calvaria bones were excised and RNA and protein were extracted and analyzed by Realtime-PCR and Western blot, respectively. As can be seen in FIGS. 1A and 1B, Crtap$^{-/-}$ mice had a 100% higher ratio of activated pSmad2 to total Smad2 compared to WT mice, as measured by Western blot and quantified by densitometry, indicating that TGFβ signaling is elevated in Crtap$^{-/-}$ mice. Transcriptional targets of TGFβ, such as Col1a1 and p21, were elevated compared to WT controls, as measured by RT-PCR and demonstrated in FIG. 1C and FIG. 1D, respectively. The pro-fibrotic ECM protein connective tissue growth factor (CTGF) was measured and found to be approximately 50% higher in Crtap$^{-/-}$ mice compared to WT controls, as determined by RT-PCR and demonstrated in FIG. 1E. As shown in FIG. 1F, RT-PCR analysis revealed that expression of the cyclin-dependent kinase inhibitor p27 was not altered in either the Crtap$^{-/-}$ or the WT mice.

Figure 2A:
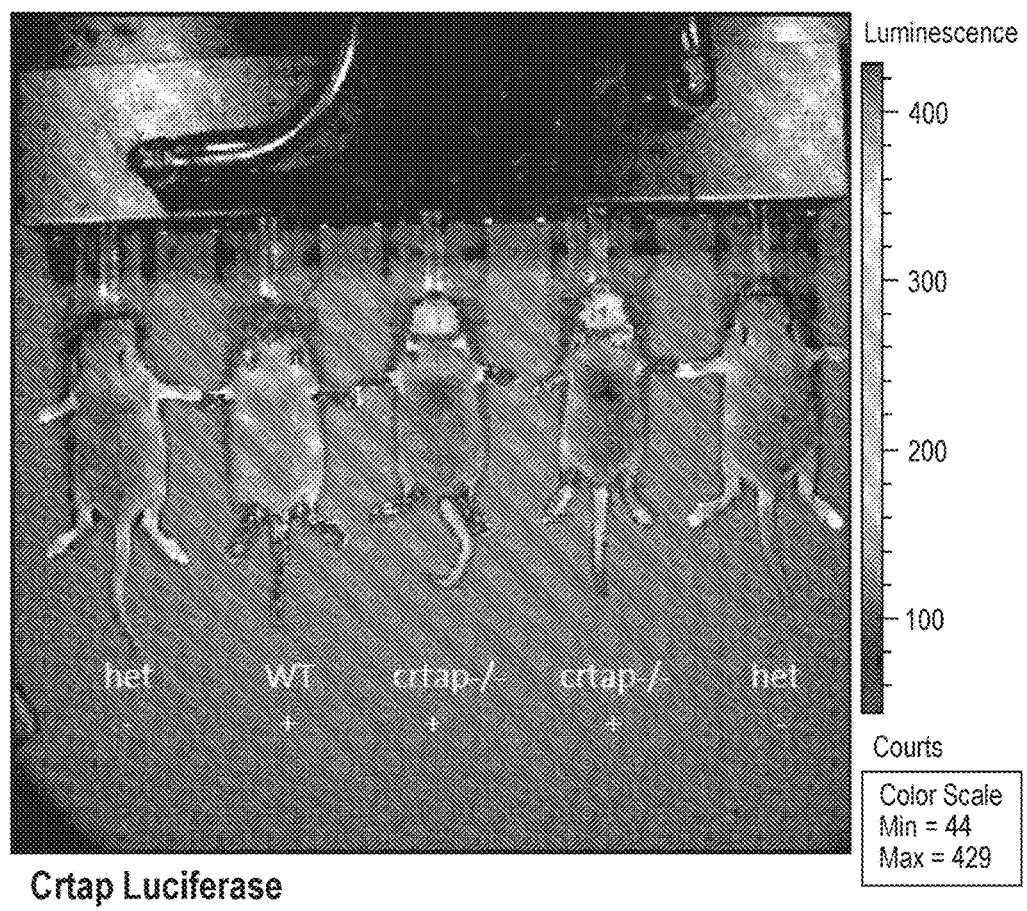
FIGS. 2A (luminescent picture) and 2B-C (graphs) show that Crtap$^{-/-}$ mice crossed with TGFβ reporter mice exhibit higher TGFβ activity compared to wild type controls.
Figure 2B:
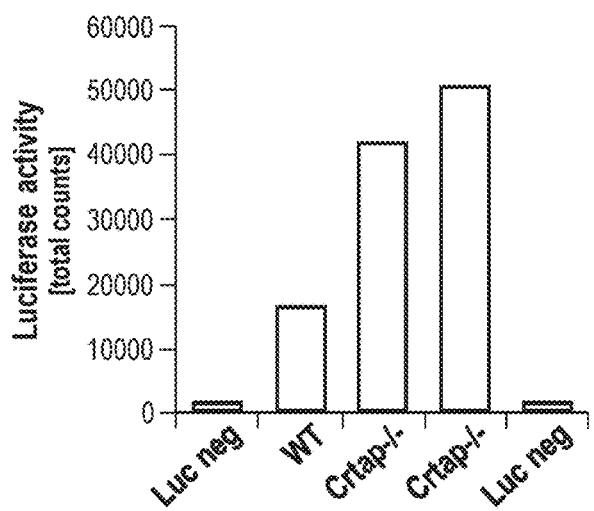

Example 2: Increased TGFb Activity in Crtap$^{-/-}$ Mice In Vivo and in Crtap$^{-/-}$ Osteoblastic Cells Crtap$^{-/-}$ mice were crossed to TGFβ reporter mice that express luciferase in response to activation of TGFβ signaling (Jackson Laboratory; B6.Cg-Tg(SBE/TK-luc)7Twc/J). P9 mice were injected with the substrate D-Luciferin (150 mg/kg) 10 minutes before imaging (Xenogen; IVIS camera system). As demonstrated in FIG. 2A, Crtap$^{-/-}$ mice had considerably higher luminescence in their tails, long bones, and calvaria compared to WT controls, indicating increased TGFb activity in Crtap$^{-/-}$ mice. FIG. 2B, quantification of luciferase activity at calvaria.

Figure 2C:
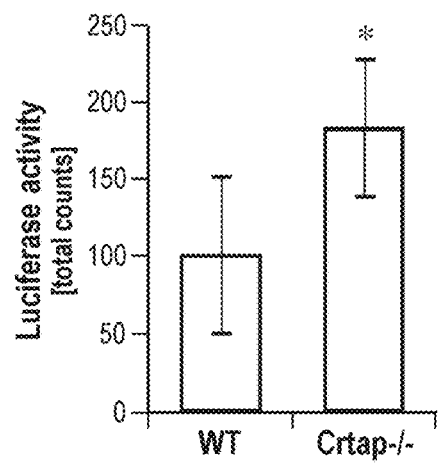

Bone marrow stromal cells (BMSCs) were isolated from Crtap$^{-/-}$ mice and WT mice, cultured under osteogenic conditions ex vivo, and the conditioned culture medium was analyzed for TGFβ activity using a cell line that expresses luciferase in response to activation of TGFβ signaling. As shown in FIG. 2C, conditioned medium from Crtap$^{-/-}$ BMSCs resulted in nearly a two-fold greater luciferase activity of the reporter cell line compared to BMSCs from WT mice. Together, these data indicate that TGFβ secretion and activity is elevated in the bones and osteoblastic cells of Crtap$^{-/-}$ mice.

Example 3: μCT Analysis of Crtap$^{-/-}$ Vertebrae

Figure 3:
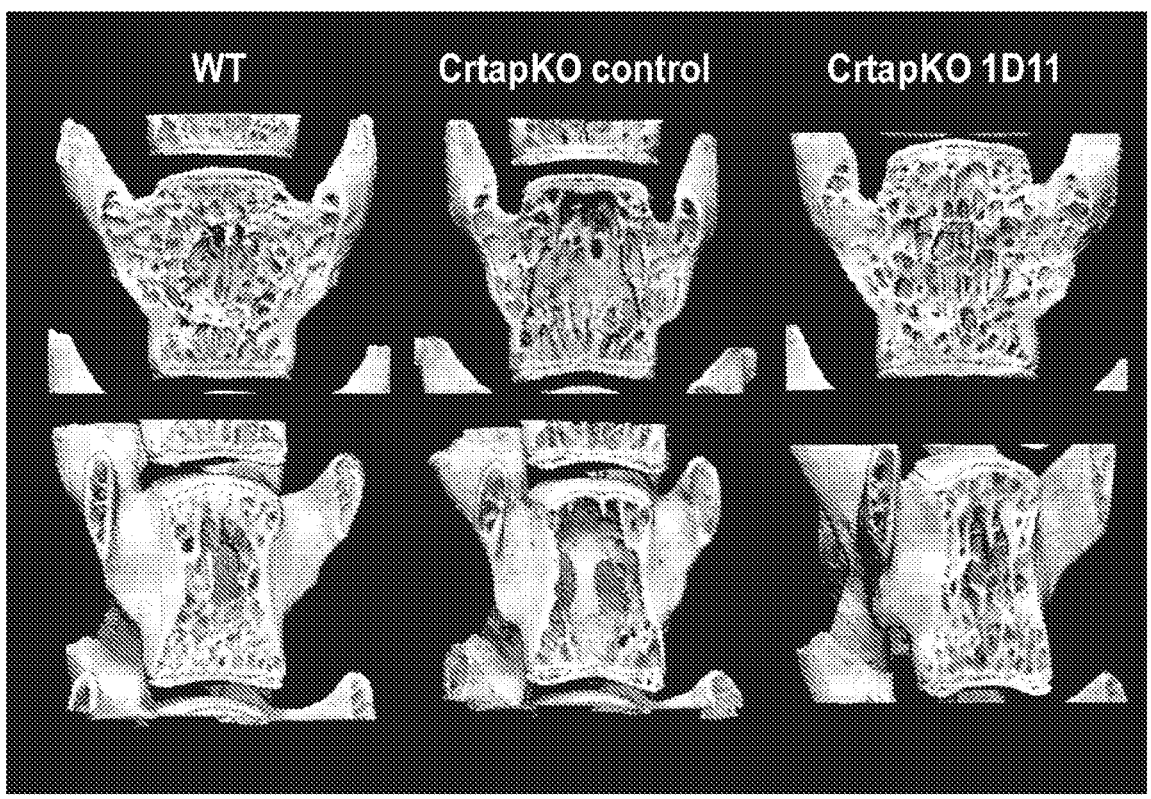
FIG. 3 is a μCT image of vertebrae from Crtap$^{-/-}$ mice treated with the mouse pan-specific anti-TGFβ antibody 1D11.

Adult 8 week old Crtap$^{-/-}$ mice (N=6 per group) were administered 1D11 (10 mg/kg, I.P., 3 times/week, 8 weeks total), a murine surrogate of the pan-specific antibody that binds to TGFβ comprising a heavy chain comprising the amino acid sequence of SEQ ID NO: 14 and a light chain comprising the amino acid sequence of SEQ ID NO: 15. An unrelated 13C4 antibody was administered to a separate group of Crtap$^{-/-}$ mice and WT mice as a control (N=6). The L4 vertebral bodies of 16 week old mice (treated from week 8-16) were imaged by μ-CT. MicroCT data of vertebral body L4 from 8 week old Crtap$^{-/-}$ mice (n=6 per group) that were treated with the TGFβ neutralizing antibody 1D11 (Genzyme; 10 mg/kg, I.P., 3 times/week) for 8 weeks and wild-type (WT) and control Crtap$^{-/-}$ mice that were treated with a control antibody (13C4-placebo) is shown in FIG. 3. As shown in FIG. 3, Crtap$^{-/-}$ vertebrae were cavernous compared to WT control vertebrae. However, 1D11 treatment result in a skeletal phenotype that was comparable to the WT condition.

Figure 4:
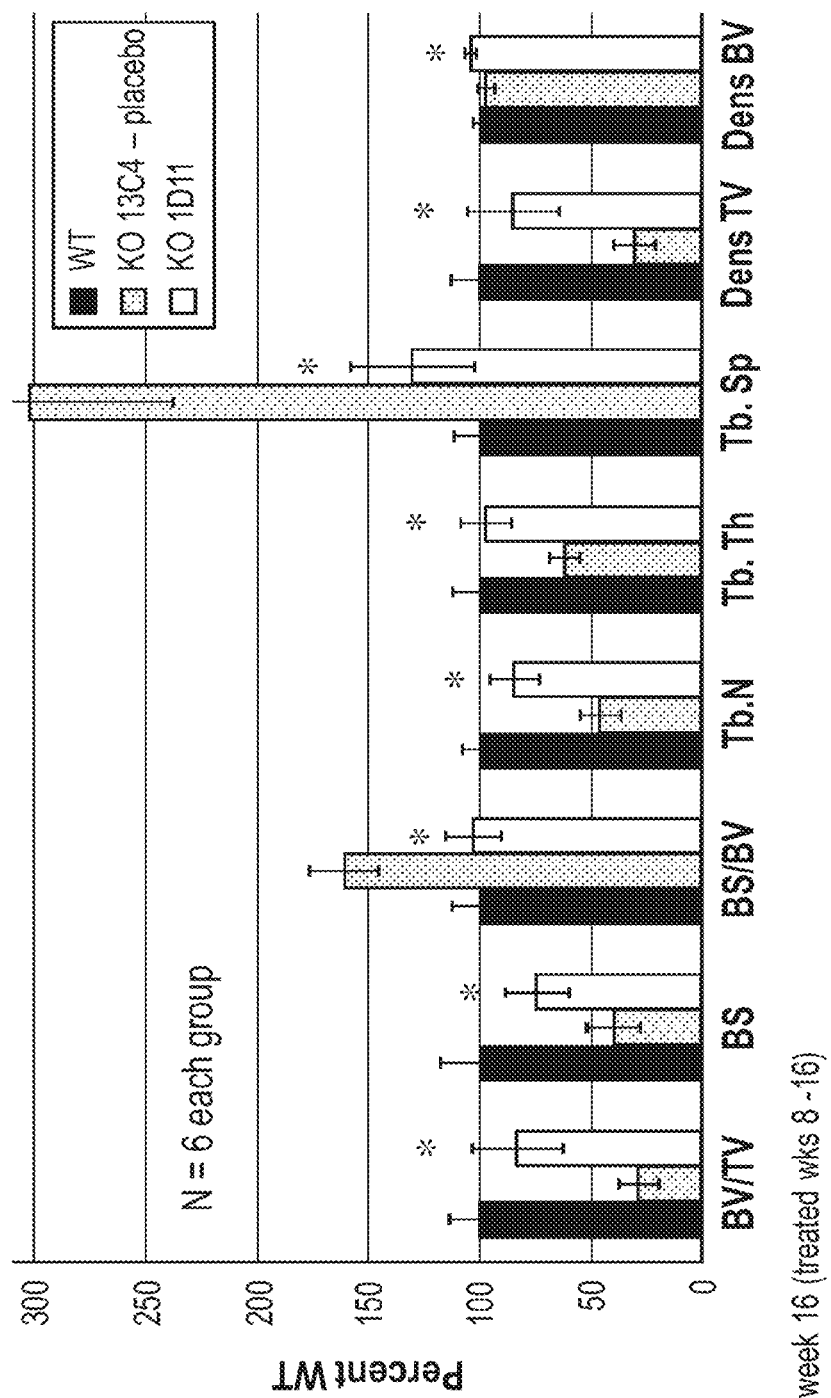
FIG. 4 is a graph that contains quantitative measurements of vertebrae from Crtap$^{-/-}$ mice treated with the mouse pan-specific anti-TGFβ antibody 1D11.

The data from FIG. 3 was quantified in FIG. 4, treatment with the pan-specific anti-TGFβ antibody rescued the skeletal phenotype of Crtap$^{-/-}$ mice. Vertebrae from treated Crtap$^{-/-}$ mice were statistically similar to WT control mice in measured parameters, including bone volume density (BV/TV), total bone surface (BS), bone surface density (BS/BV), trabecular number (Tb.N), trabecular thickness (Tb.Th), trabecular spacing (Tb.Sp), and total volume (Dens TV).

Example 4: Histomorphometry of Anti-TGFβ Treated Crtap$^{-/-}$ Vertebrae

Figure 5A:
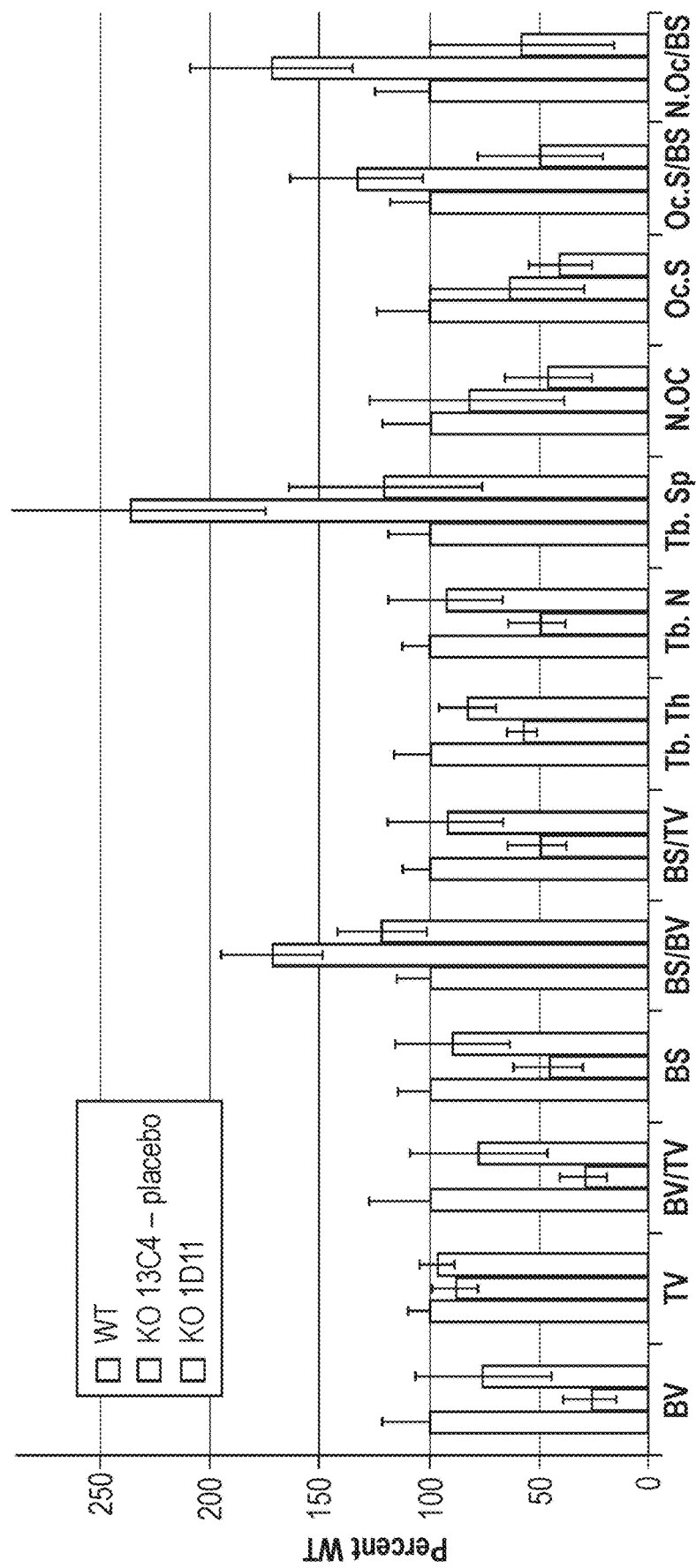
FIGS. 5A-B are a histomorphometric analysis of vertebrae from Crtap$^{-/-}$ mice treated with the mouse pan-specific anti-TGFβ antibody 1D11.
Figure 5B:
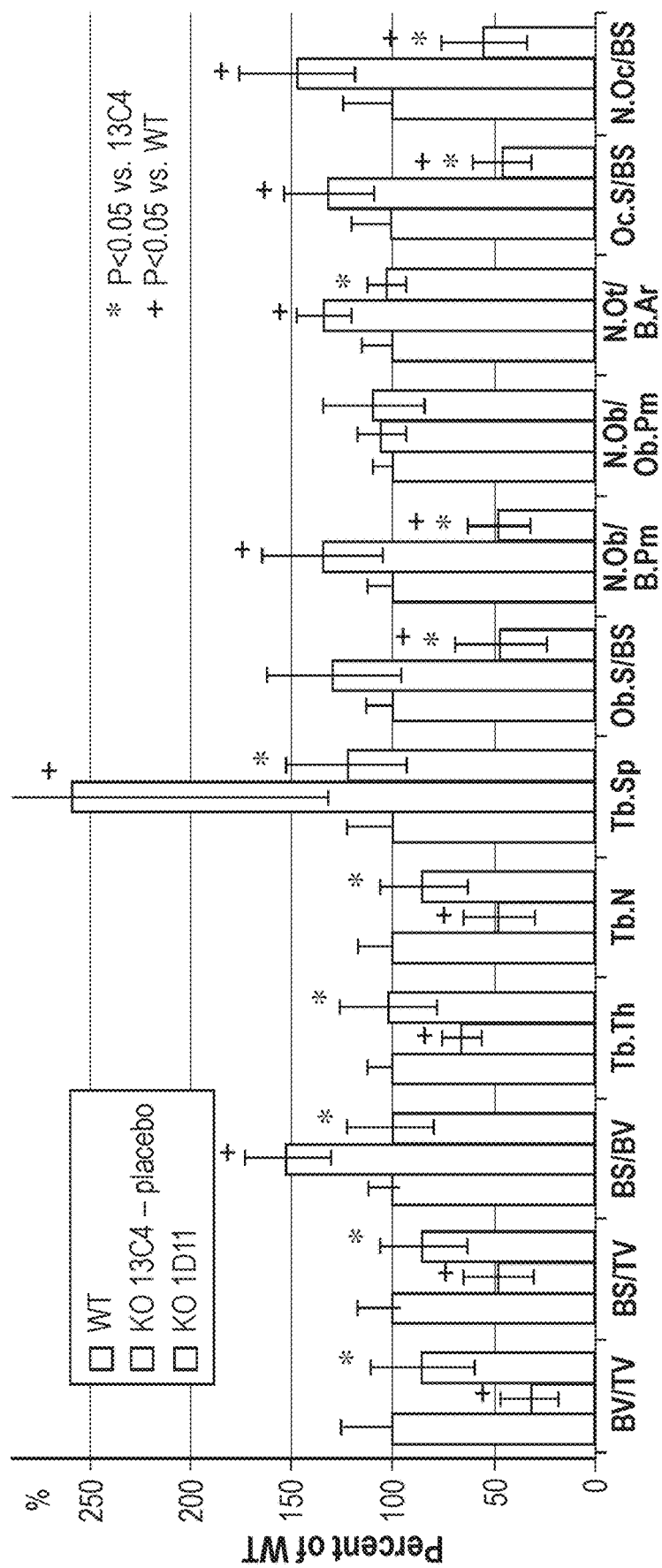

In addition to μ-CT, the vertebral bones of antibody-treated, placebo-treated, and WT mice were analyzed by histomorphometry. As shown in FIGS. 5A and 5B, μ-CT results were confirmed by histomorphometric analysis. In addition, tissue sections were stained for expression of the osteoclast marker TRAP. Analysis revealed that there were more osteoclasts covering more of the bone surface in Crtap$^{-/-}$ mice compared to WT controls (N.Oc/BS and Oc.S/BS), indicating increased osteoclastic activity. Treatment with the 1D11 anti-TGFβ reduced all osteoclast-specific parameters to below WT numbers. Thus, osteoclasts were identified as a potential target for TGFβ antibodies, and more specifically, pan-specific anti-TGFβ antibodies.

Example 5: Three-Point Bending Test of Anti-TGFβ Treated Crtap$^{-/-}$ Femurs

Biomechanical testing was performed on the excised femurs of 16 week old mice (after treatment from week 8-16) using a standard three-point bending test with an Instron 5848 device (Instron Inc., Norwood MA) with a 6 mm span, preloaded to 1N at a rate of 1N/s for 5 seconds. Following the pre-loading, femurs were compressed to failure at a rate of 0.1 mm/sec. Load and displacement data were captured at rate of 40 Hz by using BLUEHILL Software (Instron 5848).

Figure 6A:
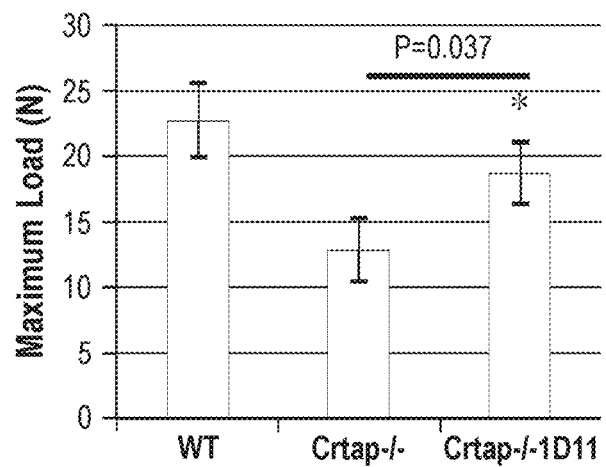
FIGS. 6A and 6B are graphs that demonstrates the biomechanical properties (FIG. 6A—maximum load, and FIG. 6B—stiffness) of femurs from Crtap$^{-/-}$ mice treated with the mouse pan-specific anti-TGFβ antibody 1D11, as determined by a three-point bending test.
Figure 6B:
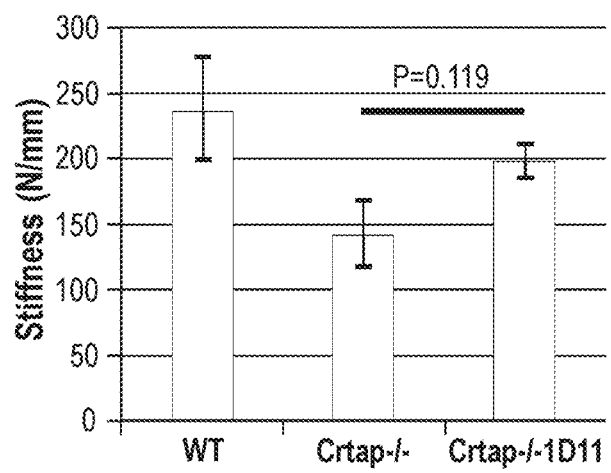

As demonstrated in FIG. 6, Crtap$^{-/-}$ mice femurs were less stiff and were able to withstand a significantly smaller maximal load compared to WT control mice. Femurs of 1D11 treated Crtap$^{-/-}$ mice showed a significant improvement of the maximum load, and a trend to an increased stiffness compared to control crtap$^{-/-}$ mice.

Thus, treatment with the 1D11 pan-specific anti-TGFβ antibody quantitatively, qualitatively, and biomechanically restored the skeletal phenotype of Crtap$^{-/-}$ mice.

Example 6: Inhibition of TGFβ Signaling with 1D11 Ameliorates the Lung Phenotype Crtap$^{-/-}$ mice have a generalized connective tissue disease manifested by low bone mass, glomerulosclerosis, and pulmonary dysplasia (Baldridge et al.; PloS One, 5(5): e10560 (2010)). Increased TGFβ expression was seen the lungs of Crtap$^{-/-}$ mice, as evidenced by positive immunostaining for pSmad2 and demonstrated in FIG. 7A. Histologically, Crtap$^{-/-}$ mice exhibited increased distal airway space compared to WT mice, as shown in FIG. 7B. 1D11 treatment (10 mg/kg, IP, 3×/week for 8 weeks) reduced pSmad2 expression in Crtap$^{-/-}$ mice and reduced the distal airway space and ameliorated the lung phenotype, as demonstrated in FIG. 7A and FIG. 7B and quantified in FIG. 7C (*P<0.05 vs. control Crtap$^{-/-}$; 10 images analyzed per mouse, n=8 mice per group).

Example 7: Decorin Expression in Crtap$^{-/-}$ Lungs

Figure 8:
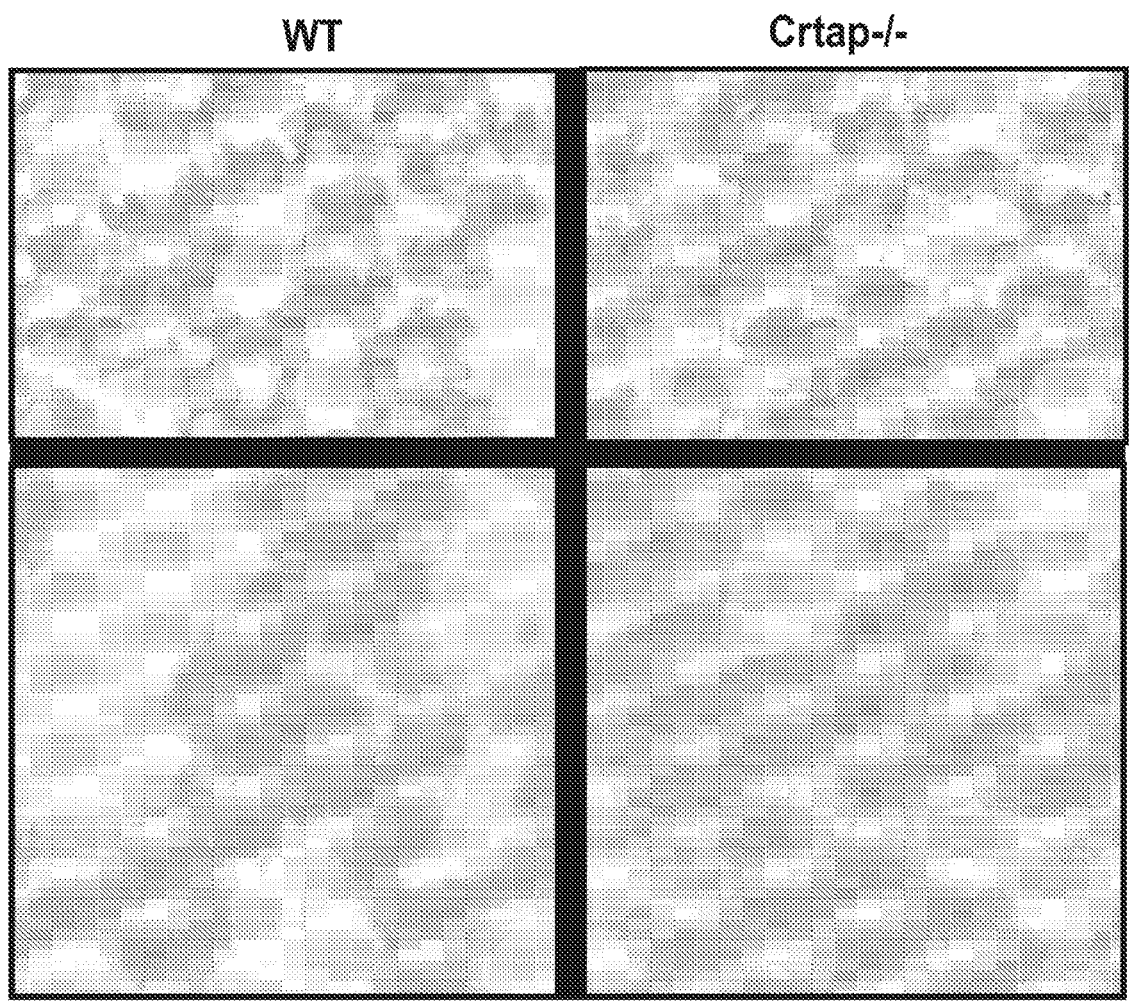
FIG. 8 are micrograph images of Crtap$^{-/-}$ and WT lungs stained with an anti-decorin antibody.

Transcriptional regulators of TGFβ expression were investigated in order to understand the basis of dysregulated TGFβ signaling in the bones and lungs of Crtap$^{-/-}$ mice. A major class of extracellular proteins that can regulate TGFβ in ECM include the small leucine rich proteoglycans (SLRP), such as decorin. Immunostaining revealed increased expression of decorin in Crtap$^{-/-}$ lungs compared to WT control lungs, as shown in FIG. 8.

Figure 9:
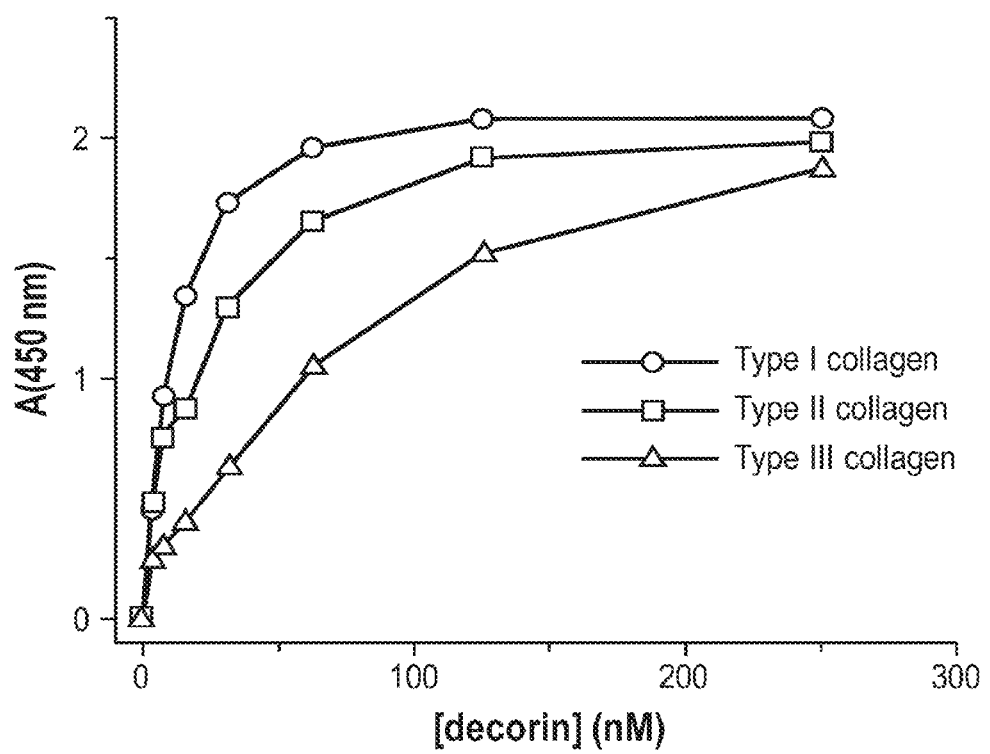
FIG. 9 is a graph depicting a decorin binding assay.

As decorin is a regulator of mature TGFβ, this finding suggests that altered post-translational modification of collagen, as occurs in OI, alters the interactions of ECM proteins, including SLRPs. Decorin binds to hydroxyproline sites, such as the one located at amino acid residue 396 of type-I and type-II collagens, which are absent in Crtap$^{-/-}$ mice. A decorin binding assay was performed to determine whether decorin binding may be altered in OI, and whether this may be at least partly responsible for the phenotypes observed in Crtap$^{-/-}$ bones and mice. As shown in FIG. 9, decorin binding to 3-hydroxylated collagen peptides (as in type I and II collagen) was greater than collagen peptides without 3-hydroxylation (as in type III collagen).

Example 8: Increased TGFβ Signaling is a Common Mechanism in Osteogenesis Imperfecta OI is characterized by brittle bones, low bone mass, bone deformities and fractures. In addition, extraskeletal manifestations including lung abnormalities contribute substantially to morbidity and mortality. Most cases of OI are caused by autosomal dominant mutations in the genes encoding type I collagen (COL1A1 and COL1A2). In recent years, mutations in additional genes encoding the proteins involved in the post-translational modification of collagen have been identified as causing recessive forms of OI. The first described was in cartilage associated protein (CRTAP), a member of the prolyl-3-hydroxylase complex that is responsible for 3-hydroxylation of proline residue 986 α1(I) in type I collagen. Hypomorphic CRTAP mutations lead to partial loss of 3-hydroxyproline (3Hyp) in fibrillar collagen as well as overmodification of other residues and result in recessive OI type VII, which clinically overlaps with dominant forms of severe OI. The physiological function of 3Hyp is not completely understood, but biochemical studies suggest that it may be involved in collagen-protein interactions, rather than negatively affecting collagen stability.

The ECM is an important reservoir for signaling molecules and their regulators. In bone, TGFβ acts as a central coordinator of bone remodeling by coupling the localized activity of bone resorbing osteoclasts and bone forming osteoblasts. TGFβ is abundantly produced by osteoblasts, is secreted predominantly in inactive latent forms, and is deposited into the bone matrix. Here, it can be released and activated during bone resorption by osteoclasts. As an additional level of regulation, active TGFβ can be bound by proteoglycans, which modulate its bioactivity in association with collagen fibrils. Because type I collagen is the most abundant component of the ECM in bone, this raises the intriguing hypothesis that the alteration of collagen structure observed in OI not only increases bone fragility, but also affects the signaling reservoir function of the bone matrix. Interestingly, Crtap$^{-/-}$ mice show phenotypic overlap with animal models of increased TGFβ signaling. For example, TGFβ overexpression results in low bone mass. In addition, Crtap$^{-/-}$ mice exhibit an enlargement in alveolar airway space in lungs, which is similar to that observed in a mouse model of Marfan syndrome, where increased TGFβ signaling has been shown to be a major contributor to the lung pathology. Therefore, the status of TGFβ signaling was studied in the Crtap$^{-/-}$ mouse model if recessive OI.

To assess the status of TGFβ signaling in bone, the expression levels of TGFβ target genes in calvarial bone of Crtap$^{-/-}$ mice were evaluated. Compared with wild type (WT) samples, Crtap$^{-/-}$ bone showed an increased expression of the TGFβ downstream targets p21 (cyclin-dependent kinase inhibitor 1), PAI-1 (plasminogen activator inhibitor-1), and Col1a1, consistent with elevated TGFβ activity (FIG. 10A). To confirm increased activation of the intracellular TGFβ signaling pathway, the status of Smad2, an intracellular second messenger protein, which becomes phosphorylated after activation of TGFβ receptors, was evaluated. Consistent with target gene expression, immunoblot analyses demonstrated a higher ratio of phosphorylated Smad2 (pSmad2) to total Smad2 in bone samples of Crtap$^{-/-}$ mice, indicating increased TGFβ signaling (FIGS. 10B and 10C).

To determine whether these static measures reflect increased TGFβ activity in vivo, Crtap$^{-/-}$ mice were intercrossed with TGFβ-reporter mice expressing luciferase under control of TGFβ-responsive Smad binding elements (SBE-Luc mice). Compared with WT/SBE-Luc littermates, Crtap$^{-/-}$/SBE-Luc mice showed an increase in bioluminescence of areas over skeletal structures, indicating increased TGFβ activity in vivo (FIG. 10D). In 3 litters, Crtap$^{-/-}$ mice show a mean 2.86 fold (SD±0.34) bioluminescence signal at the head/calvaria compared with WT mice. Moreover, in order to test whether the increased TGFβ/Smad signaling associated with loss of Crtap is intrinsic to bone, i.e., tissue autonomous, bone marrow stromal cells (BMSCs) were differentiated to osteoblastic cell in vitro. By using a TGFβ reporter cell line, it was found that conditioned medium from Crtap$^{-/-}$ BMSCs exhibited higher TGFβ activity compared with medium from WT BMSCs (FIG. 10E). Together, these findings indicate that loss of Crtap enhances TGFβ signaling in bone in a tissue autonomous fashion.

Patients with severe OI can also exhibit intrinsic lung abnormalities, and respiratory failure is one of the leading causes of death in these individuals. Interestingly, Crtap$^{-/-}$ mice show a diffuse increase in alveolar airway space, a feature associated with increased TGFβ signaling in other developmental models. Accordingly, lungs of Crtap mice showed increased intracellular staining for pSmad2 in alveolar cells, indicating that the increased TGFβ activity is also present in extraskeletal tissues (FIG. 10F).

Figure 11A:
FIGS. 11A-D are a group of photos and graphs showing phenotypic correction of Crtap$^{-/-}$ mice after treatment with the TGFβ neutralizing antibody 1D11.
Figure 11B:
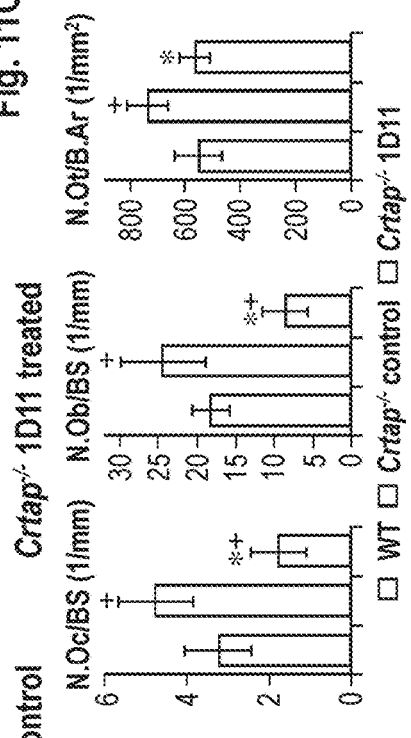
Figure 14:
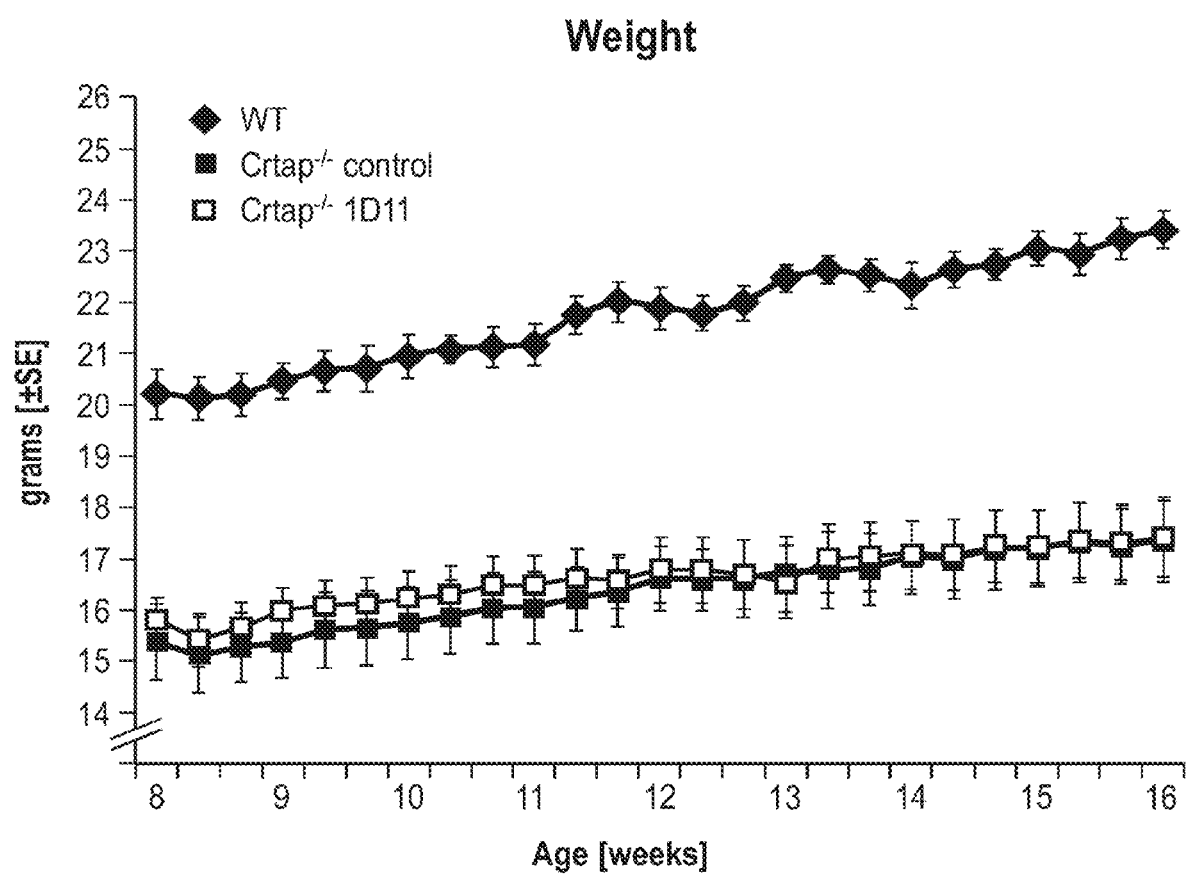
FIG. 14 is a weight curve graph, which shows a reduced weight of Crtap$^{-/-}$ mice compared with WTs during the study period (p<0.05 for all time points, means±SEs are shown). No statistically significant difference in weight was observed in 1D11-treated Crtap$^{-/-}$ mice compared to control Crtap$^{-/-}$ mice.
Figure 15B:
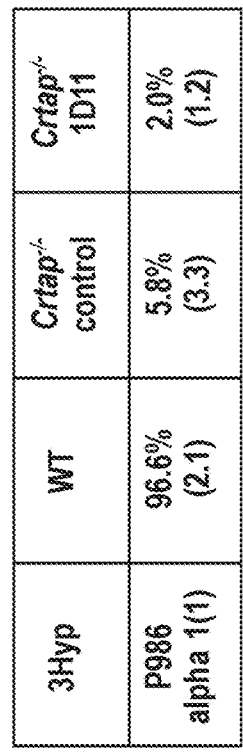
FIGS. 15A-C are a series of graphs and tables showing no effect of TGFβ inhibition on the abnormal type I collagen post-translational modification in Crtap$^{-/-}$ mice.
Figure 15C:
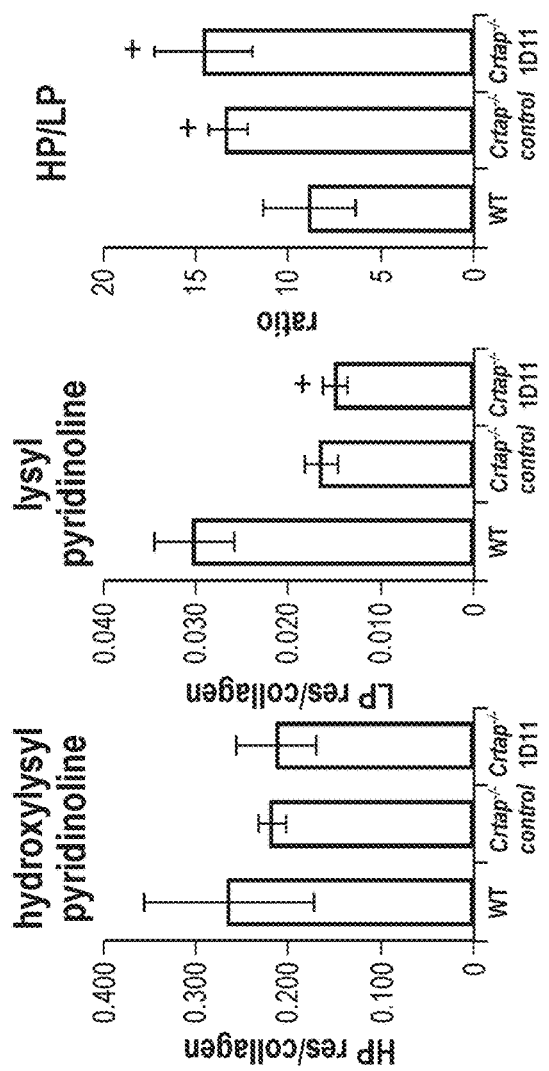
Figure 15A:
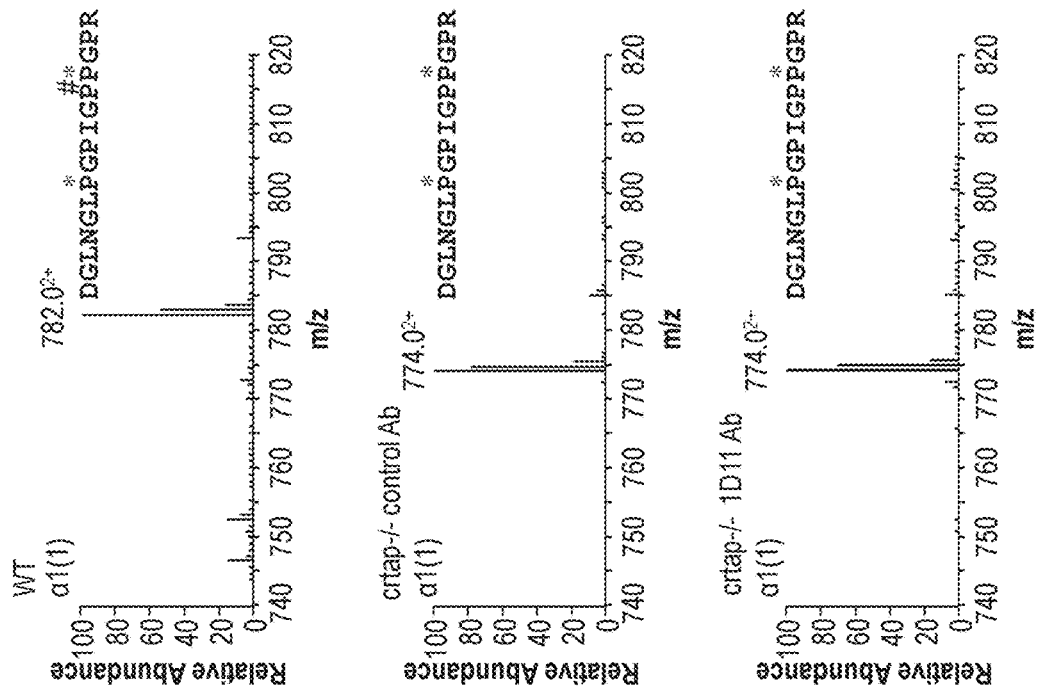
Figure 16A:
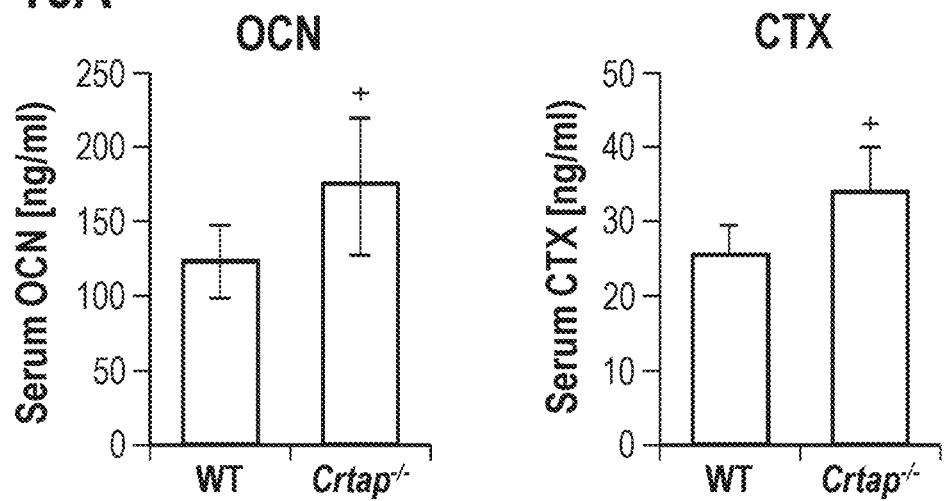
FIGS. 16A-B are a series of graphs showing serum bone-turnover markers osteocalcin (OCN) and C-terminal cross-linked telopeptide of bone collagen (CTX) at start (FIG. 16A=8 weeks of age) and end of the treatment study (FIG. 16B=16 weeks of age).
Figure 16B:
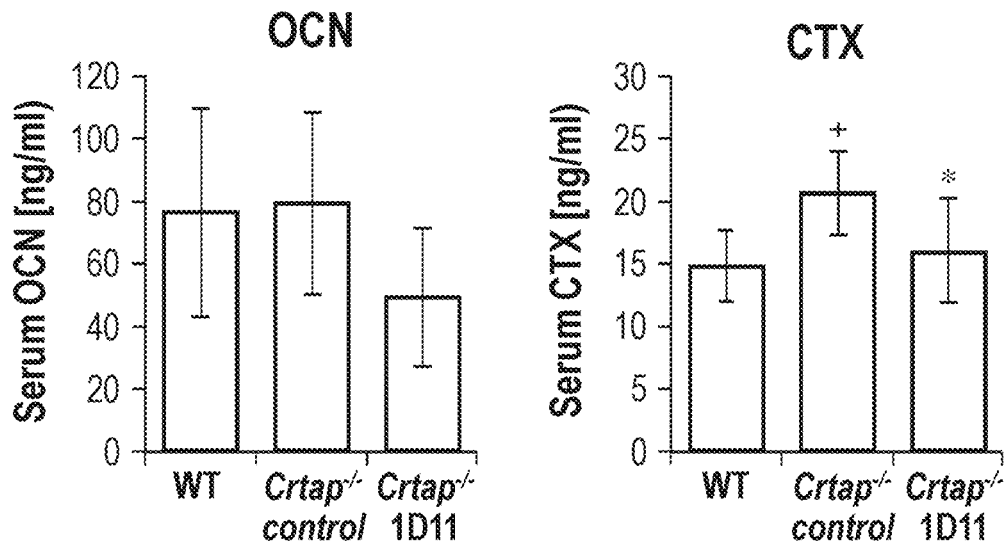

To understand whether increased TGFβ signaling represents a causal mechanism contributing to the bone and lung phenotypes in Crtap$^{-/-}$ mice, a rescue experiment was performed with a pan-TGFβ neutralizing antibody (1D11). Eight week old Crtap$^{-/-}$ mice were treated with 1D11 for 8 weeks; control Crtap$^{-/-}$ and WT mice received a non-specific control antibody (13C4). 1D11 did not significantly change body weight of the treated Crtap$^{-/-}$ mice, indicating that TGFβ inhibition did not affect the general nutritional status (FIG. 14). In addition, mass spectrometric and cross-links analyses showed that 1D11 did not significantly change the status of type I collagen P986 3-hydroxylation or collagen crosslinks in Crtap$^{-/-}$ mice, suggesting that dysregulated TGFβ signaling is a consequence of the altered molecular collagen structure, and not directly involved in intracellular collagen processing or extracellular fibril assembly (FIG. 15). Crtap$^{-/-}$ mice exhibit a reduced bone mass and abnormal trabecular bone parameters (FIGS. 11A and 11B). MicroCT imaging analysis of vertebrae demonstrated that compared with control Crtap$^{-/-}$ mice, TGFβ inhibition significantly improved trabecular bone parameters, including bone volume/total volume, trabecular number and trabecular thickness to near WT levels (FIGS. 11A and 11B, and FIG. 17). Similar beneficial effects were observed in femoral trabecular bone in Crtap mice, where TGFβ inhibition significantly improved trabecular bone parameters (FIG. 18). The effects of TGFβ inhibition on the skeleton with 1D11 have been reported previously in WT mice and in Es1-1$^{-/-}$ mice11, a model with increased TGFβ activity due to a defect in normal TGFβ maturation. While 1D11 moderately increased trabecular BV/TV by 33% in the spine in WT mice, Es1-1$^{-/-}$ mice exhibited an 106% increase in BV/TV. This suggested that targeting TGFβ in a pathophysiological situation where it is increased in the skeleton, could lead to a relatively more pronounced positive effect. In the present study, 1D11 increased the trabecular BV/TV at the spine by 235% in Crtap$^{-/-}$ mice, supporting that the dysregulated TGFβ signaling is an important contributor of the low bone mass in Crtap$^{-/-}$ mice. At the femur midshaft, the parameters of cortical architecture including cortical thickness, diameter, cross-sectional area and cross-sectional moments of inertia in Ctrap$^{-/-}$ mice were significantly reduced compared to WT mice. Following 1D11 treatment, these parameters were no longer significantly different from WT mice (FIG. 19). To test if these changes in cortical and trabecular bone translated into improved bone strength, biomechanical testing of the femurs by 3-point bending was performed. It was found that TGFβ inhibition was able to increase maximum load and ultimate strength in the treated Crtap$^{-/-}$ mice, indicating improved whole bone and tissue strength and improved resistance to fracture. However, 1D11 treatment had no effects on the increased brittleness of the OI bone, as indicated by the reduced post-yield displacement in both control and 1D11 treated Crtap$^{-/-}$ mice (FIG. 20). This likely reflects the inherent abnormal mineralization associated with altered collagen structure. Taken together, these findings indicate that increased TGFβ signaling is major contributor to the bone phenotype in recessive OI resulting from Crtap deficiency and that inhibition of dysregulated TGFβ signaling restores bone mass, microstructural parameters and improves whole bone strength.

Figure 11C:
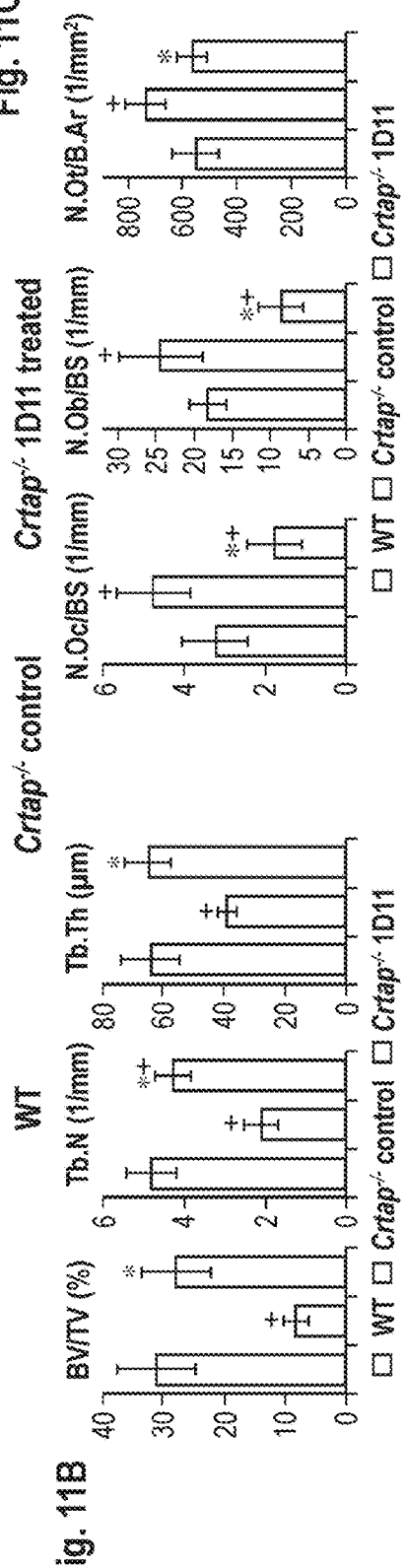

To understand the effects of TGFβ inhibition in Crtap$^{-/-}$ mice at the cellular level, histomorphometric analyses on treated mice was performed. In sections of vertebral bodies in this study it was found increased osteoclast (Oc) and osteoblast (Ob) numbers per bone surface in control Crtap$^{-/-}$ compared to WT mice, indicating increased bone remodeling in the spine (FIG. 11C and FIG. 21). Consistently, the serum bone turnover markers osteocalcin (OCN) and C-terminal cross-linked telopeptide of bone collagen (CTX) were elevated in 8 week old (OCN and CTX) and 16 week old (CTX only) control Crtap$^{-/-}$ mice (FIG. 19). Similar changes in the cellular composition of bone have been described in patients with dominant and recessive OI, showing increased Oc and Ob numbers consistent with an increased bone turnover. Interestingly, mouse models of increased TGFβ signaling also show low bone mass with increased osteoclastic bone resorption and abnormal bone remodeling. Most reports of the effects of TGFβ on bone cells are consistent with a model where TGFβ can stimulate the recruitment and initial differentiation of Oc and Ob precursors at the site of bone repair, followed by insulin-like growth factor 1 (IGF-1) mediated Ob differentiation. However, at persistently high doses, TGFβ can inhibit Ob differentiation by repressing the differentiation factor RUNX2. Given the crucial effects on Oc/Ob interaction, fine tuning of TGFβ availability is a key factor for the local coupling of bone resorption with formation during bone remodeling and its imbalance can lead to significant bone pathology.

In contrast to the findings in control Crtap$^{-/-}$ mice, bone sections of Crtap$^{-/-}$ mice treated with 1D11 revealed reduced Oc and Ob numbers, which were even lower than the values measured in the WT mice, indicating a supraphysiologic suppression of dysregulated bone remodeling as a result of TGFβ inhibition at the dose of 1D11 used in this experiment (FIG. 11C). Consistent with an earlier report, the observation of a reduction of Oc's and Ob's below WT levels also underscores the physiological requirement of local amounts of TGFβ to normally coordinate Oc's and Ob's during the bone remodeling process. Our findings are different from previous studies in WT mice, where 1D11 treatment reduced Oc numbers but increased Ob numbers. This may reflect distinct cellular effects of TGFβ inhibition in a pathophysiological situation with increased TGFβ signaling and increased bone remodeling compared with normal bone in WT mice. TGFβ has been shown to inhibit differentiation of osteoblast precursor cells, and increased TGFβ signaling could thereby lead to a higher proportion of immature osteoblast lineage cells. On the other hand, an increased number or higher proportion of immature Ob's on the bone surface could result in an increased amount of secreted TGFβ by these cells. The finding that TGFβ inhibition with 1D11 significantly reduces the increased Ob numbers in Crtap$^{-/-}$ mice suggests that the increased TGFβ signaling causally contributes to the increase in osteoblast lineage cells.

In addition to the findings regarding Oc and Ob numbers, greater osteocyte (Ot) numbers per bone area in control Crtap$^{-/-}$ mice were observed, which were reduced to levels comparable with those of WT mice in 1D11 treated Crtap$^{-/-}$ mice (FIG. 11C and FIG. 21). In OI patients, an increased Ot density has been observed in individuals with more severe forms of the disease, likely reflecting the presence of immature primary bone due to a defect in physiological maturation in OI bone. Consistent with our hypothesis that increased TGFβ signaling contributes to the bone pathology in OI, overexpression of TGFβ in WT mice similarly results in an increased Ot density. As a possible explanation, TGFβ can inhibit Ob apoptosis during the transition of Ob's to Ot's, and thereby lead to an increased Ot density. Collectively, these findings indicate that increased TGFβ signaling contributes to a high bone turnover status and impaired bone maturation in Crtap$^{-/-}$ mice and that inhibition of dysregulated TGFβ signaling reverses these cellular alterations.

Given these crucial effects on Oc/Ob interaction, fine tuning of TGFβ availability is a key factor for the local coupling of bone resorption with bone formation during bone remodeling and its imbalance can lead to significant bone pathology. Our findings indicate that inhibition of dysregulated TGFβ signaling in Crtap$^{-/-}$ mice restores bone mass as well as microstructural parameters, improves whole bone strength, and reverses the cellular alterations observed in Crtap$^{-/-}$ mice. Therefore, dysregulation of TGFβ signaling is an important contributor to the bone phenotype in this mouse model of recessive OI.

Figure 11D:
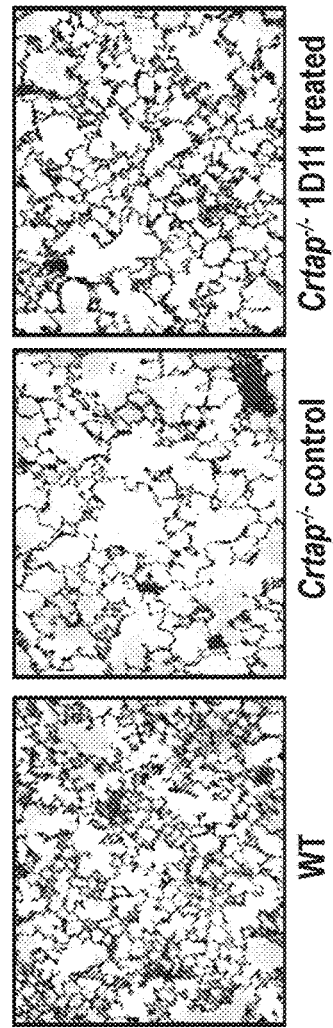
Figure 11E:
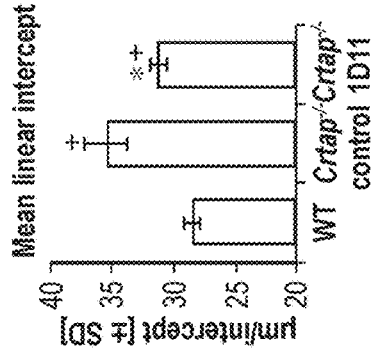
FIG. 11E is a graph showing quantification of the distance between alveolar structures by the mean-linear-intercept (MLI) method, which demonstrates a significant reduction of the distal airway space in 1D11-treated Crtap$^{-/-}$ mice compared with control antibody-treated Crtap$^{-/-}$ and WT mice. Results are shown as means±SDs, n=8 mice per group, 10 images analyzed per mouse, *p<0.05 for Crtap$^{-/-}$ 1D11 vs. Crtap$^{-/-}$ control, +p<0.05 for Crtap$^{-/-}$ vs. WT.

We were also interested in whether TGFβ inhibition affected the lung phenotype of Crtap$^{-/-}$ mice. Lungs of control Crtap$^{-/-}$ mice show an increase in the distal airway space compared with WT mice (FIG. 11D). Interestingly, lungs of Crtap$^{-/-}$ mice treated with the TGFβ neutralizing antibody showed a 60% improvement in the distance between alveolar structures (FIGS. 11D and 11E). This finding indicates that excessive TGFβ signaling is also an important pathogenic contributor to the lung abnormalities present in Crtap$^{-/-}$ mice. Increased TGFβ signaling has been linked to developmental pulmonary abnormalities as well as disease in mature lungs. For example, TGFβ overexpression in lungs results in impaired lung development with areas of enlarged airway space and increased TGFβ signaling is a contributing pathomechanism in lung abnormalities in Marfan syndrome as well as in the development of emphysema and bronchial asthma. Our results indicate that excessive TGFβ signaling is an important pathogenic contributor to the lung abnormalities present in Crtap$^{-/-}$ mice. Given the partial rescue of the lung phenotype with 1D11 in Crtap$^{-/-}$ mice, it is possible that dysregulated TGFβ signaling affects pulmonary tissue development when the anatomic structures are established, in addition to maintaining lung tissue at later stages when TGFβ inhibition is able to ameliorate the phenotype.

The next question asked was how alterations in collagen due to loss of Crtap (leading to the loss of 3Hyp at P986 and post-translational over modification of collagen) result in dysregulated TGFβ signaling. Biochemical analyses indicate that collagen prolyl-3-hydroxylation does not fundamentally affect the stability of collagen molecules, but instead it may affect collagen-protein interactions. An attractive hypothesis is that loss of 3Hyp could affect collagen interaction with small leucine-rich proteoglycans (SLRPs). SLRPs are known to bind to both type I collagen as well as TGFβ, and thereby modulate TGFβ activity. For example, the SLRP decorin is able to inhibit distinct effects of TGFβ in osteosarcoma cells whereas it enhances TGFβ activity in preosteoblastic cells. The binding region of decorin on type I collagen is suggested to center at residues 961/962 of the triple helical domain, which is located in close proximity to the P986 residue, that is unhydroxylated in OI due to Crtap deficiency. Therefore, it is possible that the P986 3Hyp position marks an interacting site for the binding of decorin to type I collagen, thereby mediating the sequestration of mature TGFβ to collagen.

Figure 12A:
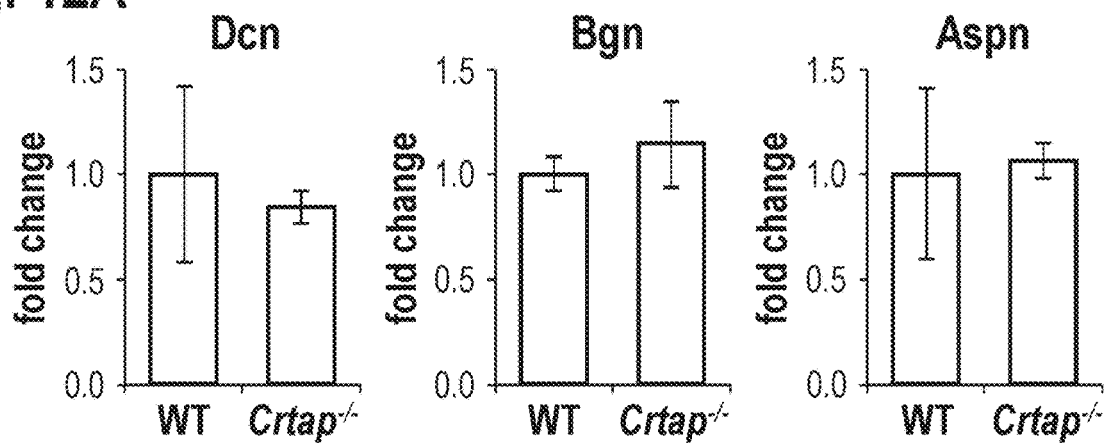
FIGS. 12A-B are a series of graphs that show that decorin binding to type I collagen overlaps the P986 3Hyp site and is reduced in type I collagen of Crtap$^{-/-}$ mice.
Figure 12B:
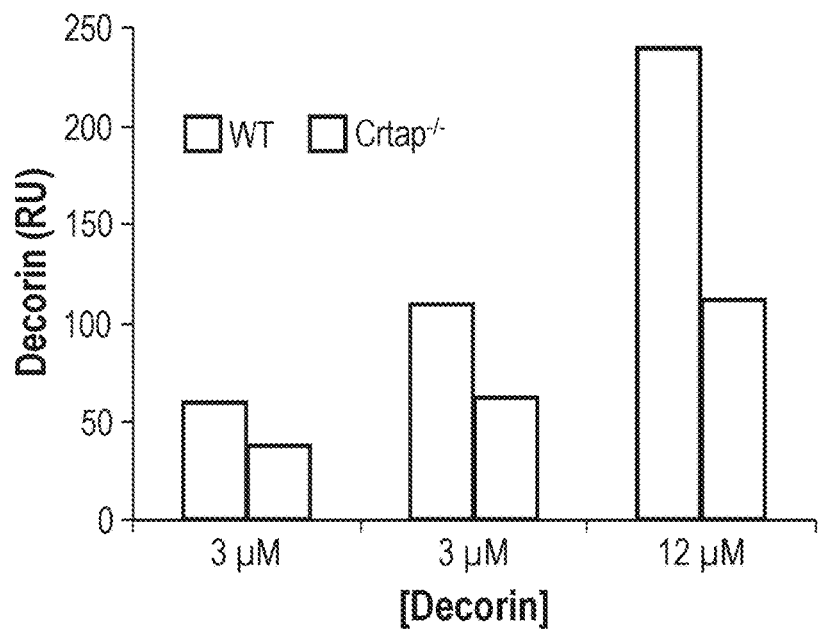
Figure 23:
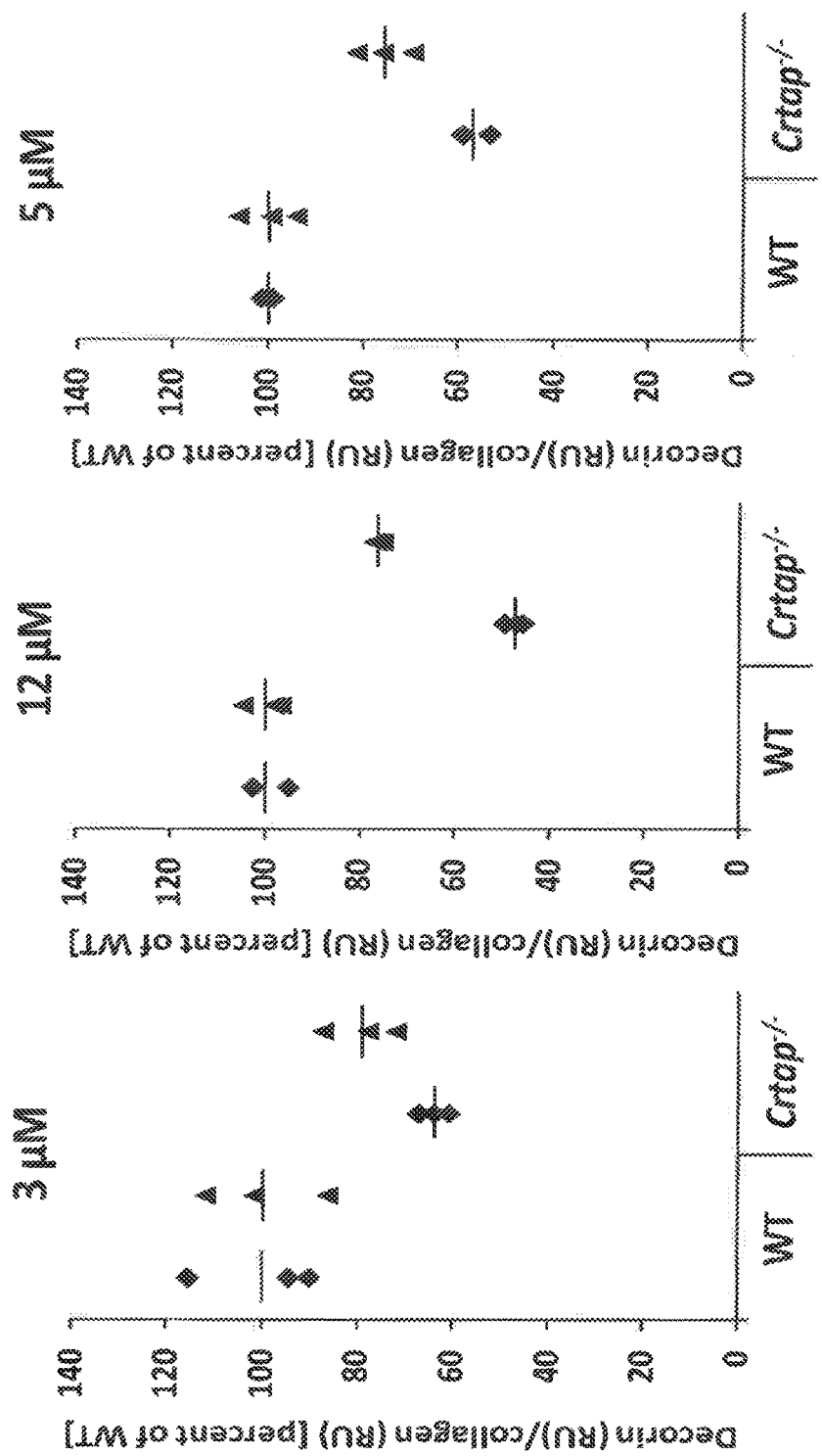
FIG. 23 is a graph showing surface plasmon resonance analysis measuring the binding of recombinant decorin core protein to type I collagen of WT and Crtap$^{-/-}$ mice. Three technical replicates at each of the indicated concentrations of decorin were performed from two independent biological replicates (♦ replicate 1, ▲ replicate 2). Results are shown as the percentage of the mean of WT (bars indicate mean per group).

Hence, it was hypothesized that decorin binding to collagen is critical for TGFβ regulation and that this binding is disrupted with altered collagen structure, for example by loss of post-translational 3-prolyl-hydroxylation modification of P986 in the α1 chain of type I collagen in the case of recessive OI. It was identified that although loss of Crtap did not alter the RNA expression of decorin and other SLRPs in calvarial bone (FIG. 12A), nor the qualitative abundance of decorin in trabecular bone (FIG. 24), it did reduce binding of recombinant decorin core protein to type I collagen isolated from Crtap$^{-/-}$ mice versus WT mice (FIG. 12B). Surface plasmon resonance analysis measurements of the binding of recombinant decorin core protein to type I collagen of WT and Crtap$^{-/-}$ mice demonstrated reduced binding in Crtap$^{-/-}$ mice at the three concentrations tested (FIG. 23). Three technical replicates at each of the indicated concentrations of decorin were performed from two independent biological replicates (♦ replicate 1, ▲ replicate 2). Results are shown as the percentage of the mean of WT (bars indicate mean per group). The mean reductions of decorin binding to Crtap$^{-/-}$ type I collagen at 3, 5 and 12 µM of decorin were 28.5%, 33.5% and 38.1%, respectively.

Figure 24:
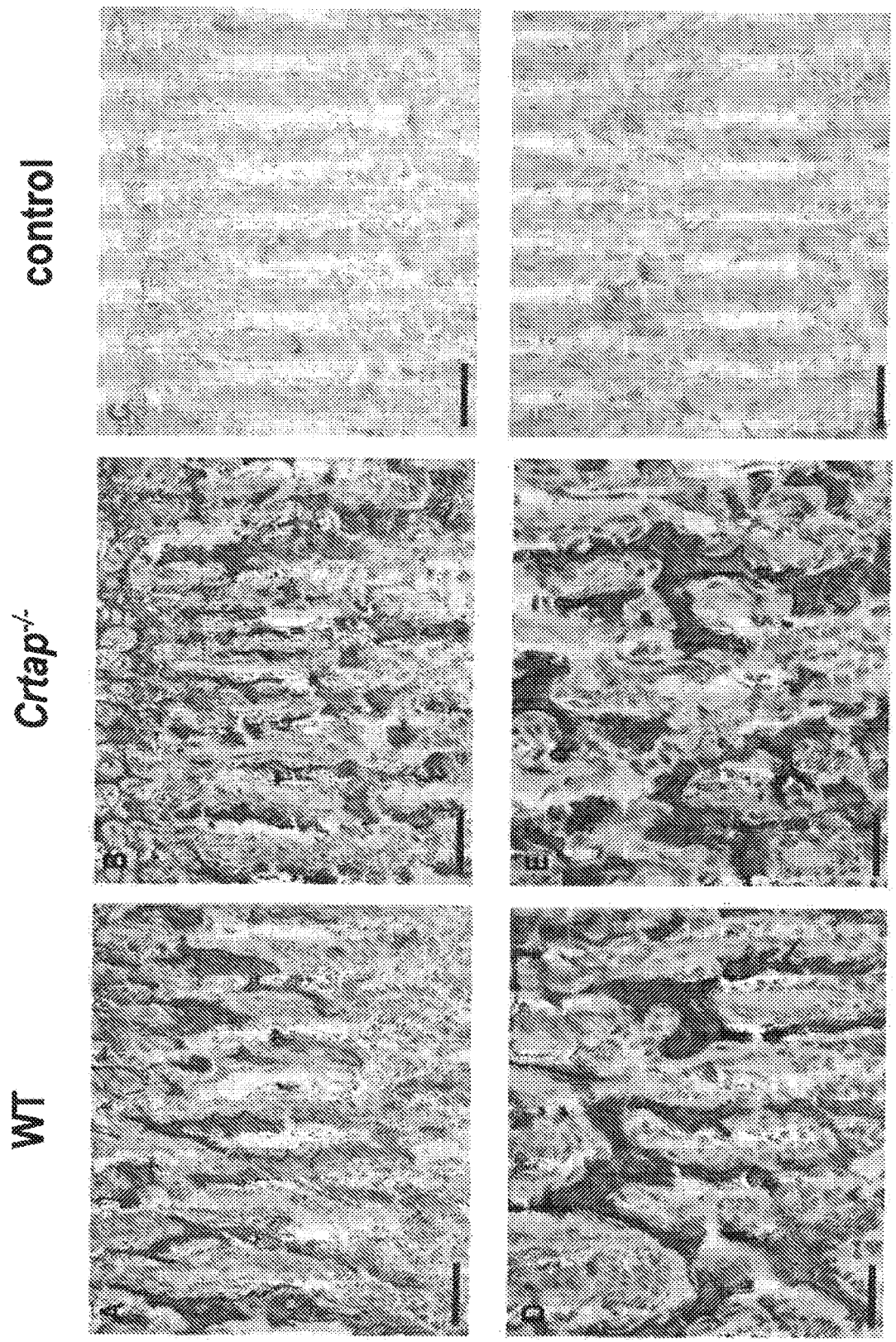
FIG. 24 (micrograph images) demonstrate immunostaining for decorin in the distal femur metaphysis of WT and Crtap$^{-/-}$ mice at 20λ, n=3 per genotype, scale bars=100 μm (Panels A-C) and 40× magnification, n=3 per genotype, scale bars=50 μm (Panels D-F). Control femurs were incubated in secondary antibody only.
Figure 25:
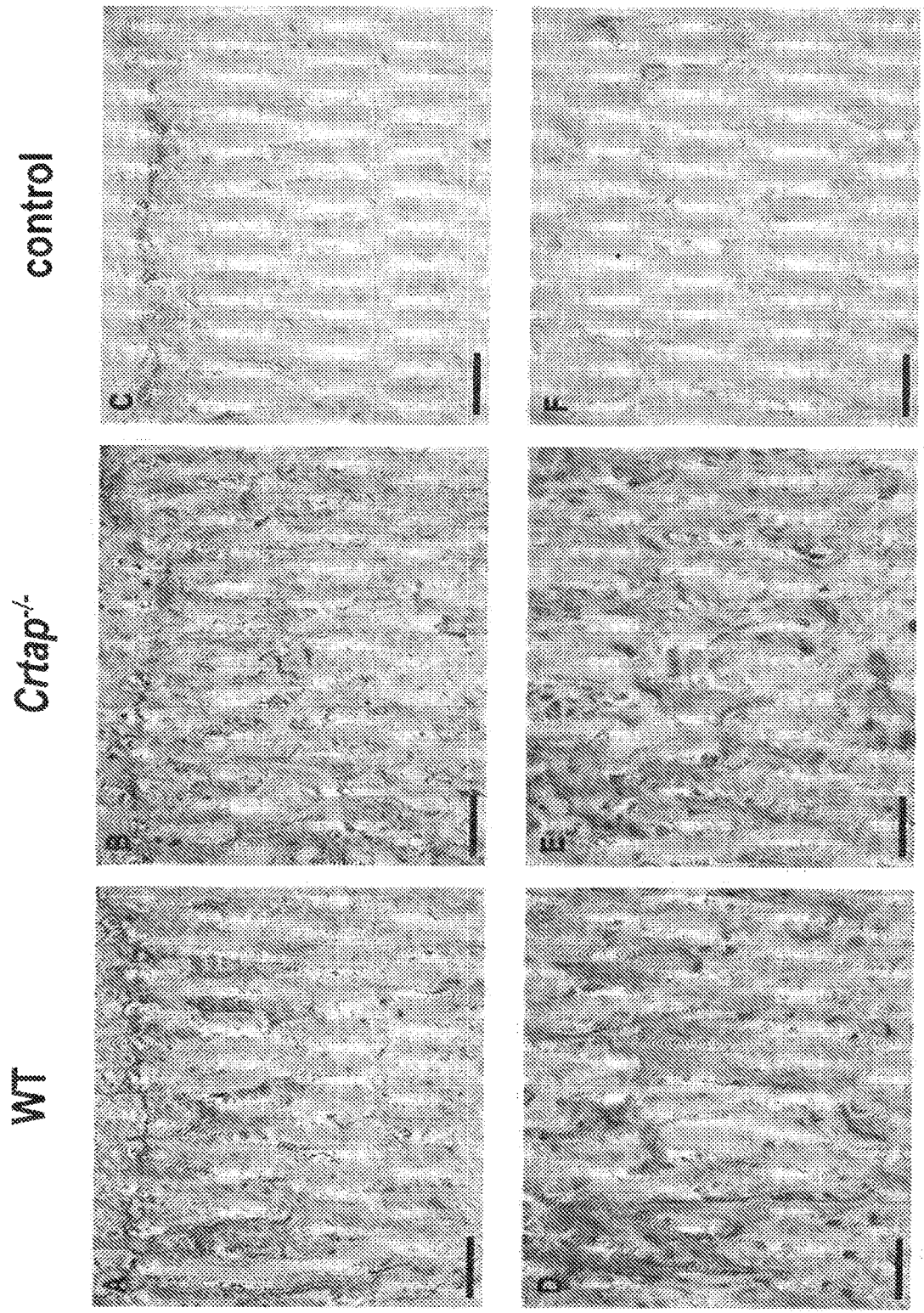
FIG. 25 (micrograph images) demonstrate immunostaining for TGFβ1 in the distal femur metaphysis of WT and Crtap$^{-/-}$ mice at 20λ, n=3 per genotype, scale bars=100 μm (Panels A-C) and 40× magnification, n=3 per genotype, scale bars=50 μm (Panels D-F). Control femurs were incubated in secondary antibody only.
Figure 26:
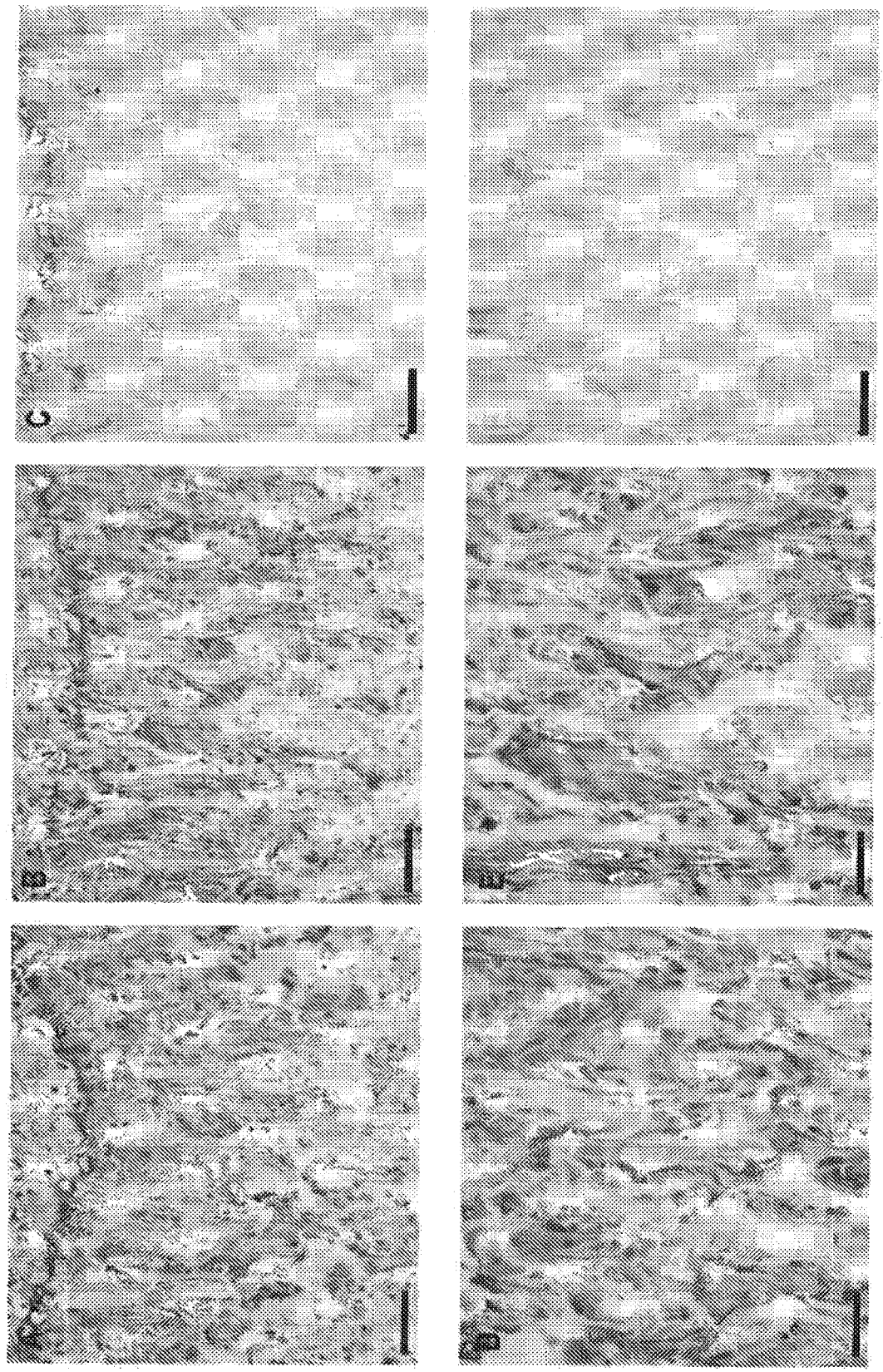
FIG. 26 (micrograph images) demonstrate immunostaining for TGFβ1 in the distal femur metaphysis of WT and Col1a2$^{tm1.1Mcbr}$ mice at 20λ, n=3 per genotype, scale bars=100 μm (Panels A-C) and 40× magnification, n=3 per genotype, scale bars=50 μm (Panels D-F). Control femurs were incubated in secondary antibody only.

This finding suggests that alterations of collagen-proteoglycan interactions may contribute to the dysregulated TGFβ signaling in bone and other collagen rich tissues in OI. Based on the reported requirement of decorin-collagen binding for decorin to effectively reduce TGFβ bioactivity, it is possible that the defects in OI collagen lead to altered binding of decorin, and hence, its ability to sequester TGFβ in the matrix and modulate TGFβ functions. Hence, altered proteoglycan-collagen interactions may contribute to dysregulated TGFβ signaling in bone and other collagen rich tissues in OI, even if no major changes in absolute TGFβ levels are present (FIG. 24 and FIG. 25). This notion is supported by the finding that COL1A1 and COL1A2 mutations in more severe forms of dominant OI cluster in specific regions that are known to bind proteoglycans, further supporting a physiological relevance of proteoglycan-collagen interactions for normal bone homeostasis. This would also imply that other proteoglycans that are competing with decorin for the collagen binding site may also contribute to dysregulated TGFβ activity, and that additional signaling pathways could be altered.

Because of the clinical overlap of some recessive and dominant forms of OI where defective structure of collagen fibers leads to brittle bones and extraskeletal manifestations, it is possible that dysregulation of TGFβ signaling is a common pathophysiological disease mechanism. To address this hypothesis, the status of TGFβ signaling in a mouse model of dominant OI was investigated. Knock-in mice carrying a G610C mutation in the Col1a2 gene (Col1a2$^{tm1.1Mcbr}$) phenocopy a dominantly inherited, moderate form of OI that was originally identified in an Amish population. In bone samples of Col1a2$^{tm1.1Mcbr}$ mice, increased expression of the TGFβ target genes p21 and PAI-1 was found, indicating upregulation of TGFβ signaling (FIG. 13A). Consistently, immunoblot analyses of bone extracts from Col1a2$^{tm1.1Mcbr}$ mice also showed an increased ratio of activated pSmad2/total Smad2, similar to our observation in the Crtap$^{-/-}$ mice (FIGS. 13B and 13C).

To test if the increased TGFβ signaling in this model of dominant OI also represents a causal mechanism, 8 week old Col1a2$^{tm1.1Mcbr}$ mice were treated with the TGFβ-neutralizing antibody 1D11 for 8 weeks; control Col1a2$^{tm1.1Mcbr}$ and WT mice were treated with the control antibody 13C4. Similar to the findings in Crtap$^{-/-}$ mice, 1D11-treatment restored the trabecular bone parameters at the spine to WT levels (FIGS. 13D, 13E, and 22). Taken together, these findings indicate that dysregulated TGFβ signaling is also an important contributor to the pathogenesis of dominant forms of OI, and that anti-TGFβ therapy corrects the bone phenotype in dominant OI.

From a clinical-translational perspective, potential negative effects of systemic TGFβ inhibition in OI patients have to be considered. While TGF-β1$^{-/-}$ mice develop a severe multifocal inflammatory disease and dysregulation of the immune system within the first weeks of life, in both Crtap$^{-/-}$ and Col1a2$^{tm1.1Mcbr}$ mice treated with 1D11 we did not observe obvious negative effects on general health, behavior or growth, suggesting that the effects of a partial pharmacological inhibition of TGFβ ligands in adult mice are different from a complete loss of TGFβ1 during development. In humans, Fresolimumab (GC1008, Genzyme), which is similar to 1D11 in its affinity and specificity to the 3 isoforms of TGFβ, was used in phase I studies in patients with treatment-resistant primary focal segmental glomerulosclerosis, idiopathic pulmonary fibrosis and malignant melanoma or renal cell carcinoma. In these studies, Fresolimumab was in general well-tolerated, with possible, dose-related adverse events including skin rashes or lesions, epistaxis, gingival bleeding and fatigue.

The molecular mechanisms of OI are incompletely understood. As a result, current treatment options for patients with OI are mainly limited to anti-resorptive therapies as used for the treatment of osteoporosis. Interestingly, a recent randomized, placebo controlled trial of the anabolic agent teriparatide in adults with OI showed that severe OI type III/IV responded differently than did those with mild OI type I (Orwoll et al., 2014). This suggests genotypic differences in response to therapies targeted at modifying cell signaling and that TGFβ-targeted treatment may be a promising option to further study in severe OI due to collagen and collagen post-translational modification gene mutations. Overall, our data support the concept of dysregulated matrix-cell signaling as a mechanism in the pathogenesis of different genetically inherited forms of brittle bone disease and point to a disease-specific mechanism-based strategy for the treatment of OI by neutralizing the overactive TGFβ activity in skeletal and extraskeletal tissues.

What is claimed is:

1. A method of treating osteogenesis imperfecta (OI) in a human subject in need thereof, comprising:
   administering to the subject an antibody or an antigen-binding fragment thereof that binds to transforming growth factor β (TGFB), wherein the antibody or antigen-binding fragment comprises heavy chain complementarity-determining regions (CDRs) 1-3 having the amino acid sequences of SEQ ID NOs: 4, 5, and 6, respectively; and light chain CDRs 1-3 having the amino acid sequences of SEQ ID NOs: 7, 8, and 9, respectively; and
   measuring the level of a bone parameter selected from the group consisting of bone volume density (BV/TV), total bone surface (BS), bone surface density (BS/BV), trabecular number (Tb.N), trabecular thickness (Tb.Th), trabecular spacing (Tb.Sp), and total volume (Dens TV), wherein the administering improves the bone parameter.

2. The method of claim 1, wherein the antibody comprises a heavy chain variable region ($V_H$) and a light chain variable region ($V_L$) comprising the amino acid sequences of SEQ ID NOs: 10 and 11, respectively.

3. The method of claim 1, wherein the antibody comprises a human $IgG_4$ constant region and a human κ light chain constant region.

4. The method of claim 1, wherein the antibody comprises a heavy chain and a light chain comprising the amino acid sequences of SEQ ID NOs: 14 and 15, respectively.

5. The method of claim 1, wherein the antibody or antigen-binding fragment thereof inhibits bone resorption.

6. The method of claim 1, wherein the antibody or antigen-binding fragment thereof promotes bone deposition.

7. The method of claim 1, wherein the antibody or antigen-binding fragment thereof improves the function of a non-skeletal organ affected by OI selected from the group consisting of hearing function, lung function, and kidney function.

8. The method of claim 1, wherein the subject has type I OI.

* * * * *